United States Patent
Yuan et al.

(10) Patent No.: US 9,725,452 B2
(45) Date of Patent: Aug. 8, 2017

(54) SUBSTITUTED INDOLES AND PYRROLES AS RIP KINASE INHIBITORS

(71) Applicants: President and Fellows of Harvard College, Cambridge, MA (US); Shanghai Institute of Organic Chemistry, Chinese Academy of Sciences, Shanghai (CN); Tufts University, Boston, MA (US); University of Houston, Houston, TX (US)

(72) Inventors: Junying Yuan, Newton, MA (US); Alexei Degterev, Brookline, MA (US); Gregory D. Cuny, Houston, TX (US)

(73) Assignees: Presidents and Fellows of Harvard College, Cambridge, MA (US); Shanghai Institute of Organic Chemistry, Chinese Academy of Sciences, Shanghai (CN); Tufts University, Boston, MA (US); University of Houston, Houston, TX (US)

(*) Notice: Subject to any disclaimer, the term of this patent is extended or adjusted under 35 U.S.C. 154(b) by 0 days.

(21) Appl. No.: 14/214,360

(22) Filed: Mar. 14, 2014

(65) Prior Publication Data
US 2014/0323489 A1    Oct. 30, 2014

Related U.S. Application Data

(60) Provisional application No. 61/792,891, filed on Mar. 15, 2013.

(51) Int. Cl.
| | |
|---|---|
| A61K 31/4025 | (2006.01) |
| A61K 31/404 | (2006.01) |
| C07D 207/30 | (2006.01) |
| C07D 209/04 | (2006.01) |
| C07D 487/04 | (2006.01) |
| C07D 401/14 | (2006.01) |
| C07D 471/04 | (2006.01) |

(52) U.S. Cl.
CPC ......... *C07D 487/04* (2013.01); *C07D 401/14* (2013.01); *C07D 471/04* (2013.01)

(58) Field of Classification Search
CPC .............. A61K 31/4025; A61K 31/404; C07D 207/30; C07D 209/04
USPC ......... 514/415, 427; 544/236; 546/121, 245; 548/226, 317.1, 469, 560
See application file for complete search history.

(56) References Cited

U.S. PATENT DOCUMENTS

| | | |
|---|---|---|
| 3,300,510 A | 1/1967 | Alburn et al. |
| 3,577,420 A | 5/1971 | Hess et al. |
| 3,932,430 A | 1/1976 | Habeck et al. |
| 4,016,037 A | 4/1977 | Mitsugi et al. |
| 4,105,776 A | 8/1978 | Ondetti et al. |
| 4,110,536 A | 8/1978 | Havera et al. |
| 4,177,054 A | 12/1979 | Arndt et al. |
| 4,302,386 A | 11/1981 | Stevens |
| 4,316,906 A | 2/1982 | Ondetti et al. |
| 4,332,952 A | 6/1982 | Schnur |
| 4,337,201 A | 6/1982 | Petrillo, Jr. |
| 4,344,949 A | 8/1982 | Hoefle et al. |
| 4,374,829 A | 2/1983 | Harris et al. |
| 4,410,520 A | 10/1983 | Watthey |
| 4,508,729 A | 4/1985 | Vincent et al. |
| 4,512,924 A | 4/1985 | Attwood et al. |
| 4,587,258 A | 5/1986 | Gold et al. |
| 4,618,609 A | 10/1986 | Alker et al. |
| 4,772,684 A | 9/1988 | Brunck et al. |
| 4,780,401 A | 10/1988 | Heusser et al. |
| 4,837,165 A | 6/1989 | Hawke |
| 4,845,079 A | 7/1989 | Luly et al. |
| 4,885,292 A | 12/1989 | Ryono et al. |

(Continued)

FOREIGN PATENT DOCUMENTS

| | | |
|---|---|---|
| CA | 1095872 A | 2/1981 |
| CA | 2639910 A1 | 8/2007 |
| DE | 27 28 523 A1 | 1/1979 |
| EP | 0253310 A2 | 1/1988 |
| EP | 0545478 A1 | 6/1993 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Abrantes et al., "Adaptation of a surface plasmon resonance biosensor with microfluidics for use with small sample volumes and long contact times," Anal Chem. 73(13):2828-35 (2001).

(Continued)

*Primary Examiner* — Douglas M Willis
(74) *Attorney, Agent, or Firm* — Choate, Hall & Stewart LLP; Brenda H. Jarrell; Nishat A. Shaikh

(57) ABSTRACT

The present invention relates to heterocyclic compounds (e.g., compounds described by Formula (I)) and pharmaceutically acceptable salts thereof. The invention also features pharmaceutical compositions that include these compounds and their use in therapy for treating conditions in which necroptosis is likely to play a substantial role. The heterocyclic compounds described herein can also achieve improved activity and selectivity towards RIP1 and/or RIP3.

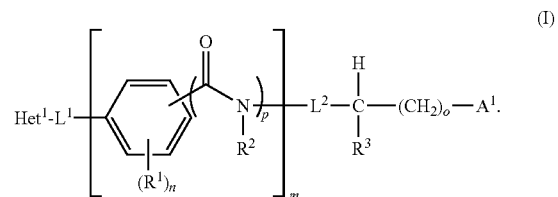

(I)

34 Claims, No Drawings

(56) References Cited

U.S. PATENT DOCUMENTS

| | | |
|---|---|---|
| 4,894,437 A | 1/1990 | TenBrink |
| 4,980,283 A | 12/1990 | Huang et al. |
| 5,034,512 A | 7/1991 | Hudspeth et al. |
| 5,036,053 A | 7/1991 | Himmelsbach et al. |
| 5,036,054 A | 7/1991 | Kaltenbronn et al. |
| 5,055,466 A | 10/1991 | Weller, III et al. |
| 5,063,207 A | 11/1991 | Doherty et al. |
| 5,063,208 A | 11/1991 | Rosenberg et al. |
| 5,064,825 A | 11/1991 | Chakravarty et al. |
| 5,064,965 A | 11/1991 | Ocain et al. |
| 5,066,643 A | 11/1991 | Abeles et al. |
| 5,071,837 A | 12/1991 | Doherty et al. |
| 5,073,566 A | 12/1991 | Lifer et al. |
| 5,075,451 A | 12/1991 | Ocain et al. |
| 5,081,127 A | 1/1992 | Carini et al. |
| 5,085,992 A | 2/1992 | Chen et al. |
| 5,087,634 A | 2/1992 | Reitz et al. |
| 5,089,471 A | 2/1992 | Hanson et al. |
| 5,095,006 A | 3/1992 | Bender et al. |
| 5,095,119 A | 3/1992 | Ocain et al. |
| 5,098,924 A | 3/1992 | Poss |
| 5,104,869 A | 4/1992 | Albright et al. |
| 5,106,835 A | 4/1992 | Albright et al. |
| 5,108,914 A | 4/1992 | Wagner et al. |
| 5,114,937 A | 5/1992 | Hamby et al. |
| 5,116,835 A | 5/1992 | Ruger et al. |
| 5,334,606 A | 8/1994 | MacLeod |
| 5,474,995 A | 12/1995 | Ducharme et al. |
| 5,521,213 A | 5/1996 | Prasit et al. |
| 5,536,752 A | 7/1996 | Ducharme et al. |
| 5,543,297 A | 8/1996 | Cromlish et al. |
| 5,550,142 A | 8/1996 | Ducharme et al. |
| 5,552,422 A | 9/1996 | Gauthier et al. |
| 5,593,697 A | 1/1997 | Barr et al. |
| 5,604,253 A | 2/1997 | Lau et al. |
| 5,639,780 A | 6/1997 | Lau et al. |
| 5,643,933 A | 7/1997 | Talley et al. |
| 5,677,318 A | 10/1997 | Lau |
| 5,691,374 A | 11/1997 | Black et al. |
| 5,693,643 A | 12/1997 | Gilbert et al. |
| 5,698,584 A | 12/1997 | Black et al. |
| 5,710,140 A | 1/1998 | Ducharme et al. |
| 5,733,909 A | 3/1998 | Black et al. |
| 5,789,413 A | 8/1998 | Black et al. |
| 5,817,700 A | 10/1998 | Dube et al. |
| 5,849,943 A | 12/1998 | Atkinson et al. |
| 5,861,419 A | 1/1999 | Dube et al. |
| 5,922,742 A | 7/1999 | Black et al. |
| 5,925,631 A | 7/1999 | Black et al. |
| 6,194,444 B1 | 2/2001 | Tsubata et al. |
| 6,211,337 B1 | 4/2001 | Baichwal et al. |
| 6,277,852 B1 | 8/2001 | Howard |
| 6,300,349 B1 | 10/2001 | Margolin |
| 6,420,400 B1 | 7/2002 | Zhang et al. |
| 6,521,649 B1 | 2/2003 | Kuroda et al. |
| 6,541,630 B1 | 4/2003 | Atherall et al. |
| 6,756,394 B1 | 6/2004 | Yuan et al. |
| 6,797,708 B2 | 9/2004 | McKew et al. |
| 6,846,839 B1 | 1/2005 | Tang et al. |
| 6,887,993 B1 | 5/2005 | Tian et al. |
| 7,229,991 B2 | 6/2007 | Merla et al. |
| 7,253,201 B2 | 8/2007 | Yuan et al. |
| 7,491,743 B2 | 2/2009 | Cuny et al. |
| 8,143,300 B2 | 3/2012 | Cuny et al. |
| 8,278,344 B2 | 10/2012 | Cuny et al. |
| 8,324,262 B2 | 12/2012 | Yuan et al. |
| 8,658,689 B2 | 2/2014 | Cuny et al. |
| 8,741,942 B2 | 6/2014 | Cuny et al. |
| 9,108,955 B2 | 8/2015 | Cuny et al. |
| 9,499,521 B2 | 11/2016 | Yuan et al. |
| 2002/0013350 A1 | 1/2002 | Nishiguchi et al. |
| 2002/0155172 A1 | 10/2002 | Yuan et al. |
| 2003/0083386 A1 | 5/2003 | Yuan et al. |
| 2003/0191134 A1 | 10/2003 | Shapiro et al. |
| 2004/0259904 A1 | 12/2004 | Tong et al. |
| 2005/0038053 A1 | 2/2005 | Hirvelae et al. |
| 2005/0119260 A1 | 6/2005 | Cuny et al. |
| 2005/0131044 A1 | 6/2005 | Yuan et al. |
| 2005/0288282 A1 | 12/2005 | Delorme et al. |
| 2006/0019952 A1 | 1/2006 | Distefano et al. |
| 2006/0019953 A1 | 1/2006 | Hale et al. |
| 2006/0198893 A1 | 9/2006 | Lindfors |
| 2007/0037752 A1 | 2/2007 | Ansorge et al. |
| 2007/0093489 A1 | 4/2007 | Javaid et al. |
| 2007/0099936 A1 | 5/2007 | Bian et al. |
| 2007/0191376 A1 | 8/2007 | Zou et al. |
| 2007/0197551 A1 | 8/2007 | Sato et al. |
| 2008/0045541 A1 | 2/2008 | Gielen-Haertwig et al. |
| 2008/0234270 A1 | 9/2008 | Canne Bannen et al. |
| 2009/0099186 A1 | 4/2009 | Beigelman et al. |
| 2009/0099242 A1 | 4/2009 | Cuny et al. |
| 2009/0163545 A1 | 6/2009 | Goldfarb |
| 2010/0087453 A1 | 4/2010 | Yuan et al. |
| 2010/0190836 A1 | 7/2010 | Yuan et al. |
| 2010/0317701 A1 | 12/2010 | Cuny et al. |
| 2011/0144169 A1 | 6/2011 | Cuny et al. |
| 2012/0122889 A1 | 5/2012 | Yuan et al. |
| 2012/0149702 A1 | 6/2012 | Cuny et al. |
| 2012/0309795 A1 | 12/2012 | Cuny et al. |
| 2013/0158024 A1 | 6/2013 | Yuan et al. |
| 2014/0024657 A1 | 1/2014 | Yuan et al. |
| 2014/0024662 A1 | 1/2014 | Yuan et al. |
| 2014/0128437 A1 | 5/2014 | Cuny et al. |
| 2014/0323489 A1 | 10/2014 | Yuan et al. |
| 2016/0024098 A1 | 1/2016 | Yuan et al. |
| 2016/0102053 A1 | 4/2016 | Cuny et al. |
| 2016/0168128 A1 | 6/2016 | Yuan et al. |
| 2016/0304498 A1 | 10/2016 | Yuan et al. |

FOREIGN PATENT DOCUMENTS

| | | |
|---|---|---|
| EP | 0343643 B1 | 3/1994 |
| EP | 0930305 A1 | 7/1999 |
| EP | 0976326 A1 | 2/2000 |
| EP | 1275646 A1 | 1/2003 |
| EP | 1438973 A1 | 7/2004 |
| EP | 1447401 A1 | 8/2004 |
| EP | 1852428 A1 | 11/2007 |
| GB | 2001623 A | 2/1979 |
| GB | 2080803 A | 2/1982 |
| JP | S54-9272 A | 1/1979 |
| JP | S55-23994 A | 2/1980 |
| JP | S61-22081 A | 1/1986 |
| JP | H02-19363 A | 1/1990 |
| JP | H05-4910 A | 1/1993 |
| JP | H10-152482 A | 6/1998 |
| JP | 2000-103710 A | 4/2000 |
| JP | 2002/330785 A | 11/2002 |
| JP | 2003/198785 A | 7/2003 |
| JP | 2005-519932 A | 7/2005 |
| JP | 2006-527226 A | 11/2006 |
| JP | 2007-099749 A | 4/2007 |
| JP | 2007-508349 A | 4/2007 |
| JP | 2007-186435 A | 7/2007 |
| JP | 2007-529422 A | 10/2007 |
| JP | 2008-517061 A | 5/2008 |
| JP | 2009-530402 A | 8/2009 |
| JP | 2009-530409 A | 8/2009 |
| JP | 2010-522242 A | 7/2010 |
| JP | 2010275229 A | 12/2010 |
| JP | 49-66678 B2 | 7/2012 |
| JP | 5262728 B2 | 8/2013 |
| JP | 2016-514693 A | 5/2016 |
| WO | WO-90/04183 A1 | 4/1990 |
| WO | WO-92/04045 A1 | 3/1992 |
| WO | WO-92/04381 A1 | 3/1992 |
| WO | WO-95/00501 A2 | 1/1995 |
| WO | WO-95/18799 A1 | 7/1995 |
| WO | WO-96/30393 A1 | 10/1996 |
| WO | WO-98/02162 A1 | 1/1998 |
| WO | WO-98/39303 A1 | 9/1998 |
| WO | WO-01/28493 A2 | 4/2001 |
| WO | WO-01/85718 A1 | 11/2001 |
| WO | WO 02/02568 | 1/2002 |

(56) References Cited

FOREIGN PATENT DOCUMENTS

| | | |
|---|---|---|
| WO | WO-0244157 A2 | 6/2002 |
| WO | WO-03/030937 A1 | 4/2003 |
| WO | WO-03/037898 A1 | 5/2003 |
| WO | WO-03/068747 A1 | 8/2003 |
| WO | WO-2004/058707 A1 | 7/2004 |
| WO | WO-2004/070050 A2 | 8/2004 |
| WO | WO-2005/000821 A1 | 1/2005 |
| WO | WO-2005/028664 A2 | 3/2005 |
| WO | WO-2005/032527 A2 | 4/2005 |
| WO | WO-2005/037257 A2 | 4/2005 |
| WO | WO-2005/072412 A2 | 8/2005 |
| WO | WO-2005/077344 A2 | 8/2005 |
| WO | WO-2006/012642 A2 | 2/2006 |
| WO | WO-2006/044826 A2 | 4/2006 |
| WO | WO-2006/081391 A2 | 8/2006 |
| WO | WO-2006/086358 A2 | 8/2006 |
| WO | WO-2006/098128 A1 | 9/2006 |
| WO | WO-2007/047146 A2 | 4/2007 |
| WO | WO-2007/047604 A2 | 4/2007 |
| WO | WO-2007/059905 A2 | 5/2007 |
| WO | WO-2007/075772 A2 | 7/2007 |
| WO | WO-2007/087427 A2 | 8/2007 |
| WO | WO-2007/087906 A1 | 8/2007 |
| WO | WO-2007/089904 A2 | 8/2007 |
| WO | WO-2007/109362 A2 | 9/2007 |
| WO | WO-2007/112093 A2 | 10/2007 |
| WO | WO-2008/006883 A2 | 1/2008 |
| WO | WO-2008/045406 A2 | 4/2008 |
| WO | WO-2008/063667 A1 | 5/2008 |
| WO | WO-2008/118758 A1 | 10/2008 |
| WO | WO-2008/147962 A1 | 12/2008 |
| WO | WO-2009/023272 A1 | 2/2009 |
| WO | WO-2009/086303 A2 | 7/2009 |
| WO | WO-2009/109983 A1 | 9/2009 |
| WO | WO-2010/075290 A1 | 7/2010 |
| WO | WO-2010/075561 A1 | 7/2010 |
| WO | WO-2011/133964 A2 | 10/2011 |
| WO | WO-2012/061045 A2 | 5/2012 |
| WO | WO-2012/125544 A2 | 9/2012 |
| WO | WO 2014/145022 * | 9/2014 |
| WO | WO-2014/152182 A1 | 9/2014 |
| WO | WO-2016/094846 A1 | 6/2016 |

OTHER PUBLICATIONS

Angers et al., "Detection of beta 2-adrenergic receptor dimerization in living cells using bioluminescence resonance energy transfer (BRET)," Proc Natl Acad Sci USA. 97(7):3684-9 (2000).
Bader et al., "A cGMP-dependent protein kinase assay for high throughput screening based on time-resolved fluorescence resonance energy transfer," J Biomol Screen. 6(4):255-264 (2001).
Barth et al., "Combining phage display and screening of cDNA expression libraries: a new approach for identifying the target antigen of an scFv preselected by phage display," J Mol Biol. 301(4):751-7 (2000).
Brockhoff et al., "Epidermal growth factor receptor, c-erbB2 and c-erbB3 receptor interaction, and related cell cycle kinetics of SK-BR-3 and BT474 breast carcinoma cells," Cytometry. 44(4):338-48 (2001).
Chan, "Fueling the flames: Mammalian programmed necrosis in inflammatory diseases," Cold Spring Harb Perspect Biol. 4(11):1-12 (2012).
Christofferson et al., "Necroptosis as an alternative form of programmed cell death," Curr Opin Cell Biol. 22(2):263-8 (2010).
Degterev et al., "Chemical inhibitor of nonapoptotic cell death with therapeutic potential for ischemic brain injury," Nat Chem Biol. 1(2):112-9, 234 (2005).
Engelborghs, "The analysis of time resolved protein fluorescence in multi-tryptophan proteins," Spectrochim Acta A Mol Biomol Spectrosc. 57(11):2255-70 (2001).
Ferrell et al., Acute viral hepatitis. *Pathology of the Liver, 4th Edition.* R.N.M MacSween, A.D. Burt, B.C. Portmann, K.G. Ishak, P.J. Scheuer, P.P. Anthony, 314-325 (2002).

Geoghegan et al., "Dye-pair reporter systems for protein-peptide molecular interactions," Bioconjug Chem. 11(1):71-7 (2000).
Giglio et al. "Cerebral radiation necrosis," Neurologist. 9(4):180-88 (2003).
International Search Report and Written Opinion for International Patent Application No. PCT/US14/29658, mailed Aug. 1, 2014 (11 pages).
Jagtap et al., "Structure-activity relationship study of tricyclic necroptosis inhibitors." J Med Chem. 50(8):1886-95 (2007).
Kang et al., "Caspase-8 blocks kinase RIPK3-mediated activation of the NLRP3 inflammasome," Immunity. 38(1):27-40 (2013).
Kaplowitz, "Mechanisms of liver cell injury," J Hepatol. 32 (Suppl. 1):39-47 (2000).
Lin et al., "A role of RIP3-mediated macrophage necrosis in atherosclerosis development," Cell Rep. 3(1):200-10 (2013).
Lo et al., "Mechanisms, challenges and opportunities in stroke," Nat Rev Neurosci. 4(5):399-415 (2003).
Malhi et al., "Apoptosis and necrosis in the liver: a tale of two deaths," J Hepatology. 43(Suppl. 1):S31-S44 (2006).
Mareninova et al., "Cell death in pancreatitis. Caspases protect from necrotizing pancreatitis," J Biol Chem. 281(6):3370-81 (2006).
Martin et al., "Neurodegeneration in excitotoxicity, global cerebral ischemia, and target deprivation: A perspective on the contributions of apoptosis and necrosis." Brain Res Bull. 46(4):281-309 (1998).
McCully et al., "Differential contribution of necrosis and apoptosis in myocardial ischemia-reperfusion injury," Am J Physiol Heart Circ Physiol. 286(5):H1923-35 (2004).
Miyaguchi et al. "Laryngeal necrosis after combined chemotherapy and radiation therapy," J Laryngol Otol. 111(8):763-5 (1997).
Nelson et al., "Advances in surface plasmon resonance biomolecular interaction analysis mass spectrometry (BIA/MS)," J Mol Recognit. 12(2):77-93 (1999).
Osborne et al., "Retinal ischemia: mechanisms of damage and potential therapeutic strategies," Prog Retin Eye Res. 23(1):91-147 (2004).
Ramesh et al., "TNFR2-mediated apoptosis and necrosis in cisplatin-induced acute renal failure," Am J Physiol Renal Physiol. 285:F610-F618 (2003).
Rich et al., "BIACORE J: a new platform for routine biomolecular interaction analysis," J Mol Recognit. 14(4):223-8 (2001).
Rosai. "Pancreatitis", *Rosai and Ackerman's Surgical Pathology*, Mosby ed., 1063-1067 (2004).
Song et al., "Detection of multivalent interactions through two-tiered energy transfer," Anal Biochem. 291(1):133-41 (2001).
Spiga et al., "Peptide-protein interactions studied by surface plasmon and nuclear magnetic resonances," FEBS Lett. 511(1-3):33-5 (2002).
Teng et al.,"Structure-activity relationship study of novel necroptosis inhibitors," Bioorg Med Chem Lett. 15(22):5039-44 (2005).
Wallach et al., "'Necrosome'-induced inflammation: must cells die for it?," Trends Immunol. 32(11):505-9 (2011).
Wong et al., "Nonpeptide angiotensin II receptor antagonists. I. Pharmacological characterization of 2-n-butyl-4-chloro-1-(2-chlorobenzyl)imidazole-5-acetic acid, sodium salt (S-8307)," J Pharmacol Exp Ther. 247(1):1-7 (1988).
Wrobleski et al., "Necrotizing pancreatitis: pathophysiology, diagnosis, and acute care management," AACN Clin Issues. 10(4):464-77 (1999).
Wyllie et al., "Cell death: the significance of apoptosis." Int Rev Cytol. 68:251-306 (1980).
Xie et al., "Structural basis of RIP1 inhibition by necrostatins," Structure. 21(3):493-9 (2013).
Xu et al., "A bioluminescence resonance energy transfer (BRET) system: application to interacting circadian clock proteins," Proc Natl Acad Sci USA. 96(1):151-6 (1999).
Argast et al., Inhibition of RIP2/RICK/CARDIAK activity by pyridinyl imidazole inhibitors of p38 MAPK, Mol Cell Biochem. 268(1-2):129-40 (2005).
Berge et al., Pharmaceutical salts, J Pharm Sci. 66(1):1-19 (1977).
Bhatia, "Apoptosis versus necrosis in acute pancreatitis," Am J Physiol Gastrointest Liver Physiol. 286(2):G189-G196 (2004).

(56) References Cited

OTHER PUBLICATIONS

Bisson et al., "Binding properties of the C-terminal domain of VIAF," Chem Biol Drug Des. 72(5):331-6 (2008).
Boeijen, "Combinatorial chemistry of hydantoins," Bioorganic & Medical Chem Lett. 8(17):2375-80 (1998).
Borner et al., "Apoptosis without caspases: an inefficient molecular guillotine?" Cell Death Differ. 6(6):497-507 (1999).
Brana et al., "Reaction of L-tryptoohan with alkyl isocyanates." Heterocycles. 26(1):95-100 (1987).
Burk et al., "A convenient asymmetric synthesis of alpha-1-arylalkylamines through the enantioselective hydroaenation of enamides," J Am Chem Soc. 118:5142-3 (1996).
Butukbingol et al., "Studies on the synthesis and structure-activity relationships of 5-(3'-indolal)-2-thiohydantoin derivatives as aldose reductase enzyme inhibitors." Farmaco. 49(6):443-7 (1994).
Byrn et al., Hydrates and Solvates. Solid-State Chemistry of Drugs. SSCI, Inc., 233-247 (1999).
Caplus Accession for EP 313397B, dated Jun. 2, 1993 (2 oaaes).
Caplus Accession for Jakse et al., "New synthetic routes to thiooxoaplysinopsines and their derivatives," Zbornik Referatov s Posvetovanja Slovenski Kemijski Dnevi, Maribor, Slovenia, Sep. 28-29, 2000 (2 pages).
Caplus Accession for Nowak, "Allyl Isothiocyanate in the synthesis of 3-allyl-2-thiohydantoins from amino acids and in the degradation of proteins," Roczniki Chemii. 47(12):2377-8 (1973) (2 pages) (Abstract only).
Caplus Accession for US 20090163545, dated Jun. 25, 2009 (5 oaaes).
Caplus Accession for U.S. Pat. No. 4,110,536, dated Aug. 29, 1978 (2 pages).
Caplus Accession for WO 96/30393, dated Oct. 3, 1996 (2 oaaes).
Chi et al., "Oncogenic ras triggers cell suicide through the activation of a caspase-independent cell death program in human cancer cells." Oncogene. 18(13):2281-90 (1999).
Cryns et al., "Proteases to die for," Genes Dev. 12(11):1551-70 (1998).
Database Registry Online (STN) for RN-903319-98-2. Retrieved Aug. 22, 2006 (1 page).
Edman, "Method for determination of the amino acid sequence in peptides." Acta Chem Scand. 4:283-93 (1950).
El-Rayyes et al.,"Heterocycles. Part VIII. Synthesis of new substituted benz[g]indazoles," J Heterocyclic Chem. 23:135-40 (1986).
Eldadah et al., "Caspase pathways, neuronal apoptosis, and CNS injury," J Neurotrauma. 17(10):811-29 (2000).
Extended European Search Report from European Application No. 09835866.6, dated Jul. 18, 2012 (22 pages).
Faden. "Neuroprotection and traumatic brain injury: theoretical option or realistic proposition," Curr Opin Neural. 15:707-12 (2002).
Fiers et al., "More than one way to die: apoptosis, necrosis and reactive oxygen damage." Oncogene. 18(54):7719-30 (1999).
Fujiwara et al., "13C nuclear magnetic resonance studies on the conformation of substituted hydantoins." J Chem Soc Perkin Trans 2. 1573-7 (1980).
Gennarelli et al., "Neuropathology", Textbook of Traumatic Brain Injury; American Psychiatric Publishing Inc, 27-50 (2005).
Gravier et al., "Thieno [2,3-d] pyrimidin-4(3H)-one derivatives and 1,2-dihydrogenated homologues: synthesis, enhanced in vitro antiaggregant activity for reduced compounds," Pharmazie. 47(10):754-7 (1992).
Gryglewski et al., "Thrombolysis by thienopyridines and their congeners," J Physiol Pharmacol. 51 (4 Pt 1):683-93 (2000).
Gulati et al., "A new synthesis of 5-bromoaplysinopsin, 6-bromoaplysinopsin and 3'-demethvlaolvsinoosin and their bioloaical activities." Indian J Chem. 338(1):10-6 (1994).
Hahnen et al., "Histone deacetylase inhibitors: possible implications for neurodegenerative disorders," Expert Opin Investig Drugs. 17(2):169-84 (2008).

Hara et al., "Inhibition of interleukin 1 beta converting enzyme family proteases reduces ischemic and excitotoxic neuronal damaae." Proc Natl Acad Sci U.S.A. 94(5):2007-12 (1997).
Herceg et al., "Failure of poly(ADP-ribose) polymerase cleavage by caspases leads to induction of necrosis and enhanced aoootosis." Mol Cell Biol. 19(7):5124-33 (1999).
Hirsch et al., "The apoptosis-necrosis paradox. Apoptogenic proteases activated after mitochondrial permeability transition determine the mode of cell death." Oncogene. 15(13):1573-81 (1997).
Hitomi et al., "Identification of a molecular signaling network that regulates a cellular necrotic cell death pathway," Cell. 135(7):1311-23 (2008).
Holler et al., "Fas triggers an alternative, caspase-8-indepdendent cell death pathway using the kinase RIP as effector molecule." Nature Immunol. 1 (6):489-95 (2000).
Horwell et al., "Conformationally constrained amino-acids: synthesis of novel beta, beta-, 2,3-, and 3,4-cyclised tryptophans." Tetrahedron Lett. 39(47):8729-32 (1998).
Inglis et al., "The identification of tryptophan residues in proteins as oxidised derivatives during amino acid sequence determinations." FEBS Letters. 104(1):115-8 (1979).
International Preliminary Report on Patentability for International Application No. PCT/US2014/029358, dated Oct. 20, 2015 (11 pages).
International Search Report and Written Opinion of the International Search Authority for International Application No. PCT/US2006/048583, mailed Dec. 8, 2008 (9 pages).
International Search Report for International Application No. PCT/US08/09793, mailed Nov. 3, 2008 (1 page).
International Search Report for International Patent Application No. PCT/US2004/028270, dated Jan. 18, 2006 (6 pages).
Janin et al., "Methyl orthocarboxylates as methylating agents of heterocycles." Eur J Org Chem. 1763-9 (2002).
Jones, G. et al., Photoinduced Electron Transfer Involving Eosin-Tryptophan Conjugates, Long-Lived Radical Pair States for Systems Incorporating Aromatic Amino Acid Side Chains, J. Phys. Chem., 98:6906-6909 (1994).
Joucla et al., "Synthesis of fused heterocycles with a benzazepinone moiety via intramolecular Heck coupling," Tetrahedron Lett. 46(47):8177-8179 (2005).
Kaplowitz. "Cell death at the millennium. Implications for liver diseases," Clin Liver Dis. 4(1 ):123 (2000).
Kaul et al., "Pathways to neuronal injury and apoptosis in HIV-associated dementia." Nature. 410(6831):988-94 (2001).
Kawahara et al., "Caspase-independent cell killing by fas-associated protein with death domain." J Cell Biol. 143(5):1353-60 (1998).
Kawauchi, H. and Tuzimura, K., Reaction of Fluorescein-isothiocyanate with Proteins and Amino Acids Part III. Syntheses of Trifluoroacetic Acid Salts of Fluorescein-thiohydantoin Amino Acids and their Spectrometric Studies, Agr. Biol. Chem., 35(2):150-157 (1971).
Kazlauskas et. al., "Aplysinopsin, a new tryptophan derivative from a sponge." Tetrahedron Lett. 1:61-4 (1977).
Khodair, "A convenient synthesis of glycosylated hydantoins as potential antiviral agents." Phosphorus Sulfur Silicon Relat Elem. 122:9-26 (1997).
Khwaja et al., "Resistance to the cytotoxic effects of tumor necrosis factor alpha can be overcome by inhibition of a FADD/Caspase-dependent signaling pathway." J Biol Chem. 274(51):36817-23 (1999).
Kitanaka et al., "Caspase-independent programmed cell death with necrotic morphology." Cell Death Differ. 6(6):508-15 (1999).
Ichihara et al., "The acid diazo reaction and 5- or 7-hydroxyindole derivatives: oxidation of the benzene moiety of indolelactic acid, indolepropionic acid, and indolylethylamine, etc., by liver extract," J Biochem. (Tokyo) 44:649-59 (1957) (abstract only).
Leist et al., "Inhibition of mitochondrial ATP generation by nitric oxide switches apoptosis to necrosis." Exp Cell Res. 249(2):396-403 (1999).
Lewis et al., "Tryptophan-derived NK1 antagonists: conformationally constrained heterocyclic bioisosteres of the ester linkage." J Med Chem. 38:923-33 (1995).

(56) References Cited

OTHER PUBLICATIONS

Li et al., "Induction of necrotic-like cell death by tumor necrosis factor alpha and caspase inhibitors: novel mechanism for killing virus-infected cells." J Viral. 74(16):7470-7 (2000).
Luschen et al., "Sensitization to death receptor cytotoxicity by inhibition of fas-associated death domain protein (FADD)/caspase signaling. Requirement of cell cycle progression." J Biol Chem. 275(32):24670-8 (2000).
Manhas et al., Heterocyclic compounds. 4. Synthesis and antiinflammatory activity of some substituted thienopyrimidones, J Med Chem. 15(1):106-7 (1972).
Marchant et al., "Synthesis of 5- and 7-methoxytryptophan and of some derivatives," J Chem Soc. 1808-11 (1951) (Abstract only).
Matsumura et al., "Necrotic death pathway in fas receptor signaling." J Cell Biol. 151 (6):124755 (2000).
Mayo Clinic staff, "Liver problems: Treatments and drugs," <http://www.mayoclinic.com/health/liver-problems/DSO 1133/DS E CT 10 N=treatments-and-drugs>, retrieved on May 20, 2011 (2 pages).
McCarthy et al., "Inhibition of ced-3/ICE-related proteases does not prevent cell death induced by oncogenes, DNA damage, or the Bcl-2 homologue bak." J Cell Biol. 136(1):215-27 (1997).
McMurray, "Huntington's disease: new hope for therapeutics." Trends Neurosci. 24(11 Suppl):532-8 (2001).
Molina et al., "A simple and general entry to aplysinopsine-type alkaloids by tandem azawittig/heterocumulene-mediated annelation." Tet Lett. 33(31):4491-4 (1992).
Morissette et al., "High-throughput crystallization: polymorphs, salts, co-crystals and solvates of pharmaceutical solids," Adv Drug Deliv Rev. 56(3):275-300 (2004).
NCBI Compound Summary for CID 3928273, <http://pubchem.ncbi.nlm.nih.gov/compound/3928273>, retrieved Jun. 3, 2015 (13 pages).
Nicotera et al., "Apoptosis and necrosis: different execution of the same death." Biochem Soc Svmp. 66:69-73 (1999).
Nowak, "Application of allylisothiocyanate in synthesis of 3-allyl-2-thiohydantoins from amino acids and in the degradation of proteins," Roczniki Chemii. 47(12):2377-8 (1973).
Oikawa et al., "Meldrum's Acid in Organic Synthesis. 2. A General and Versatile Synthesis of Beta-Keto Esters," J Ora Chem. 43(10):2087-8 (1978).
Ooms et al., "Exploration of the pharmacophore of 3-alkyl-5-arylimidazolidinediones as new CB1 cannabinoid receptor ligands and potential antagonists: synthesis, lipophilicity, affinity and molecular modeling." J Med Chem. 45(9):1748-56 (2002).
Park et al., "Diastereoselective synthesis of hydantoin- and isoxazoline-substituted dispirocyclobutanoids." J Org Chem. 65(11):3520-4 (2000).
Partial European Search Report for European Application No. 10011481.8, dated Jun. 7, 2011 (6 pages).
Patani et al., "Bioisosterism: A rational approach in drug design," Chem. Rev. 96: 3147-3176 (1996).
Polniaszek et al., "Stereoselective nucleophilic additions to the carbon-nitrogen double bond. 3.chiral acyliminium ions." J Org Chem. 55(1):215-23 (1990).
Polverino et al., "Selective activation of caspases during apoptotic induction in HL-60 cells." J Biol Chem. 272(11):7013-21 (1997).
Raghupathi et al., "Apoptosis after traumatic brain iniurv," J Neurotrauma. 17(10):927-38 (2000).
Rahman et al., "Synthesis and biological studies of thiohydantoins." Bangladesh J Bio Sci. 5(1):28-30 (1976).
Raymond et al., "Conditional probability: A new fusion method for merging disparate virtual screening results," J. Chem. Inf. Comput. Sci. 44: 601-609 (2004).
Robba et al., "Chimie organique. synthese de tetrahydro-5.6.7.8 benzo-(1)thieno-[2.3-d] pyrimidines," CR Acad Sc Paris. 276:93-5 (1973).
Sane et al., "Caspase inhibition in camptothecin-treated U-937 cells is coupled with a shift from apoptosis to transient G1 arrest followed by necrotic cell death." Cancer Res. 59(15):3565-9 (1999).

Selic et al., "A simple stereoselective synthesis of aplysinopsin analogs." Hely Chim Acta. 83(10):2802-11 (2000).
Selkoe, "Translating cell biology into therapeutic advances in alzheimer's disease." Nature. 399(6738 Suppl):A23-A31 (1999).
Silvestri et al., "Simple, potent, and selective pyrrole inhibitors of monoamine oxidase types A and B," J. Med. Chem. 46: 917-920 (2003).
Sim, M. and Ganesan, A., Solution-Phase Synthesis of a Combinatorial Thiohydantoin Library, J. Org. Chem., 62:3230-3235 (1997).
Souillac et al., Characterization of Delivery Systems, Differential Scanning Calorimetry. Encyclopedia of Controlled Drug Delivery. John Wiley & Sons, 212-27 (1999).
Suzuki et al., "Proton nuclear magnetic resonance studies on methylthiohydantoins, thiohydantoins, and hydantoins of amino acids." Can J Biochem. 55(5):521-7 (1977).
Swan, "Thiohydantoins. I. Preparation of some 2-thiohydantoins from amino acids and acylamino acids," Australian J. Sci Res. A5:711-20 (1952) (Abstract only).
Syntichaki et al., "Death by necrosis. Uncontrollable catastrophe, or is there order behind the chaos?" EMBO Rep. 3(7):604-9 (2002).
Szollosy et al., "Fused heterocycles. Part 4. Synthesis and stereochemistry of hexahydrobenzo[6,71Cyclohepta[1,2-clPvrazoles." J Chem Soc Perkin Trans. 2:489-93 (1991).
Takahashi et al., "Antimutagenic properties of 3,5-disubstituted 2-thiohydantoins." J Agric Food Chem. 46:5037-42 (1998).
Talanian et al., "Caspases as targets for anti-inflammatory and anti-apoptotic drug discovery," J Med Chem. 43(18):3351-71 (2000).
Teng et al., "Structure-activity relationship and liver microsome stability studies of pyrrole necroptosis inhibitors," Bioorg Med Chem Lett. 18(11):3219-23 (2008).
Teng et al., "Structure-activity relationship study of [1,2,3]thiadiazole necroptosis inhibitors," Bioorg. Med. Chem. Lett. 17: 6836-6840 (2007).
Thomas et al., "Synthesis and platelet aggregation inhibitory activity of 4,5-bis(substituted)-1,2,3-thiadiazoles," J Med Chem. 28(4):442-6 (1985).
Toniolo, "Optical rotatory properties of methylisothiocyanate-amino acid adducts." Tetrahedron. 26:5479-88 (1970).
Toriba, a. et al., Development of an Amino Acid Sequence and D/L-Configuration Determination Method of Peptide with a New Fluorescence Edman Reagent, 7-Methylthio-4-(2,1,3-benzoxadiazoly1) Isothiocyanate, Anal. Chem., 72:732-739 (2000).
Vanden Berghe et al., "Necroptosis, necrosis, and secondary necrosis converge on similar cellular disintearation features," Cell Death and Differ. 17(6): 922-30 (2010).
Vercammen et al., "Dual signaling of the fas receptor: initiation of both apoptotic and necrotic cell death pathways." J Exp Med. 188(5):919-30 (1998).
Vercammen et al., "Inhibition of caspases increases the sensitivity of L929 cells to necrosis mediated by tumor necrosis factor." J Exp Med. 187(9):1477-85 (1998).
Vila et al., "Engineered modeling and the secrets of Parkinson's disease," Trends Neurosci. 24(11 Suppl):549-55 (2001).
Vippaaunta et al., "Crystalline solids," Adv Drua Deliv Rev. 48(1):3-26 (2001).
Wang et al., "Structure-activity relationship analysis of a novel necroptosis inhibitor, necrostatin-5," Bioorg Med Chem Lett. 17(5):1455-65 (2007).
Wang, X. et al., Synthesis of 2-Thiohydantoins as Somatostatin Subtype 4 Receptor Ligands, Letters in Drug Design & Discovery, 9:655-662 (2012).
Waterfield et al., "Amino acid sequence analysis with methyl isothiocyanate. Resolution of the methylthiohydantoins by gas-liquid partition chromatography." Biochemistry. 9(4):832-9 (1970).
Woo, "Gas chromatographic determination of methylthiohydantoin amino acid as N(O)-Butyldimethylsilyl derivatives in amino acid sequencing with methylisothiocyanate." J Korean Agric Chem Soc. 35(2):132-8 (1992).
Written Opinion for PCT/US2014/029658, 6 pages. (Aug. 1, 2014).

(56) References Cited

OTHER PUBLICATIONS

Written Opinion of the International Search Authority for International Application No. PCT/US08/09793, mailed Nov. 3, 2008 (7 pages).
Written Opinion of the International Searching Authority for International Application No. PCT/US2004/028270, mailed Jan. 18, 2006 (7 pages).
Yamaguchi et al., "3,4-dihydrothienopyrimidines. II. 1) Synthesis and sodium borohydride reduction of 2-substituted 4-chloro- and 4-unsubstituted-thieno[2,3-d]pyrimidines," Chem Pharm Bull. 30(1):326-32 (1982).
Yuan et al., "Apoptosis in the nervous system." Nature. 407(6805):802-9 (2000).
Zheng et al., "Structure-activity relationship study of a novel necroptosis inhibitor, necrostatin-7," Bioorg Med Chem Lett. 18(18):4932-5 (2008).

* cited by examiner

SUBSTITUTED INDOLES AND PYRROLES AS RIP KINASE INHIBITORS

CROSS-REFERENCE TO RELATED APPLICATION

This application is a utility application which claims benefit of U.S. Provisional Application No. 61/792,891, filed on Mar. 15, 2013, which is hereby incorporated by reference.

STATEMENT AS TO FEDERALLY SPONSORED RESEARCH

This invention was made with government support under Grant No. R01GM084205, awarded by the National Institutes of Health. The government has certain rights in this invention.

BACKGROUND OF THE INVENTION

In many diseases, cell death is mediated through apoptotic and/or necrotic pathways. While much is known about the mechanisms of action that control apoptosis, control of necrosis is not as well understood. Understanding the mechanisms regulating both necrosis and apoptosis in cells is essential to being able to treat conditions, such as neurodegenerative diseases, stroke, coronary heart disease, kidney disease, and liver disease. A thorough understanding of necrotic and apoptotic cell death pathways is also crucial to treating AIDS and the conditions associated with AIDS, such as retinal necrosis.

Cell death has traditionally been categorized as either apoptotic or necrotic based on morphological characteristics (Wyllie et al., *Int. Rev. Cytol.* 68: 251 (1980)). These two modes of cell death were also initially thought to occur via regulated (caspase-dependent) and non-regulated processes, respectively. Subsequent studies, however, demonstrate that the underlying cell death mechanisms resulting in these two phenotypes are much more complicated and, under some circumstances, interrelated. Furthermore, conditions that lead to necrosis can occur by either regulated caspase-independent or non-regulated processes.

One regulated caspase-independent cell death pathway with morphological features resembling necrosis, called necroptosis, has been described (Degterev et al., *Nat. Chem. Biol.* 1:112 (2005)). This manner of cell death can be initiated with various stimuli (e.g., TNF-α and Fas ligand) and in an array of cell types (e.g., monocytes, fibroblasts, lymphocytes, macrophages, epithelial cells and neurons). Necroptosis may represent a significant contributor to and, in some cases, predominant mode of cellular demise under pathological conditions involving excessive cell stress, rapid energy loss, and massive oxidative species generation, where the highly energy-dependent apoptosis process is not operative.

The identification and optimization of low molecular weight molecules capable of inhibiting necroptosis will assist in elucidating its role in disease patho-physiology and can provide compounds (i.e., necrostatins) for anti-necroptosis therapeutics. The discovery of compounds that prevent caspase-independent cell death (e.g., necrosis or necroptosis) would also provide useful therapeutic agents for treating or preventing conditions in which necrosis occurs. These compounds and methods would be particularly useful for the treatment of neurodegenerative diseases, ischemic brain and heart injuries, and head trauma.

SUMMARY OF THE INVENTION

The invention features new compounds, pharmaceutical compositions, kits, and methods for treating a condition in which necrosis or necroptosis is likely to play a substantial role, or those in which RIP1 and/or RIP3 protein is a contributing factor.

In a first aspect, the invention features a compound of the formula

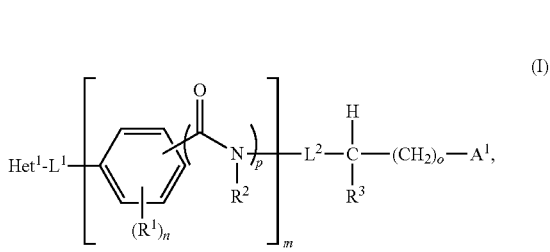

or any pharmaceutically acceptable salt thereof, or stereoisomer thereof, where m is 0 or 1;

$Het^1$ is an optionally substituted bicyclic heteroaryl;

$L^1$ is a covalent bond, an optionally substituted C1-C4 alkylene, an optionally substituted C2-C4 alkenylene, an optionally substituted C2-C4 alkynylene, an optionally substituted C3-C6 cycloalkyl, or an optionally substituted three-to-six membered heterocyclyl;

n is an integer between 0-4;

o is 0 or 1;

p is 0 or 1;

each $R^1$, when present, is independently optionally substituted C1-C6 alkyl, optionally substituted C2-C6 alkenyl, optionally substituted C2-C6 alkynyl, optionally substituted C3-C9 cycloalkyl, optionally substituted C5-C9 cycloalkenyl, optionally substituted three- to nine-membered heterocyclyl, optionally substituted C6-C10 aryl, optionally substituted five- to eleven-membered heteroaryl, halogen, —OH, $N_3$, $NO_2$, —$CO_2H$, —NC, or CN; or is a group selected from —OC(=O)$R^{4A}$, —C(=O)$R^{4A}$, —$OR^{4A}$, —$NR^{4A}$C(=O)$R^{4B}$, —C(O)$NR^{4A}R^{4B}$, —$NR^{4A}R^{4B}$, —$CO_2R^{4A}$, —OC(=O)$NR^{4A}R^{4B}$, —$NR^{4A}$C(=O)$OR^{4B}$, —S(=O)$_2OR^{4A}$, —S(=O)$_2NR^{4A}R^{4B}$, —$NR^{4A}$S(=O)$_2R^{4B}$, and —S(=O)$_2R^{4A}$, where each $R^{4A}$ and $R^{4B}$ is independently H or an optionally substituted group that is C1-C6 alkyl, C2-C6 alkenyl, C2-C6 alkynyl, C3-C9 cycloalkyl, three- to nine-membered heterocyclyl, C6-C10 aryl, or five-to eleven-membered heteroaryl;

$R^2$ is H or optionally substituted C1-C6 alkyl, or $R^2$ combines with $R^3$ to form an optionally substituted C1-C3 alkylene moiety;

$L^2$ is a covalent bond or an optionally substituted C1-C4 alkylene;

$R^3$ is H or optionally substituted C1-C6 alkyl, or $R^3$ combines with $R^2$ to form an optionally substituted C1-C3 alkylene moiety;

$A^1$ is a fragment that is

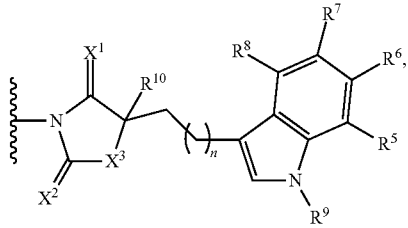
(a)

where
- each $X^1$ and $X^2$ is, independently, O or S;
- $X^3$ is O or $NR^{11}$;
- n is 0 or 1;
- each of $R^5$, $R^6$, $R^7$, and $R^8$ is, independently, H, OH, optionally substituted C1-C6 alkyl, optionally substituted C1-C6 alkoxy, halogen, $N(R^{12})_2$, $CO_2R^{12}$, $NO_2$, $NHC(O)R^{12}$, optionally substituted aryl, optionally substituted heteroaryl, or piperizine;
- $R^9$ is H or optionally substituted C1-C6 alkyl;
- $R^{10}$ is H or optionally substituted C1-C6 alkyl;
- $R^{11}$ is H or optionally substituted C1-C6 alkyl;
- $R^{12}$ represents H, optionally substituted C1-C6 alkyl, optionally substituted aryl, optionally substituted alkaryl, optionally substituted C2-C6 alkenyl, optionally substituted C2-C6 alkynyl, or optionally substituted heteroaryl or

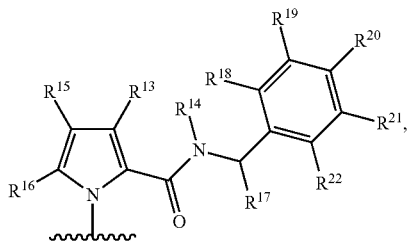
(b)

where
- $R^{13}$ is selected from H, halogen, optionally substituted C1-C6 alkyl, optionally substituted C1-C6 cycloalkyl, or optionally substituted aryl;
- $R^{14}$ is selected from H or optionally substituted C1-C6 alkyl;
- $R^{15}$ and $R^{16}$ are selected, independently, from hydrogen, halogen, carboxamido, nitro, and cyano;
- $R^{17}$ is, independently, selected from H, optionally substituted aryl, or optionally substituted C1-C6 alkyl;
- each of $R^{18}$, $R^{19}$, $R^{20}$, $R^{21}$, and $R^{22}$ is selected, independently, from H, optionally substituted C1-C6 alkyl, halogen, optionally substituted amino, optionally substituted carboxamido, optionally substituted C1-C6 alkoxy, nitro, and cyano.

In some embodiments, the compound has a structure according to one of the following formulas:

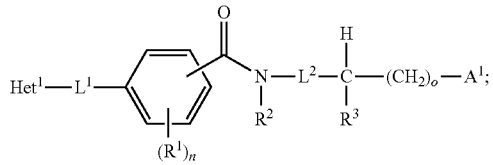
(II)

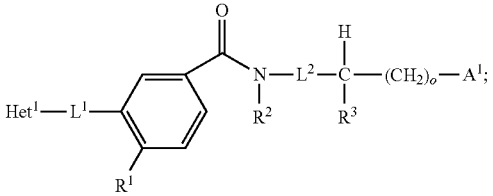
(III)

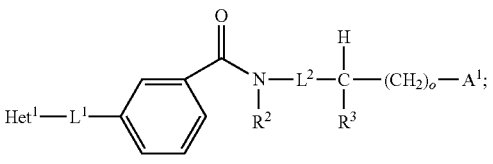
(IV)

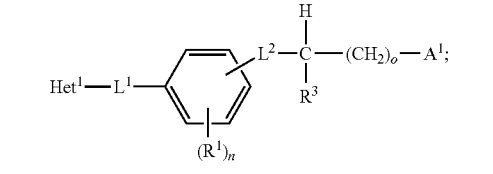
(V)

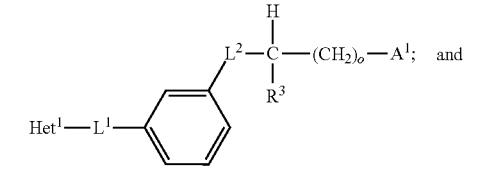
(VI); and

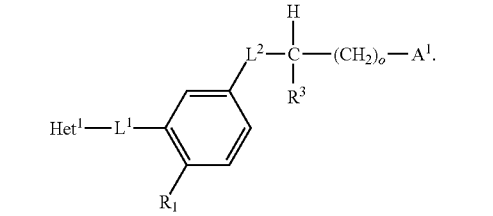
(VII).

In some embodiments, $Het^1$ is an optionally substituted indole, azaindole, indazole, imidazopyridine, imidazopyrimidine, pyrrolopyrimidine, pyrrolopyridine, pyrazolopyridine, pyrazolopyrimidine, quinoline, or isoquinoline group. In further embodiments, $Het^1$ is unsubstituted or includes 1 or 2 substituents selected from halogen, CN, $NO_2$, optionally substituted C1-C6 alkyl, or optionally substituted C1-C6 alkoxy.

In other embodiments, $Het^1$ is selected from the group consisting of

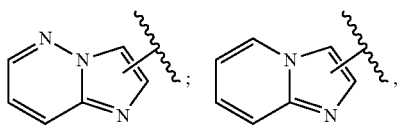

-continued

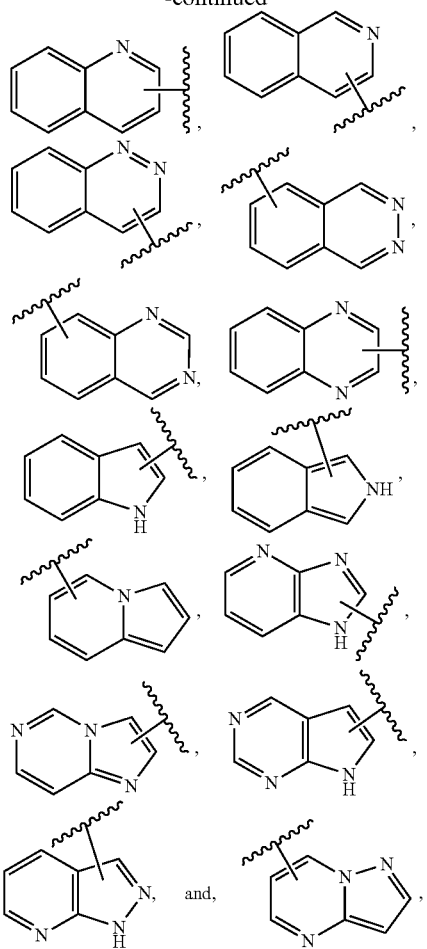

or any isomer thereof. A covalent attachment to $Het^1$ can occur at any atom having a hydrogen group that can be replaced with the covalent bond. In some embodiments, any of these heterocycles may be substituted by the replacement or one or more hydrogen groups (e.g., the replacement of one or two hydrogen groups) with a group that is selected, independently, from optionally substituted C1-C6 alkyl, halogen, optionally substituted amino, optionally substituted carboxamido, optionally substituted C1-C6 alkoxy, nitro, and cyano.

In certain embodiments, $Het^1$ is

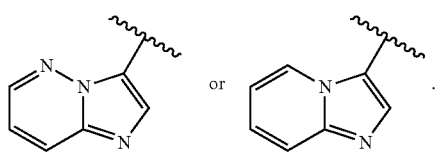 [SMILES: *c1cnc2cccnn12 ; *c1cnc2ccccn12]

In other embodiments, $L^1$ is optionally substituted C1-C2 alkylene, optionally substituted C2 alkenylene, C2 alkynylene, or optionally substituted C3-C6 cycloalkyl (e.g., $L^1$ is —$CH_2CH_2$—, —C≡C—, —CH=CH—, or unsubstituted cyclopropyl).

In certain embodiments, each $R^1$, when present, is independently selected from halogen, optionally substituted C1-C6 alkyl, optionally substituted C1-C6 alkoxy, or CN, In still other embodiments, n is 0 or 1.

In some embodiments, o is 0 or 1.

In certain embodiments, the compound has a structure according to one of the following formulas,

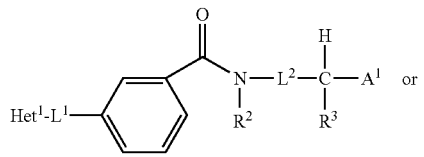

(VIII)

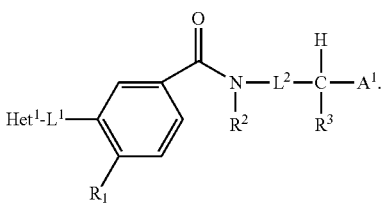

(IX)

In some embodiments, $R^1$, when present, is optionally substituted C1-C2 alkyl.

In still other embodiments, $L^2$ is optionally substituted C1-C2 alkylene (e.g., $L^2$ is $CH_2$ or $CH_2CH_2$).

In other embodiments, $R^2$ is H.

In certain embodiments, $R^3$ is H.

In further embodiments, $R^2$ and $R^3$ combine to form an optionally substituted C1-C3 alkylene moiety (e.g., $R^2$ and $R^3$ combine to form $CH_2CH_2$).

In further embodiments, the compound has a structure according to one of the following formulas:

(a)

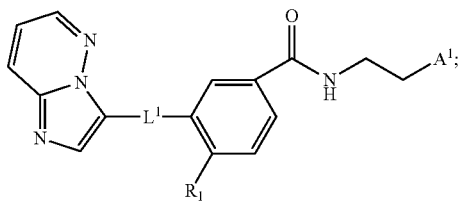

(X)

(b)

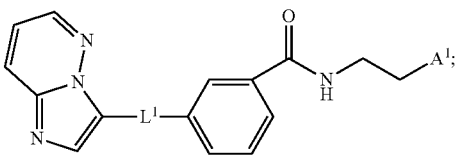

(XI)

(c)

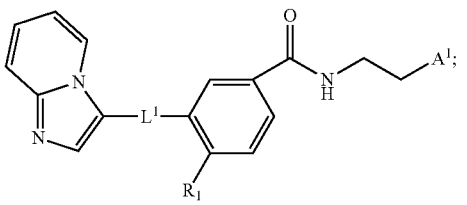

(XII)

(d)

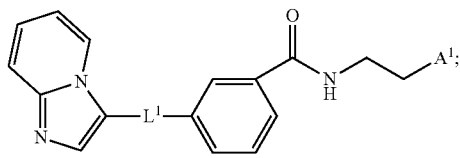
(XIII)

(e)

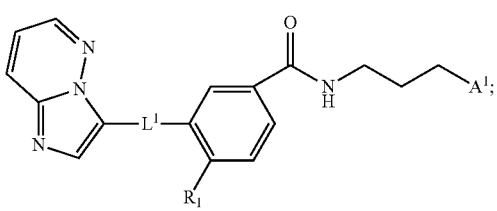
(XIV)

(f)

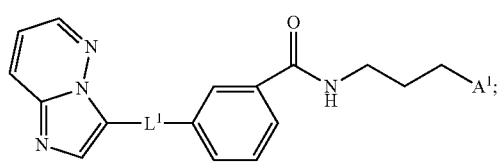
(XV)

(g)

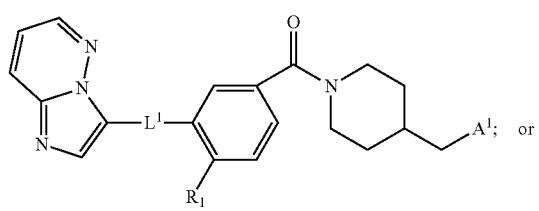
(XVI)

(h)

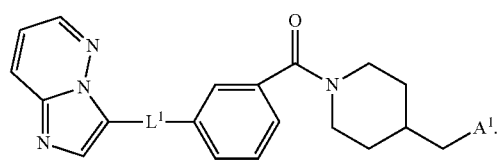
(XVII)

In some embodiments, $L^1$ is —CH$_2$CH$_2$—, —C≡C—, —CH=CH—, or unsubstituted cyclopropyl.

In other embodiments, $R^1$, when present, is optionally substituted C1-C6 alkyl (e.g., CH$_3$).

In some embodiments, the compound has a structure according to one of the following formulas, (a)

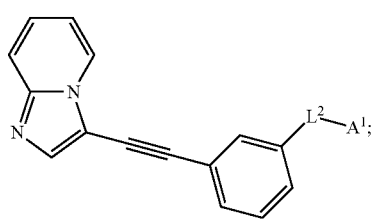
(XVIII)

(b)

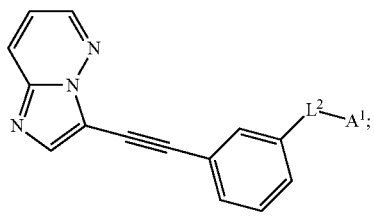
(XIX)

(c)

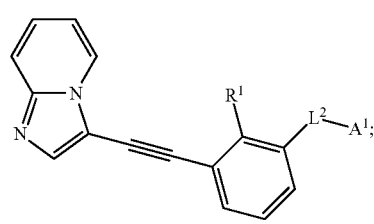
(XX)

(d)

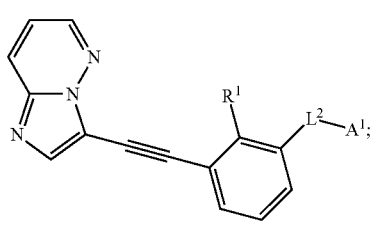
(XXI)

In some embodiments, $R^1$, when present, is optionally substituted C1-C6 alkyl (e.g., $R^1$ is CH$_3$).

In other embodiments, $L^2$ is optionally substituted C1-C4 alkylene.

In certain embodiments, m is 0 and said compound has the following structure,

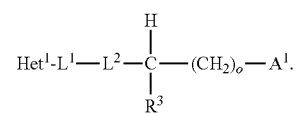
(XXII)

In further embodiments, $L^1$ is C2 alkynyl.

In certain embodiments, o is 0.

In still other embodiments, $L^2$ is optionally substituted C1alkylene (e.g., CH$_2$).

In some embodiments, $R^3$ is H.

In certain embodiments, $A^1$ is

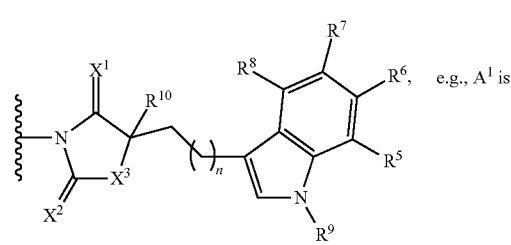
e.g., $A^1$ is

-continued

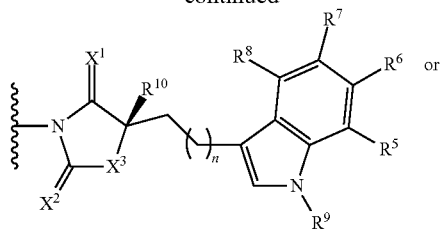

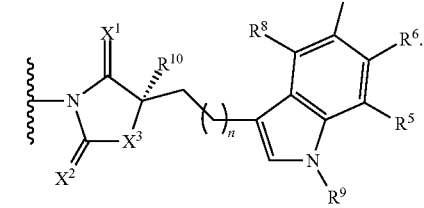

In some embodiments, n is 0.
In other embodiments, $R^9$ is H or $CH_3$.
In still other embodiments, $R^{10}$ is H.
In particular embodiments, $X^1$ and $X^2$ are both O.
In certain embodiments, $X^3$ is O.
In some embodiments, $X^3$ is $NR^{11}$.
In other embodiments, $R^{11}$ is H.
In still other embodiments, $R^6$, $R^7$, and $R^8$ are each H.
In further embodiments, $R^5$ is H, halogen, OH, optionally substituted C1-C3 alkyl, or optionally substituted C1-C3 alkoxy (e.g., $R^5$ is H, Cl, OH, $CH_3$, or $OCH_3$).
In some embodiments, $A^1$ is

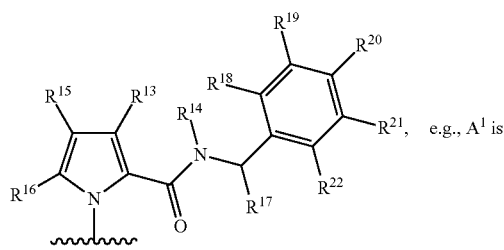

e.g., $A^1$ is

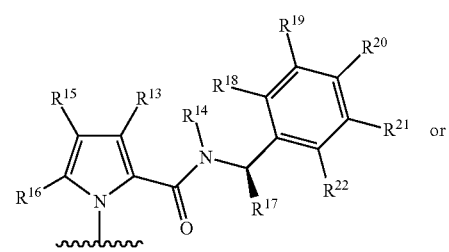

In some embodiments, $R^{13}$ and $R^{15}$ are both H,
In other embodiments, $R^{16}$ is CN.
In further embodiments, $R^{14}$ is H or $CH_3$.
In still other embodiments, $R^{17}$ is optionally substituted C1-C3 alkyl (e.g., $R^{17}$ is $CH_3$).
In certain embodiments, $R^{19}$, $R^{20}$, and $R^{21}$ are each H.
In some embodiments, $R^{18}$ and $R^{22}$ are each, independently, halogen (e.g., $R^{18}$ is fluoro and $R^{22}$ is chloro).
In some embodiments, $A^1$ is

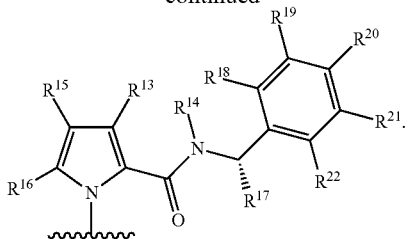

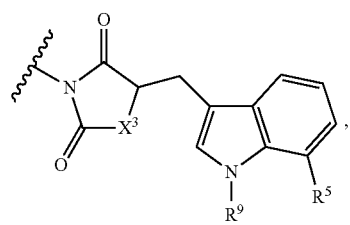

where $X^3$ is O or NH, $R^9$ is H or optionally substituted C1 alkyl, and $R^5$ is H, halogen, OH, optionally substituted C1-C3 alkyl, or optionally substituted C1-C3 alkoxy (e.g., $R^5$ is H, Cl, OH, $CH_3$, or $OCH_3$).
In other embodiments, $A^1$ is

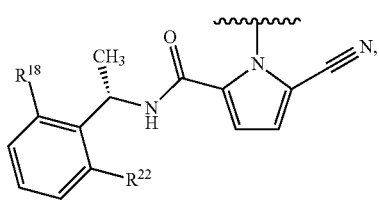

where each of $R^{18}$ and $R^{22}$ is, independently, H, F, or Cl (e.g., $R^{18}$ is F and $R^{22}$ is Cl, or $R^{18}$ is F and $R^{22}$ is H).
In other embodiments, the compound is selected from the group consisting of:

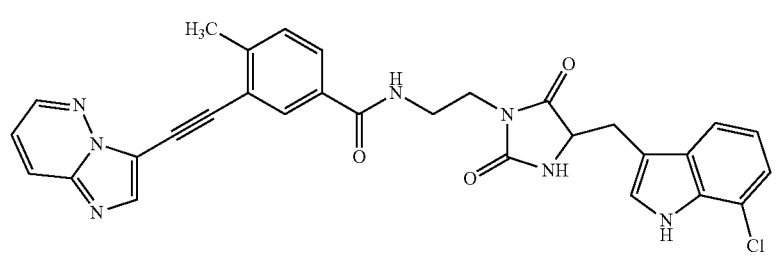

(1)

-continued
(2)
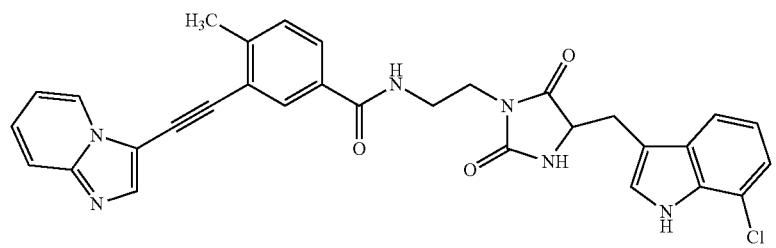
(3)
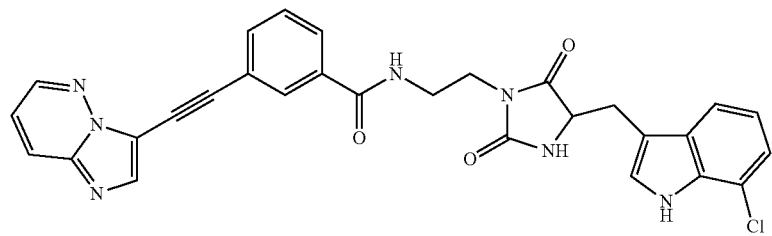
(4)
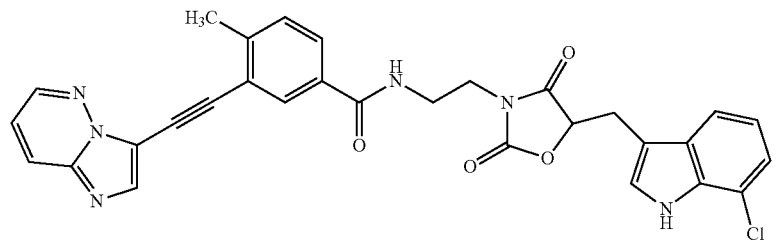
(5)
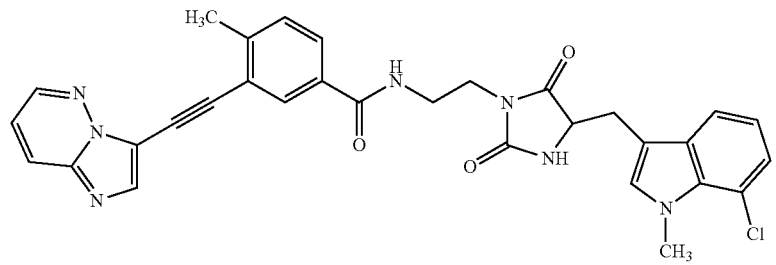
(6)
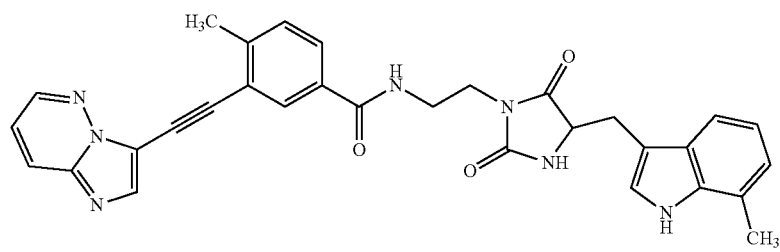
(7)
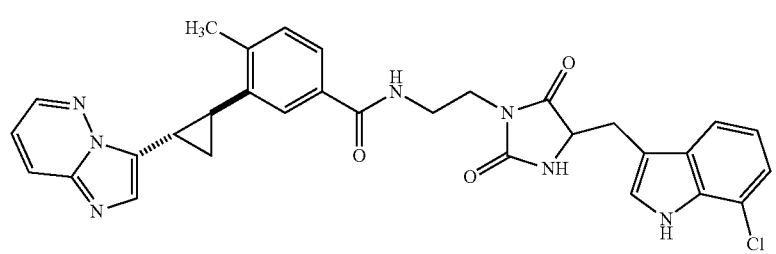

-continued
(8)
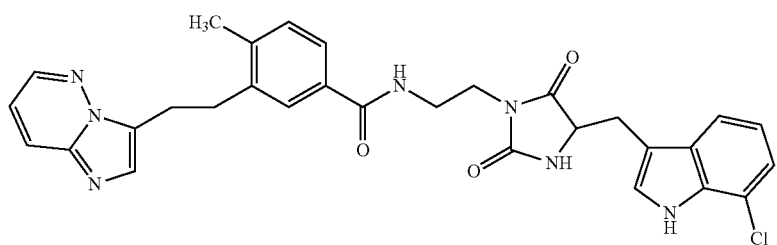
(9)
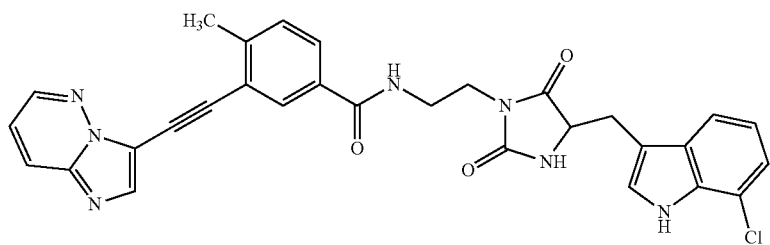
(10)
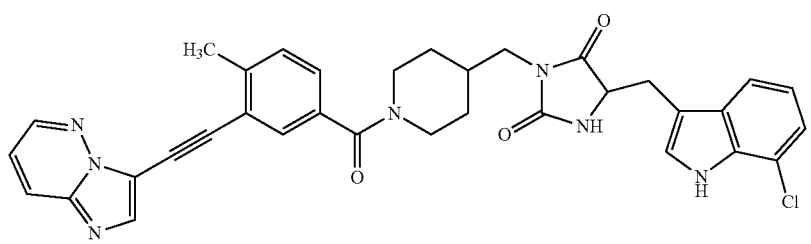
(11)
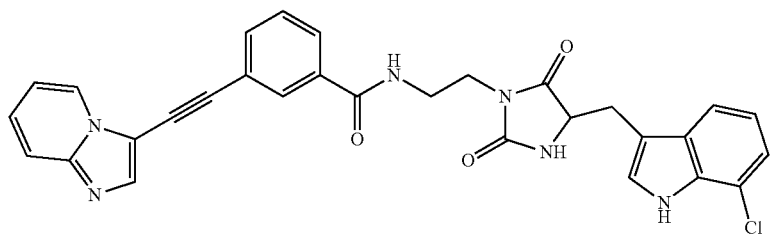
(12)
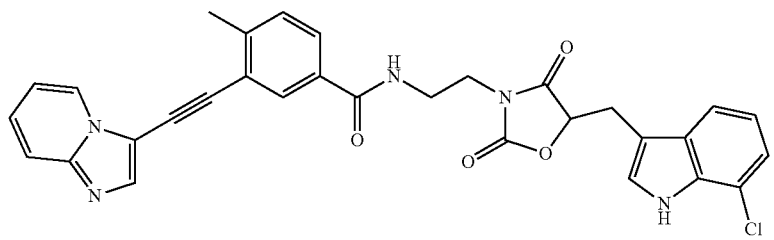
(13)
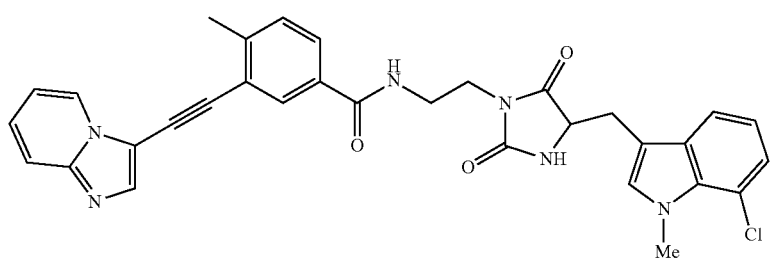

-continued
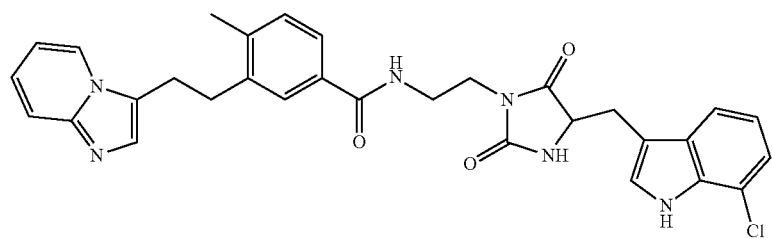
(14)
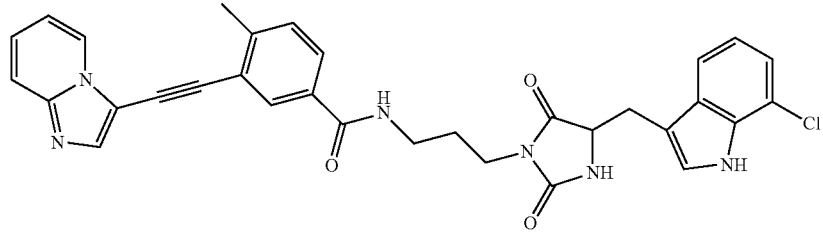
(15)
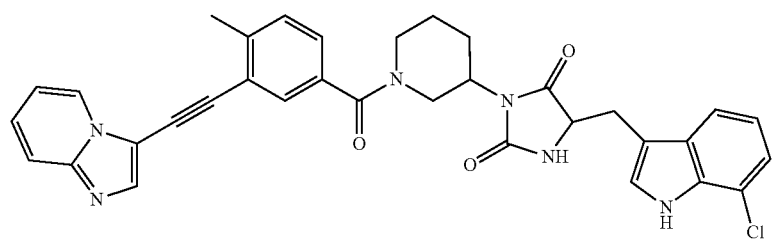
(16)
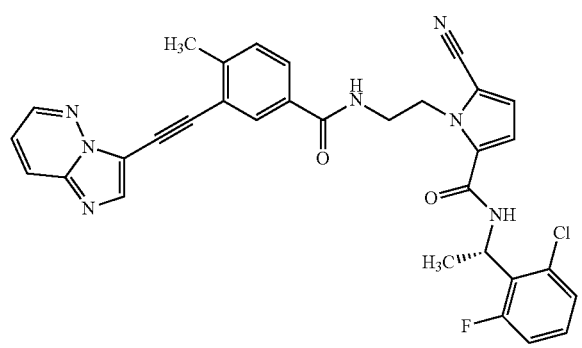
(17)
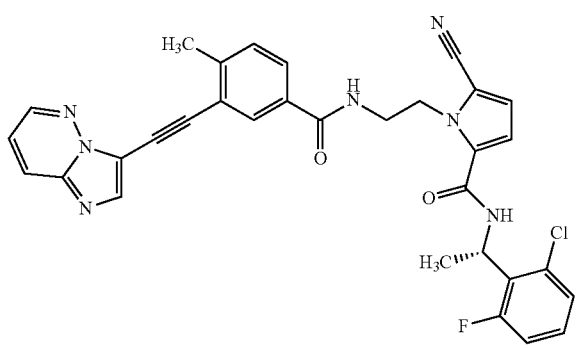
(18)
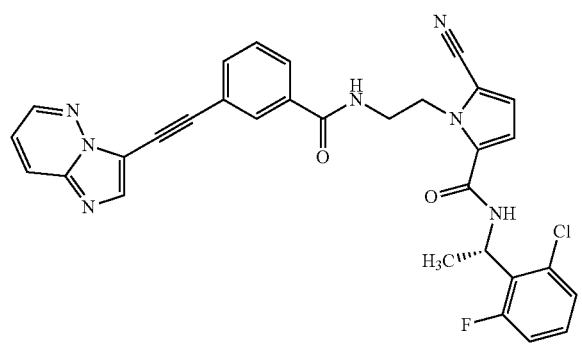
(19)
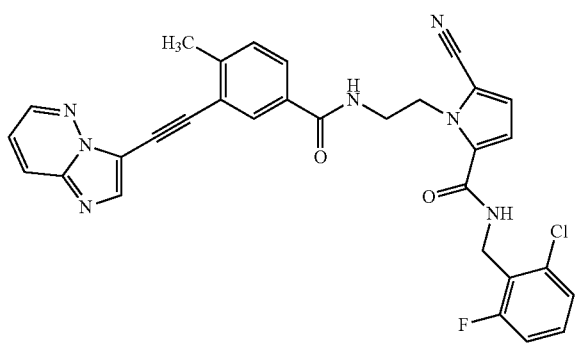
(20)

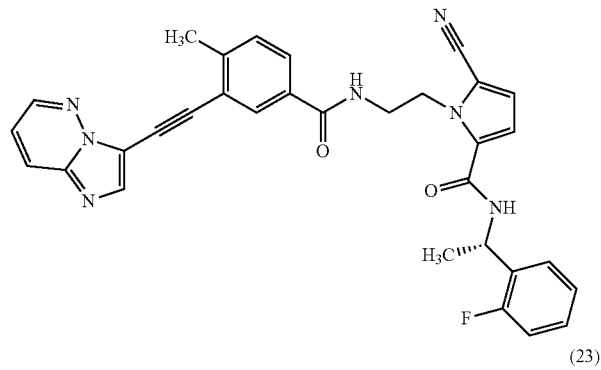
(21)

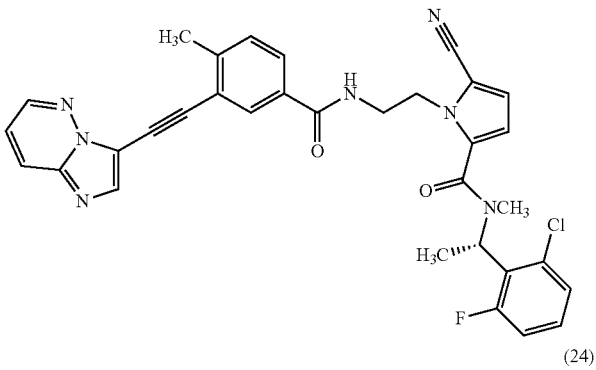
(22)

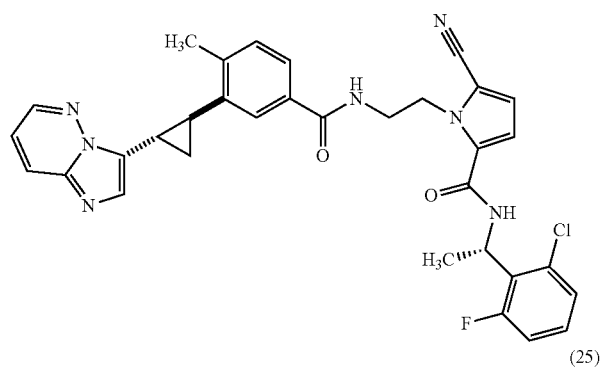
(23)

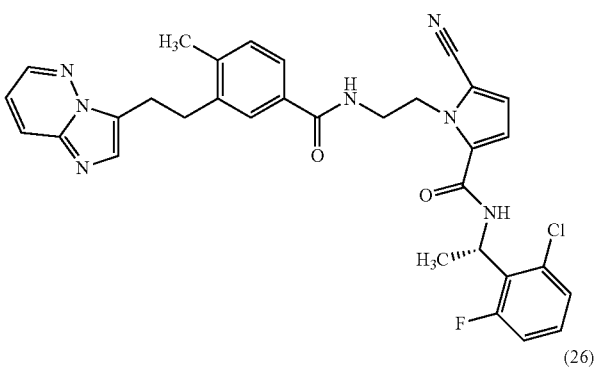
(24)

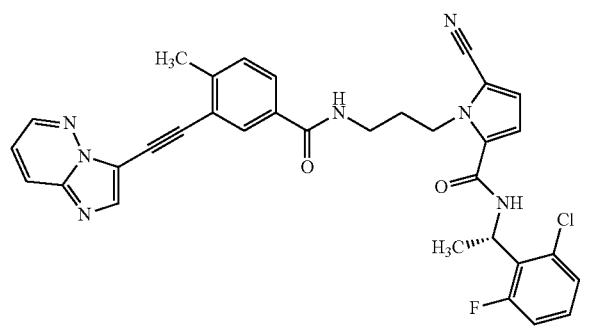
(25)

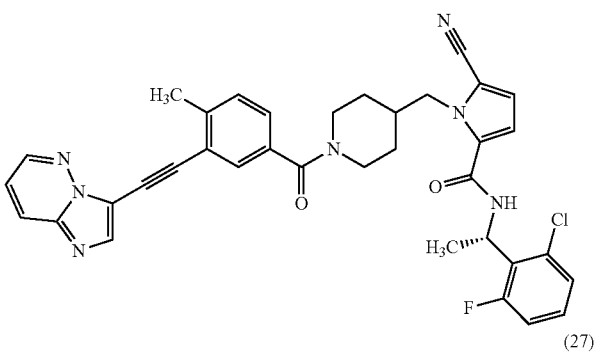
(26)

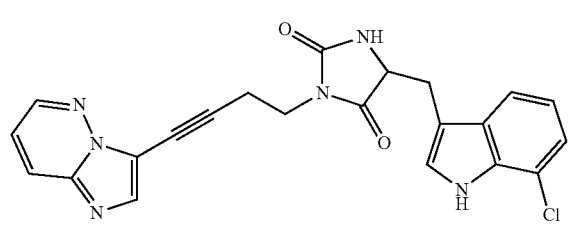
(27)

In some embodiments, the invention also features the pharmaceutically acceptable salt of any of the compounds (e.g., a compound according to any of formulas (I)-(XXVI) or any of compounds (1)-(27)) described herein, or the stereoisomer of any of the compounds described herein.

In a second aspect, the invention features a pharmaceutical composition that includes a pharmaceutically acceptable excipient and any of the compounds described herein (e.g., a compound according to any of formulas (I)-(XXVI) or any of compounds (1)-(27)), or any pharmaceutically acceptable salt thereof, or stereoisomer thereof.

In a third aspect, the invention features method of treating a condition in a subject, where the method includes the step of contacting any of the compounds (e.g., a compound according to any of formulas (I)-(XXVI) or any of compounds (1)-(27)) or compositions described herein, or any pharmaceutically acceptable salt thereof, or stereoisomer thereof, to the subject in a dosage sufficient to decrease necroptosis, and where the condition is one in which necroptosis is likely to play a substantial role.

In another aspect, the invention features a method of treating a condition in a subject, said method comprising the step of contacting any of the compounds (e.g., a compound according to any of formulas (I)-(XXVI) or any of compounds (1)-(27)) or compositions described herein, or any pharmaceutically acceptable salt thereof, or stereoisomer thereof, to said subject in a dosage sufficient to modulate RIP1 and/or RIP3 activity, and wherein said condition is one in which RIP1 and/or RIP3 protein is a contributing factor.

For example, the methods of the invention can include administering to a subject any of the compounds (e.g., a compound according to any of formulas (I)-(XXVI) or any of compounds (1)-(27)) or compositions described herein, or any pharmaceutically acceptable salt thereof, or stereoisomer thereof.

In some embodiments, the condition is a neurodegenerative disease of the central or peripheral nervous system, the result of retinal neuronal cell death, the result of cell death of cardiac muscle, the result of cell death of cells of the immune system; stroke, liver disease, pancreatic disease, the result of cell death associated with renal failure; heart, mesenteric, retinal, hepatic or brain ischemic injury, ischemic injury during organ storage, head trauma, septic shock, coronary heart disease, cardiomyopathy, myocardial infarction, bone avascular necrosis, sickle cell disease, muscle wasting, gastrointestinal disease, tuberculosis, diabetes, alteration of blood vessels, muscular dystrophy, graft-versus-host disease, viral infection, Crohn's disease, ulcerative colitis, asthma, atherosclerosis, a chronic or acute inflammatory condition, pain, or any condition in which alteration in cell proliferation, differentiation or intracellular signaling is a causative factor, or any condition where RIP1 and/or RIP3 protein is a contributing factor.

In still other embodiments, the condition is a neurodegenerative disease of the central or peripheral nervous system.

In certain embodiments, the condition is hepatic or brain ischemic injury, or ischemic injury during organ storage, head trauma, septic shock, or coronary heart disease.

In some embodiments, the condition is stroke.

In other embodiments, the condition is myocardial infarction.

In some embodiments, the condition is pain (e.g., inflammatory pain, diabetic pain, pain associated with a burn, or pain associated with trauma).

In other embodiments, the condition is atherosclerosis.

In still other embodiments, the condition is a chronic or acute inflammatory condition (e.g., rheumatoid arthritis, psoriasis, or Stevens-Johnson syndrome).

In a fourth aspect, the invention features a method of decreasing necroptosis including contacting a cell with any of the compounds or compositions described herein, or any pharmaceutically acceptable salt thereof, or stereoisomer thereof.

In a fifth aspect, the invention features a kit that includes
(a) a pharmaceutically acceptable composition that includes any of the compounds or compositions described herein (e.g., a compound according to any of formulas (I)-(XXVI) or any of compounds (1)-(27)), or any pharmaceutically acceptable salt thereof, or stereoisomer thereof; and
(b) instructions for the use of the pharmaceutical composition of (a) to treat a condition in a subject.

In a fifth aspect, the invention features a kit that includes:
(a) a pharmaceutically acceptable composition that includes any of the compositions or compounds described herein, or any pharmaceutically acceptable salt thereof, or stereoisomer thereof; and
(c) instructions for the use of the pharmaceutical composition of (a) to treat a condition in a subject.

By "$C_{1-4}$ alkaryl" is meant a $C_{1-4}$ alkyl group having an optionally substituted aryl or an optionally substituted heteroaryl located at any position of the carbon chain. The $C_{1-4}$ alkyl group may be linear or branched and may also be substituted with, for example, 1, 2, 3, 4, or 5 additional substituents as described herein.

By "alkoxy" is meant a group having the structure —O(optionally substituted C1-C6 alkyl), where the optionally substituted C1-C6 alkyl may be branched, linear, or cyclic. The C1-C6 alkyl may be substituted or unsubstituted. A substituted C1-C6 alkyl can have, for example, 1, 2, 3, 4, 5, or 6 substituents located at any position. Exemplary alkoxy groups include, but are not limited to, methoxy, ethoxy, propoxy, isopropoxy, tert-butoxy, and the like.

By "C2-C6 alkenyl" or "alkenyl" is meant an optionally substituted unsaturated C2-C6 hydrocarbon group having one or more carbon-carbon double bonds. Exemplary C2-C6 alkenyl groups include, but are not limited to —CH=CH (ethenyl), propenyl, 2-propenyl, 2-methyl-1-propenyl, 1-butenyl, 2-butenyl, and the like. A C2-C6 alkenyl may be linear or branched and may be unsubstituted or substituted. A substituted C2-C6 alkenyl may have, for example, 1, 2, 3, 4, 5, or 6 substituents located at any position.

By "C1-C6 alkyl" or "alkyl" is meant an optionally substituted C1-C6 saturated hydrocarbon group. An alkyl group may be linear, branched, or cyclic ("cycloalkyl"). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Substituted alkyl groups may have, for example, 1, 2, 3, 4, 5, or 6 substituents located at any position. Exemplary substituted alkyl groups include, but are not limited to, optionally substituted $C_{1-4}$ alkaryl groups.

By "C2-C6 alkynyl" or "alkynyl" is meant an optionally substituted unsaturated C2-C6 hydrocarbon group having one or more carbon-carbon triple bonds. Exemplary C2-C6 alkynyl groups include, but are not limited to ethynyl, 1-propynyl, and the like As used herein, the terms "alkylene," "alkenylene," and "alkynylene," or the prefix "alk" refer to divalent or trivalent groups having a specified size, typically C1-C2, C1-C3, C1-C4, C1-C6, or C1-C8 for the saturated groups (e.g., alkylene or alk) and C2-C3, C2-C4, C2-C6, or C2-C8 for the unsaturated groups (e.g., alkenylene or alkynylene). They include straight-chain, branched-chain, and cyclic forms as well as combinations of these, containing only C and H when unsubstituted. Because they are divalent, they can link together two parts of a molecule, as exemplified by X in the compounds described herein. Examples are methylene, ethylene, propylene, cyclopropan-1,1-diyl, ethylidene, 2-butene-1,4-diyl, and the like. These groups can be substituted by the groups typically suitable as substituents for alkyl, alkenyl and alkynyl groups as set forth herein. Thus C=O is a C1 alkylene that is substituted by =O, for example. For example, the term "alkaryl," as used herein, represents an aryl group, as defined herein, attached to the parent molecular group through an alkylene group, as defined herein, and the term "alkheteroaryl" refers to a heteroaryl group, as defined herein, attached to the parent molecular group through an alkylene group, as defined herein. The alkylene and the aryl or heteroaryl group are each optionally substituted as described herein.

By "amino" is meant a group having a structure —NR'R", where each R' and R" is selected, independently, from H, optionally substituted C1-C6 alkyl, optionally substituted cycloalkyl, optionally substituted heterocyclyl, optionally substituted aryl, optionally substituted heteroaryl, or R' and R" combine to form an optionally substituted heterocyclyl. When R' is not H or R" is not H, R' and R" may be unsubstituted or substituted with, for example, 1, 2, 3, 4, 5, or 6 substituents.

By "aryl" is meant is an optionally substituted $C_6$-$C_{14}$ cyclic group with $[4n+2]\pi$ electrons in conjugation and where n is 1, 2, or 3. Non-limiting examples of aryls include heteroaryls and, for example, benzene, naphthalene, anthracene, and phenanthrene. Aryls also include bi- and tri-cyclic ring systems in which a non-aromatic saturated or partially unsaturated carbocyclic ring (e.g., a cycloalkyl or cycloalkenyl) is fused to an aromatic ring such as benzene or naphthalene. Exemplary aryls fused to a non-aromatic ring include indanyl, tetrahydronaphthyl. Any aryls as defined herein may be unsubstituted or substituted. A substituted aryl may be optionally substituted with, for example, 1, 2, 3, 4, 5, or 6 substituents located at any position of the ring.

By "aryloxy" is meant a group having the structure —O(optionally substituted aryl), where aryl is as defined herein.

By "azido" is meant a group having the structure —$N_3$.

By "carbamate" or "carbamoyl" is meant a group having the structure —OCONR'R" or —NR'$CO_2$R", where each R' and R" is selected, independently, from H, optionally substituted C1-C6 alkyl, optionally substituted cycloalkyl, optionally substituted heterocyclyl, optionally substituted aryl, optionally substituted heteroaryl, or R' and R" combine to form an optionally substituted heterocyclyl. When R' is not H or R" is not H, R' and R" may be unsubstituted or substituted with, for example, 1, 2, 3, 4, 5, or 6 substituents.

By "carbonate" is meant a group having a the structure —$OCO_2$R', where R' is selected from H, optionally substituted C1-C6 alkyl, optionally substituted cycloalkyl, optionally substituted heterocyclyl, optionally substituted aryl, or optionally substituted heteroaryl. When R' is not H, R may be unsubstituted or substituted with, for example, 1, 2, 3, 4, 5, or 6 substituents.

By "carboxamido" or "amido" is meant a group having the structure —CONR'R" or —NR'C(=O)R", where each R' and R" is selected, independently, from H, optionally substituted C1-C6 alkyl, optionally substituted cycloalkyl, optionally substituted heterocyclyl, optionally substituted aryl, optionally substituted heteroaryl, or R' and R" combine to form an optionally substituted heterocyclyl. When R' is not H or R" is not H, R' and R" may be unsubstituted or substituted with, for example, 1, 2, 3, 4, 5, or 6 substituents.

By "carboxylic group" is meant a group having the structure —$CO_2$R', where R' is selected from H, optionally substituted C1-C6 alkyl, optionally substituted cycloalkyl, optionally substituted heterocyclyl, optionally substituted aryl, or optionally substituted heteroaryl. When R' is not H, R may be unsubstituted or substituted with, for example, 1, 2, 3, 4, 5, or 6 substituents.

By "cyano" is meant a group having the structure —CN.

By "$C_3$-10 cycloalkyl" or "cycloalkyl" is meant an optionally substituted, saturated or partially unsaturated 3- to 10-membered monocyclic or polycyclic (e.g., bicyclic, or tricyclic) hydrocarbon ring system. Where a cycloalkyl is polycyclic, the constituent cycloalkyl rings may be fused together, form a spirocyclic structure, or the polycyclic cycloalkyl may be a bridged cycloalkyl (e.g., adamantyl or norbonanyl). Exemplary cycloalkyls induce cyclopropyl, cyclobutyl, cyclopentyl, cyclohexyl, and cycloheptyl. Cycloalkyls may be unsubstituted or substituted. A substituted cycloalkyl can have, for example, 1, 2, 3, 4, 5, or 6 substituents.

By "cycloalkenyl" is meant a non-aromatic, optionally substituted 3- to 10-membered monocyclic or bicyclic hydrocarbon ring system having at least one carbon-carbon double bound. For example, a cycloalkenyl may have 1 or 2 carbon-carbon double bonds. Cycloalkenyls may be unsubstituted or substituted. A substituted cycloalkenyl can have, for example, 1, 2, 3, 4, 5, or 6 substituents. Exemplary cycloalkenyls include, but are not limited to, cyclopropenyl, cyclobutenyl, cyclopentenyl, cyclopentadienyl, cyclohexenyl, 1,3-cyclohexadienyl, 1,4-cyclohexadienyl, and the like.

By "effective amount" or "therapeutically effective amount" of an agent, as used herein, is that amount sufficient to effect beneficial or desired results, such as clinical results, and, as such, an effective amount depends upon the context in which it is being applied. For example, in the context of administering an agent that is an inhibitor of necroptosis, an effective amount of an agent is, for example, an amount sufficient to achieve a reduction in necroptosis as compared to the response obtained without administration of the agent.

By "ester" is meant a group having a structure selected from —OCOR', where R' is selected from H, optionally substituted C1-C6 alkyl, optionally substituted cycloalkyl, optionally substituted heterocyclyl, optionally substituted aryl, or optionally substituted heteroaryl. When R' is not H, R may be unsubstituted or substituted with, for example, 1, 2, 3, 4, 5, or 6 substituents.

By "halogen" or "halo" is meant fluorine (—F), chlorine (—Cl), bromine (—Br), or iodine (—I).

By "heteroaryl" is mean an aryl group that contains 1, 2, or 3 heteroatoms in the cyclic framework. Exemplary heteroaryls include, but are not limited to, furan, thiophene, pyrrole, thiadiazole (e.g., 1,2,3-thiadiazole or 1,2,4-thiadiazole), oxadiazole (e.g., 1,2,3-oxadiazole or 1,2,5-oxadiazole), oxazole, benzoxazole, isoxazole, isothiazole, pyrazole, thiazole, benzthiazole, triazole (e.g., 1,2,4-triazole or 1,2,3-triazole), benzotriazole, pyridines, pyrimidines, pyrazines, quinoline, isoquinoline, purine, pyrazine, pteridine, triazine (e.g, 1,2,3-triazine, 1,2,4-triazine, or 1,3,5-triazine)indoles, 1,2,4,5-tetrazine, benzo[b]thiophene, benzo[c]thiophene, benzofuran, isobenzofuran, and benzimidazole. Still other heteroaryls include indole, azaindole, indazole, imidazopyridine, imidazopyrimidine, pyrrolopyrimidine, pyrrolopyridine, pyrazolopyridine, pyrazolopyrimidine, quinoline, or isoquinoline groups as described herein. Heteroaryls may be unsubstituted or substituted. Substituted heteroaryls can have, for example, 1, 2, 3, 4, 5, or 6 substitutents.

By "heterocyclic" or "heterocyclyl" is meant an optionally substituted non-aromatic, partially unsaturated or fully saturated, 3- to 10-membered ring system, which includes single rings of 3 to 8 atoms in size, and polycyclic ring systems (e.g., bi- and tri-cyclic ring systems) which may include an aryl (e.g., phenyl or naphthyl) or heteroaryl group that is fused to a non-aromatic ring (e.g., cycloalkyl, cycloalkenyl, or heterocyclyl), where the ring system contains at least one heterotom. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized or substituted. In certain embodiments, the term heterocyclic refers to a non-aromatic 5-, 6-, or 7-membered monocyclic ring wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Where a heterocycle is polycyclic, the constituent rings may be fused together, form a spirocyclic structure, or the polycyclic heterocycle may be a bridged heterocycle (e.g., quinuclidyl or. Exemplary heterocyclics include, but are not limited to, aziridinyl, azetindinyl, 1,3-diazatidinyl, pyrrolidinyl, piperidinyl, piperazinyl, thiranyl, thietanyl, tetrahydrothiophenyl, dithiolanyl, tetrahydrothiopyranyl, oxiranyl, oxetanyl, tetrahydrofuranyl, tetrahydropyranyl, pyranonyl, 3,4-dihydro-2H-pyranyl, chromenyl, 2H-chromen-2-onyl, chromanyl, dioxanyl (e.g., 1,3-dioxanyl or 1,4-dioxanyl), 1,4-benzodioxanyl, oxazinyl, oxathiolanyl, morpholinyl, thiomorpholinyl, thioxanyl, quinuclidinyl, and also derivatives of said exemplary heterocyclics where the heterocyclic is fused to an aryl (e.g., a benzene ring) or a heteroaryl (e.g., a pyridine or pyrimidine) group. Any of the heterocyclic groups described herein may be unsubstituted or substituted. A substituted heterocycle may have, for example, 1, 2, 3, 4, 5, or 6 substituents.

The term "inflammatory condition" refers to medical disorders in which inflammation is a causative factor, or in which inflammation is a result (e.g., inflammatory pain associated with rheumatoid arthritis, psoriatic arthritis, psoriatic arthritis, lupus, or other diseases associated with tissue damage). Inflammatory conditions can be chronic or acute, and non-limiting causes of inflammatory conditions include pathogens (e.g., bacterial pathogens or viral infections), tissue injury, persistent foreign bodies, and autoimmune responses. As described herein, inflammation can be related to necrosis or necroptosis, or inflammation can be independent of necrosis or necroptosis.

By "ketone" or "acyl" is meant a group having the structure —COR', where R' is selected from H, optionally substituted C1-C6 alkyl, optionally substituted cycloalkyl, optionally substituted heterocyclyl, optionally substituted aryl, or optionally substituted heteroaryl. When R' is not H, R may be unsubstituted or substituted with, for example, 1, 2, 3, 4, 5, or 6 substituents.

By "nitro" is meant a group having the structure —NO$_2$.

A "pharmaceutically acceptable excipient" as used herein refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66:1-19. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvates," as used herein, refers to compounds that retain non-covalent associations to residual solvent molecules in the solid state. For example, solvates may be prepared by crystallization, recrystallization, or precipitation from a solution that includes organic solvents, water, or a mixture thereof. Solvates include, but are not limited to, compounds that include solvent molecules in the crystal lattice following recrystallization. The molecular stoichiometry of solvation can vary from, for example, 1:1 solvent:compound to 10:1 solvent:compound. These ratios can include a mixture of associated solvent molecules. Exemplary, non-limiting examples of solvents that can form solvates with the compounds of the invention include water (for example, mono-, di-, and trihydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, or any combination thereof.

By "pharmaceutical composition" is meant a composition containing a compound of the invention, formulated with a pharmaceutically acceptable excipient, and manufactured or sold with the approval of a governmental regulatory agency as part of a therapeutic regimen for the treatment of disease in a mammal. Excipients consisting of DMSO are specifically excluded. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or any other formulation described herein.

By "stereoisomer" is meant a diastereomer, enantiomer, or epimer of a compound. A chiral center in a compound may have the S-configuration or the R-configuration. Enantiomers may also be described by the direction in which they rotate polarized light (i.e., (+) or (−)). Diastereomers of a compound include stereoisomers in which some, but not all, of the chiral centers have the opposite configuration as well as those compounds in which substituents are differently oriented in space (for example, trans versus cis).

Where a group is substituted, the group may be substituted with 1, 2, 3, 4, 5, or 6 substituents. Optional substituents, which themselves may be substituted, include, but are not limited to: C1-C6 alkyl, C2-C6 alkenyl, C2-C6 alkynyl, C3-C9 cycloalkyl, C5-C9 cycloalkenyl, three- to nine-membered heterocyclyl, C6-C10 aryl, five- to eleven-membered heteroaryl, halogen; azido (—N$_3$), nitro (—NO$_2$), cyano (—CN), acyloxy (—OC(=O)R'), acyl (—C(=O)R'), alkoxy (—OR'), amido (—NR'C(=O)R" or —C(=O) NRR'), amino (—NRR'), carboxylic acid (—CO$_2$H), carboxylic ester (—CO$_2$R'), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R, R', and R" is selected, independently, from H or an optionally substituted group that is C1-C6 alkyl, C2-C6 alkenyl, C2-C6 alkynyl, C3-C9 cycloalkyl, three- to nine-membered heterocyclyl, C6-C10 aryl, or five- to eleven-membered heteroaryl. A substituted group may have, for example, 1, 2, 3, 4, 5, 6, 7, 8, or 9 substituents. In some embodiments, each hydrogen in a group may be replaced by a substituent group (e.g., perhaloalkyl groups such as —CF$_3$ or —CF$_2$CF$_3$ or perhaloaryls such as —C$_6$F$_5$). In other embodiments, a substituent group may itself be further substituted by replacing a hydrogen of said substituent group with another substituent group such as those described herein. Substituents may be further substituted with, for example, 1, 2, 3, 4, 5, or 6 substituents as defined herein. For example, a lower C1-C6 alkyl or an aryl substituent group (e.g., heteroaryl, phenyl, or naphthyl) may be further substituted with 1, 2, 3, 4, 5, or 6 substituents as described herein.

DETAILED DESCRIPTION OF THE INVENTION

Described herein are a series of heterocyclic derivatives that can inhibit tumor necrosis factor alpha (TNF-α)-induced necroptosis. The heterocyclic compounds of the invention are described by, e.g., any of Formulas (I)-(XV) and include compounds (1)-(21), and can inhibit TNF-α induced necroptosis in FADD-deficient variant of human Jurkat T cells. Pharmaceutical compositions including the compounds of the invention are also described. The invention also features kits and methods of treatment featuring the compounds and compositions of the invention.

The present invention features compounds, pharmaceutical compositions, kits, and methods for treating a range of conditions, e.g., those in which cell or tissue necrosis is a causative factor or result, those in which loss of proliferative capacity is a causative factor or a result, those in which cytokines of the TNFα family are a causative factor or a result, and those in which RIP1 and/or RIP3 protein is a contributing factor. The compounds of the present invention (e.g., a compound according to any of formulas (I)-(XXVI) or any of compounds (1)-(27)) can be used, for example, as therapeutics to decrease necrosis in a desired cell, to increase cell proliferation, to stimulate immune response, or to modulate inflammation and associated conditions. In some embodiments, the compounds of the present invention (e.g., a compound according to any of formulas (I)-(XXVI) or any of compounds (1)-(27)) can also be used, for example, to treat conditions where necroptosis is likely to play a substantial role, including, but not limited to those described herein.

Exemplary a conditions in which the compounds of the invention can be useful for treatment include, but are not limited to: neurodegenerative diseases of the central or peripheral nervous system; the result of retinal neuronal cell death; the result of cell death of cardiac muscle; the result of cell death of cells of the immune system; stroke; liver disease; pancreatic disease; the result of cell death associated with renal failure; heart, mesenteric, retinal, hepatic or brain ischemic injury; ischemic injury during organ storage; head trauma; septic shock; coronary heart disease; cardiomyopathy; bone avascular necrosis; sickle cell disease; muscle wasting; gastrointestinal disease; tuberculosis; diabetes; alteration of blood vessels; muscular dystrophy; graft-versus-host disease; viral infection; Crohn's disease; ulcerative colitis; asthma; atherosclerosis; pain (e.g., inflammatory pain, diabetic pain, or pain associated from trauma or burn); chronic or acute inflammatory conditions such as rheumatoid arthritis, psoriasis, and Stevens-Johnson syndrome; any condition in which cell or tissue necrosis is a causative factor or result; any condition in which alteration in cell proliferation, differentiation or intracellular signaling is a causative factor; and any condition in which RIP1 and/or RIP3 protein is a contributing factor. Other conditions are described herein.

The invention features compounds that can be described generally by Formula (I)

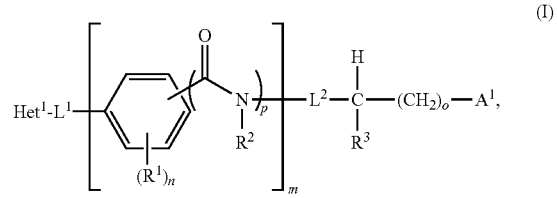

or any pharmaceutically acceptable salt thereof, or stereoisomer thereof, where m is 0 or 1;

Het$^1$ is an optionally substituted bicyclic heteroaryl;

L$^1$ is a covalent bond, an optionally substituted C1-C4 alkylene, an optionally substituted C2-C4 alkenylene, an optionally substituted C2-C4 alkynylene, an optionally substituted C3-C6 cycloalkyl, or an optionally substituted three- to-six membered heterocyclyl;

n is an integer between 0-4;

o is 0 or 1;

p is 0 or 1;

each R$^1$, when present, is independently optionally substituted C1-C6 alkyl, optionally substituted C2-C6 alkenyl, optionally substituted C2-C6 alkynyl, optionally substituted C3-C9 cycloalkyl, optionally substituted C5-C9 cycloalkenyl, optionally substituted three- to nine-membered heterocyclyl, optionally substituted C6-C10 aryl, optionally substituted five- to eleven-membered heteroaryl, halogen, —OH, N$_3$, NO$_2$, —CO$_2$H, —NC, or CN; or is a group selected from —OC(=O)R$^{4A}$, —C(=O)R$^{4A}$, —OR$^{4A}$, —NR$^{4A}$C(O)R$^{4B}$, —C(=O)NR$^{4A}$R$^{4B}$, —NR$^{4A}$R$^{4B}$, —CO$_2$R$^{4A}$, —OC(O)NR$^{4A}$R$^{4B}$, —NR$^{4A}$C(O)OR$^{4B}$, —S(=O)$_2$OR$^{4A}$, —S(=O)$_2$NR$^{4A}$R$^{4B}$, NR$^{4A}$S(O)$_2$R$^{4B}$, and —S(O)$_2$R$^{4A}$, where each R$^{4A}$ and R$^{4B}$ is independently H or an optionally substituted group that is C1-C6 alkyl, C2-C6 alkenyl, C2-C6 alkynyl, C3-C9 cycloalkyl, three- to nine-membered heterocyclyl, C6-C10 aryl, or five- to eleven-membered heteroaryl;

$R^2$ is H or optionally substituted C1-C6 alkyl, or $R^2$ combines with $R^3$ to form an optionally substituted C1-C3 alkylene moiety;

$L^2$ is a covalent bond or an optionally substituted C1-C4 alkylene;

$R^3$ is H or optionally substituted C1-C6 alkyl, or $R^3$ combines with $R^2$ to form an optionally substituted C1-C3 alkylene moiety;

$A^1$ is a fragment that is (a)
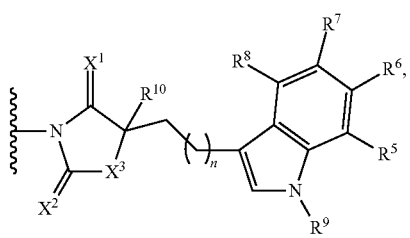

where
each $X^1$ and $X^2$ is, independently, O or S;
$X^3$ is O or $NR^{11}$;
n is 0 or 1;
each of $R^5$, $R^6$, $R^7$, and $R^8$ is, independently, H, OH, optionally substituted C1-C6 alkyl, optionally substituted C1-C6 alkoxy, halogen, $N(R^{12})_2$, $CO_2R^{12}$, $NO_2$, $NHC(O)R^{12}$, optionally substituted aryl, optionally substituted heteroaryl, or piperizine;
$R^9$ is H or optionally substituted C1-C6 alkyl;
$R^{10}$ is H or optionally substituted C1-C6 alkyl;
$R^{11}$ is H or optionally substituted C1-C6 alkyl;
$R^{12}$ represents H, optionally substituted C1-C6 alkyl, optionally substituted aryl, optionally substituted alkaryl, optionally substituted C2-C6 alkenyl, optionally substituted C2-C6 alkynyl, or optionally substituted heteroaryl
or (b)
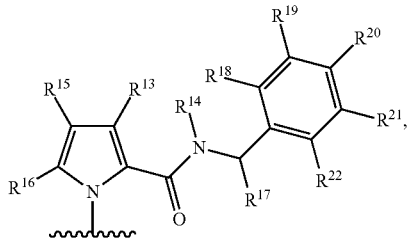

where
$R^{13}$ is selected from H, halogen, optionally substituted C1-C6 alkyl, optionally substituted C1-C6 cycloalkyl, or optionally substituted aryl;
$R^{14}$ is selected from H or optionally substituted C1-C6 alkyl;
$R^{15}$ and $R^{16}$ are selected, independently, from hydrogen, halogen, carboxamido, nitro, and cyano;
$R^{17}$ is, independently, selected from H, optionally substituted aryl, or optionally substituted C1-C6 alkyl;

each of $R^{18}$, $R^{19}$, $R^{20}$, $R^{21}$, and $R^{22}$ is selected, independently, from H, optionally substituted C1-C6 alkyl, halogen, optionally substituted amino, optionally substituted carboxamido, optionally substituted C1-C6 alkoxy, nitro, and cyano.

The compounds of the invention can also be described by one the following formulas,

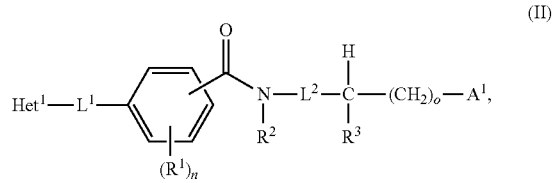
(II)

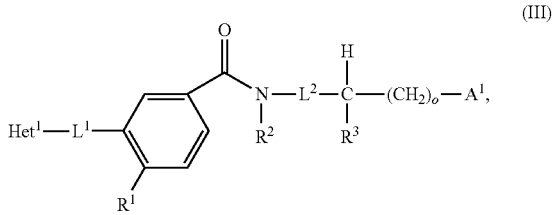
(III)

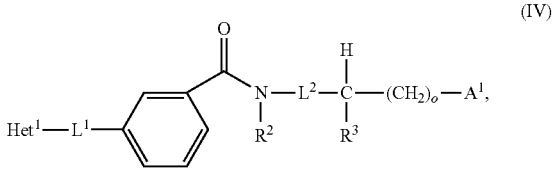
(IV)

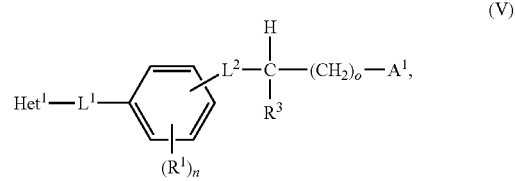
(V)

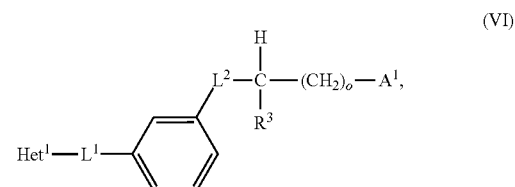
(VI)

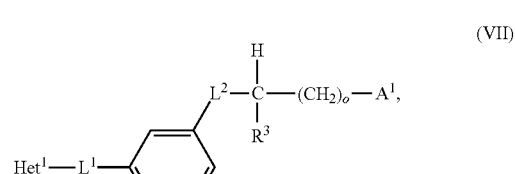
(VII)

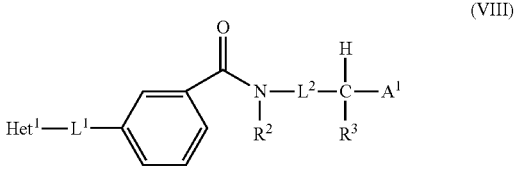
(VIII)

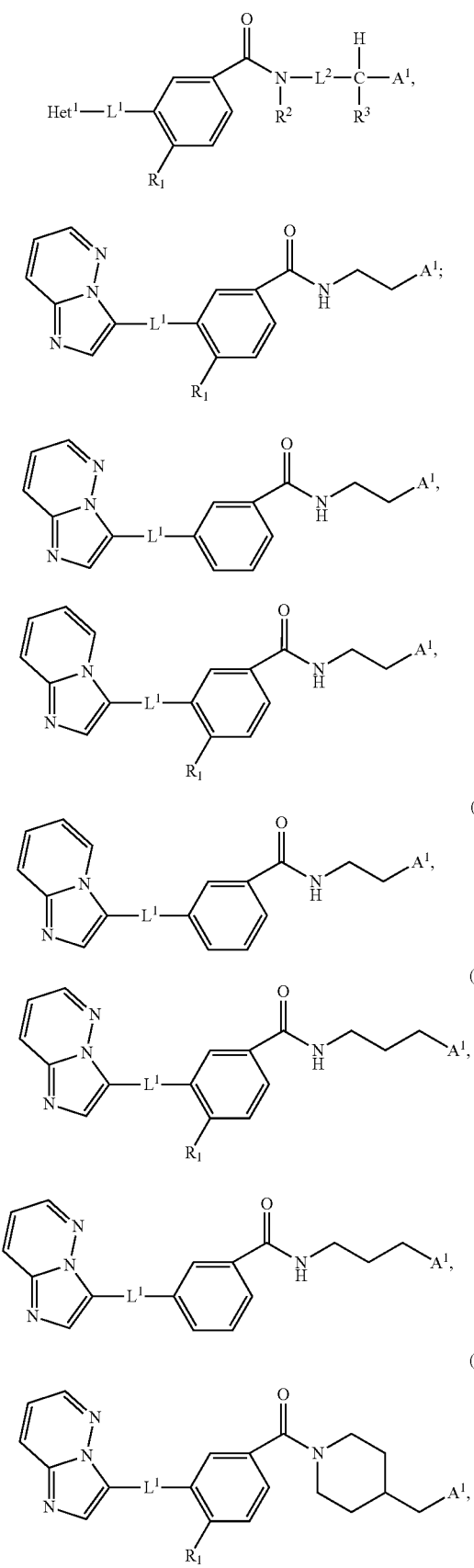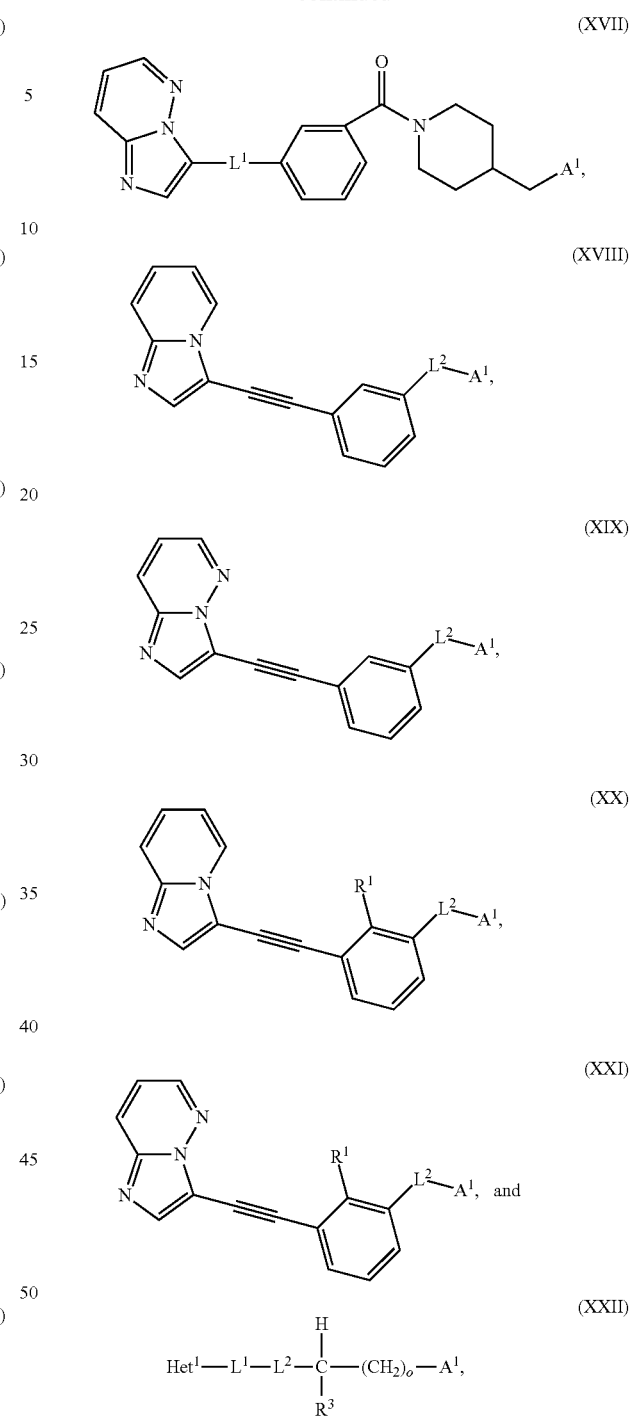

or a pharmaceutically acceptable salt thereof, or a stereoisomer thereof.

Compounds of the invention (e.g., a compound according to any of formulas (I)-(XXVI) or any of compounds (1)-(27)) can be synthesized according to methods known in the art or by the methods described herein. The strategies described herein can be used to prepare the instantly claimed compounds by varying the starting materials and building blocks used in the syntheses. For example, substructure A1 can be described by the following formula,

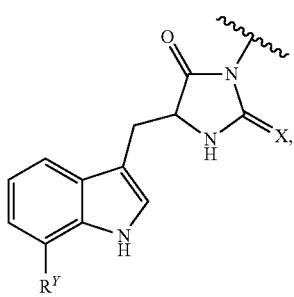

wherein $R^Y$ represents methyl, methoxy, Cl, Br, or F, and X is O or S. In some embodiments, substructure A1 is one of the following enantiomers,

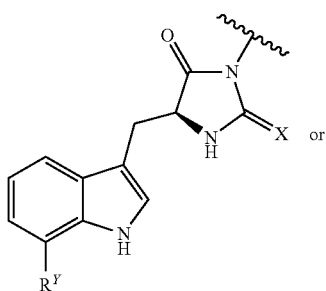

or

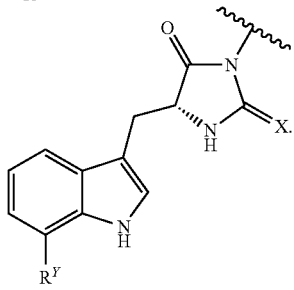

These compounds can be prepared according to methods in the art (see, e.g.: U.S. Pat. Nos. 7,491,743, 8,143,300, and 8,324,262; U.S. Patent Application Publication No. 2012/0149702; and U.S. patent application Ser. No. 13/665,263, each of which is hereby incorporated by reference in its entirety.

Table 1 also provides exemplary substructures A1 which can be prepared by, e.g., adapting methods known in the art.

TABLE 1

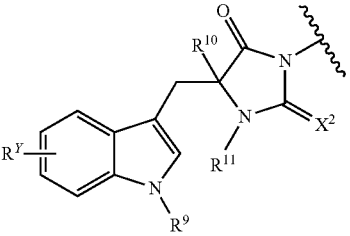

| Substructure No. | $R^Y$ | $R^{10}$ | $R^{11}$ | $X^2$ | $NR^9$ |
|---|---|---|---|---|---|
| B | H | H | H | S | NH |
| C | H | Me | H | S | NH |
| D | H | H | Me | S | NH |

TABLE 1-continued

| Substructure No. | $R^Y$ | $R^{10}$ | $R^{11}$ | $X^2$ | $NR^9$ |
|---|---|---|---|---|---|
| E | H | H | H | O | NH |
| F | 6-F | H | H | S | NH |
| G | 5-OMe | H | H | S | NH |
| H | 5-OH | H | H | S | NH |
| I | H | H | H | S | NMe |
| J | 7-F | H | H | S | NH |
| K | 7-Cl | H | H | S | NH |
| L | 6-Cl | H | H | S | NH |
| M | 7-Br | H | H | S | NH |
| N | 7-OMe | H | H | S | NH |
| O | 7-Cl | H | H | S | NMe |
| P | 6-SO$_2$Me; 7-Cl | H | H | S | NH |
| Q | H | H | H | S | NH |
| R | H | H | H | S | NH |
| S | H | H | H | O | NH |
| T | H | H | H | O | NH |
| U | H | H | H | O | NH |
| V | 7-Me | H | H | O | NH |
| W | 5-Cl | H | H | O | NH |
| X | 7-OMe | H | H | O | NH |
| Y | 5-OMe | H | H | O | NH |
| Z | 6-Cl | H | H | O | NH |
| AA | 7-F | H | H | O | NH |

Still other compounds that can be featured as Substructure A1 are provided in Table 2. These compounds can be prepared by, e.g., adapting methods known in the art for synthesis of the parent pyrrole compounds such as those described in U.S. Pat. No. 8,278,344 and U.S. Patent Application Publication No. 2012/0309795, each of which is incorporated by reference.

TABLE 2

BB

![structure BB]

CC

![structure CC]

TABLE 2-continued

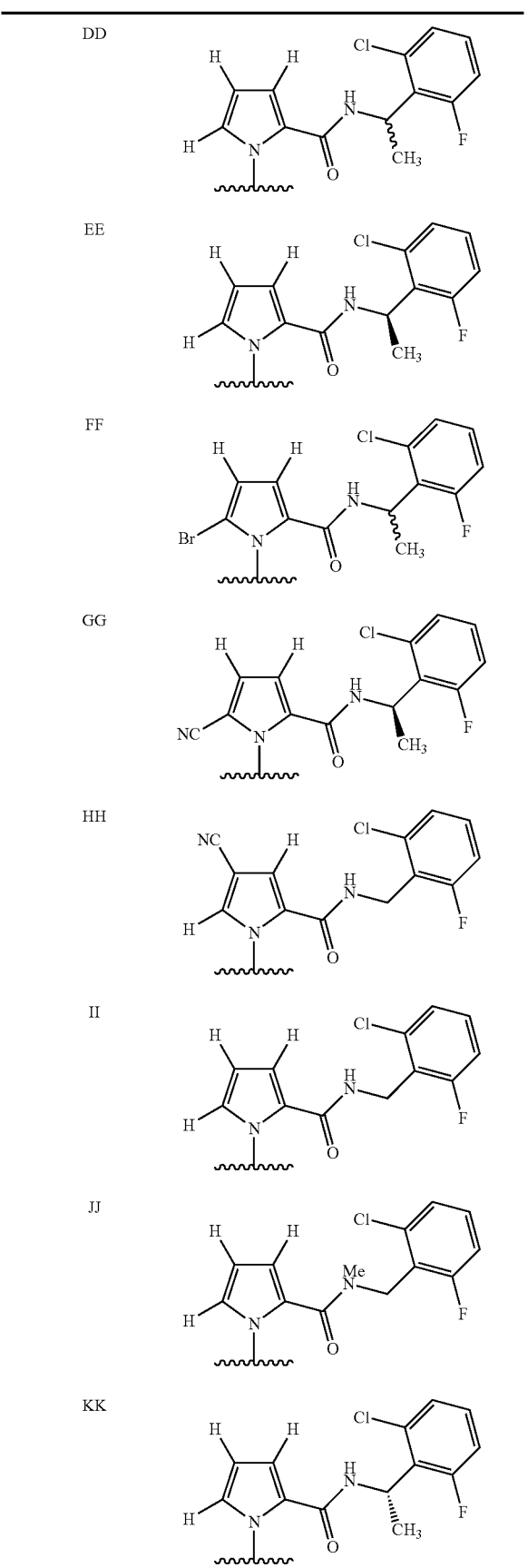

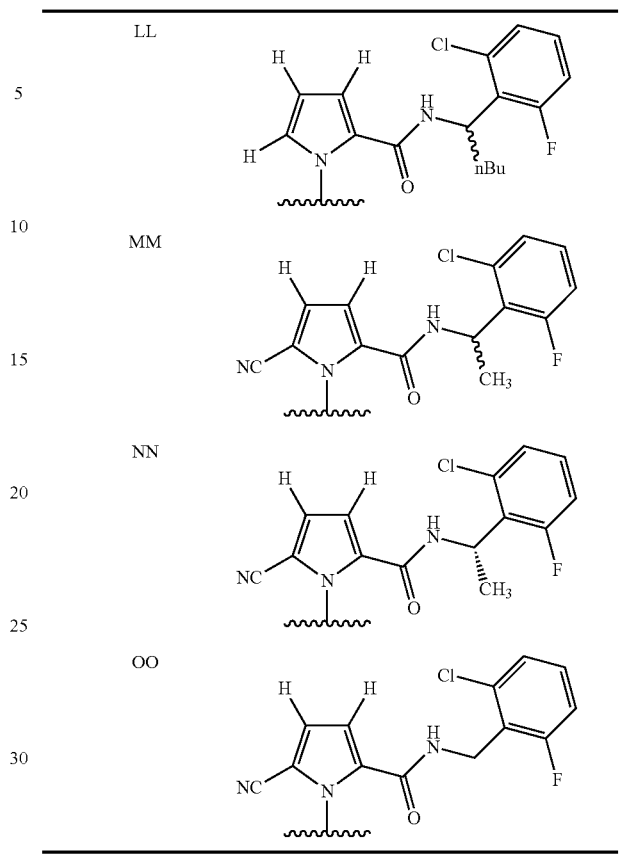

RIP1

RIP1 is a unique death domain-containing kinase that has been shown to interact with Fas and TNFR1. RIP1 contains a N-terminal kinase domain with homology to both Ser/Thr and tyrosine kinases, a C-terminal death domain, and an intermediate domain (IM). Its kinase activity is not required for DR-induced apoptosis nor NFκB activation, which is regulated by the intermediate domain (IM) of RIP. RIP contributes to a wide range of cellular regulatory paradigms, including cytokines, e.g., TNFα and IL-1β, and Toll-like receptor 3 and 4 mediated induction of NFkB.

Kinase activity of RIP1 is essential for the alternative necrotic cell death pathway mediated by FasL, TNFα and TRAIL, which we subsequently termed necroptosis (see, e.g., U.S. Pat. No. 8,324,262, and references cited therein, each of which is incorporated by reference). Analysis has been undertaken of the domains of RIP required for the death receptor-induced necroptosis in RIP-deficient clone of Jurkat cells, which are otherwise insensitive to this pathway due to the lack of RIP. In these studies, not only was the kinase domain of RIP required to mediate necroptosis triggered by Fas ligand (FasL)/cyclohexamide and zVAD.fmk, but the death domain of the molecule is also required. In addition, it has been found that the activation of RIP1 kinase by dimerization is sufficient to induce necroptosis inhibitable by Nec-1. Thus, the kinase activity of RIP1 represents an essential upstream signaling step in necroptosis.

Accordingly, screening assays may be performed in which RIP1 is utilized as a target, and candidate compounds are assayed for their ability to bind to or otherwise inhibit RIP1. For example, assays that measure inhibition of autophosphorylation of RIP1 can be used. Alternatively, assays that measure binding of a candidate compound to RIP1 are useful in the methods of the invention. Many other variations of binding assays are known in the art and can be employed. RIP1 binding assays are described, e.g., in U.S. Pat. No. 6,211,337, which is hereby incorporated by reference.

To identify compounds that are selective or specific for RIP1, screening assays can be performed using multiple targets. For example, for a given candidate compound, the binding, autophosphorylation, or other measure of target activity may be assayed for both RIP1 and RIP2, or alternatively both RIP1 and RIP3, and the results compared. Candidate compounds that exert a greater effect on RIP1 than RIP2, RIP3, or another homologue or other molecule chosen for this purpose, are considered to be specific for RIP1, and may be particularly desirable in the methods of the invention. Other assays are known in the art, and any method for measuring protein interactions or inhibition of the activity of a target molecule (e.g., RIP1) may be utilized. Such methods include, but are not limited to fluorescence polarization assays, mass spectrometry (Nelson and Krone, J. Mol. Recognit., 12:77-93, 1999), surface plasmon resonance (Spiga et al., FEBS Lett., 511:33-35, 2002; Rich and Mizka, J. Mol. Recognit., 14:223-228, 2001; Abrantes et al., Anal. Chem., 73:2828-2835, 2001), fluorescence resonance energy transfer (FRET) (Bader et al., J. Biomol. Screen, 6:255-264, 2001; Song et al., Anal. Biochem. 291:133-41, 2001; Brockhoff et al., Cytometry, 44:338-248, 2001), bioluminescence resonance energy transfer (BRET) (Angers et al., Proc. Natl. Acad. Sci. USA, 97:3684-3689, 2000; Xu et al., Proc. Natl. Acad. Sci. USA, 96:151-156, 1999), fluorescence quenching (Engelborghs, Spectrochim. Acta A. Mol. Biomol. Spectrosc., 57:2255-2270, 1999; Geoghegan et al., Bioconjug. Chem. 11:71-77, 2000), fluorescence activated cell scanning/sorting (Barth et al., J. Mol. Biol., 301:751-757, 2000), ELISA, and radioimmunoassay (RIA).

Additionally, the interaction between compounds that can inhibit necroptosis or necrosis and RIP1 can also be studied using in silico methods, such as those described in the examples.

Pharmaceutical Compositions

Compounds of the invention (e.g., a compound according to any of formulas (I)-(XXVI) or any of compounds (1)-(27)) can be formulated into pharmaceutical compositions for administration to human subjects in a biologically compatible form suitable for administration in vivo. Accordingly, the present invention provides a pharmaceutical composition comprising a compound of the invention in admixture with a pharmaceutically acceptable excipient. Conventional procedures and ingredients for the selection and preparation of suitable formulations are described, for example, in Remington's Pharmaceutical Sciences (2003-20$^{th}$ edition) and in The United States Pharmacopeia: The National Formulary (USP 24 NF 19), published in 1999.

The compounds of the invention (e.g., a compound according to any of formulas (I)-(XXVI) or any of compounds (1)-(27)) may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

Pharmaceutically Acceptable Excipients

Pharmaceutically acceptable excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

Oral Administration

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

Parenteral Administration

A compound of the invention may also be administered parenterally. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Nasal Administration

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Buccal or Sublingual Administration

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal alone or in combination with pharmaceutically acceptable carriers, as noted above, the proportion of which is determined by the solubility and chemical nature of the compound, chosen route of administration, and standard pharmaceutical practice.

Dosage Amounts

The amount of active ingredient in the compositions of the invention can be varied. One skilled in the art will appreciate that the exact individual dosages may be adjusted somewhat depending upon a variety of factors, including the protein being administered, the time of administration, the route of administration, the nature of the formulation, the rate of excretion, the nature of the subject's conditions, and the age, weight, health, and gender of the patient. Generally, dosage levels of between 0.1 µg/kg to 100 mg/kg of body weight are administered daily as a single dose or divided into multiple doses. Desirably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

Therapeutic Uses

Cell death has traditionally been categorized as either apoptotic or necrotic based on morphological characteristics (Wyllie et al., *Int. Rev. Cytol.* 68: 251 (1980)). These two modes of cell death were also initially thought to occur via regulated (caspase-dependent) and non-regulated processes, respectively. Subsequent studies, however, demonstrate that the underlying cell death mechanisms resulting in these two phenotypes are much more complicated and under some circumstances interrelated. Furthermore, conditions that lead to necrosis can occur by either regulated caspase-independent or non-regulated processes.

One regulated caspase-independent cell death pathway with morphological features resembling necrosis, called necroptosis, has been described (Degterev et al., *Nat. Chem. Biol.* 1:112 (2005)). This manner of cell death can be initiated with various stimuli (e.g., TNF-α and Fas ligand) and in an array of cell types (e.g., monocytes, fibroblasts, lymphocytes, macrophages, epithelial cells and neurons). Necroptosis may represent a significant contributor to and in some cases predominant mode of cellular demise under pathological conditions involving excessive cell stress, rapid energy loss and massive oxidative species generation, where the highly energy-dependent apoptosis process is not operative.

The identification and optimization of low molecular weight molecules capable of inhibiting necroptosis will assist in elucidating its role in disease patho-physiology and can provide compounds (i.e., necrostatins) for anti-necroptosis therapeutics. The discovery of compounds that prevent caspase-independent cell death (e.g., necrosis or necroptosis) would also provide useful therapeutic agents for treating or preventing conditions in which necrosis occurs. For example, necrostatins can suppress necroptosis by specifically inhibiting receptor interacting protein 1 (RIP1) activity (e.g., Xie et al., *Structure,* 21(3):493-499, 2013). RIP3, which is a RIP1 family member, has also been implicated in necroptosis (see, e.g., Christofferson et al., *Curr. Opin. Cell Biol.* 22(2):263-268, 2010). Accordingly, methods by which RIP1 and/or RIP3 activity can be modulated can also be useful for the treatment of conditions in which RIP1 and/or RIP3 protein is a contributing factor.

These compounds and methods would be particularly useful for the treatment of neurodegenerative diseases, ischemic brain and heart injuries, and head trauma. Exemplary assays for identifying inhibitors of necrosis and necroptosis are described herein in the Examples.

Accordingly, the compounds and compositions disclosed herein can be used to treat disorders where necroptosis is likely to play a substantial role or where RIP1 and/or RIP3 protein is a contributing factor. Exemplary conditions that can be treated using the methods described herein include: cerebral ischemia, traumatic brain injury (Gennarelli et al. In *Textbook of Traumatic Brain Injury*; Silver et al., Eds.; American Psychiatric Publishing Inc.: Washington D.C., 2005; p 37), a neurodegenerative disease of the central or peripheral nervous system (Martin et al. *Brain Res. Bull.* 1998, 46, 281), the result of retinal neuronal cell death, the result of cell death of cardiac muscle, the result of cell death of cells of the immune system; organ ischemia such as stroke (Lo et al. *Nat. Rev. Neurosci.* 2003, 4, 399.), myocardial infarction (McCully et al. *Am. J. Physiol. Heart Circ. Physiol.* 2004, 286, H1923), or retinal ischemia (Osborne et al. *Prog. Retin. Eye Res.* 2004, 23, 91); liver disease (Kaplowitz, *J. Hepatol.* 2000, 32 (1 Suppl.), 39; Malhi et al. *Hepatology* 2006, 43 (2 Suppl. 1), S31; and Ferrell et al. In *Pathology of the Liver,* 4$^{th}$ Edition; MacSween et al., Eds.; Churchill Livingstone: London, 2002; p 314), pancreatic disease, the result of cell death associated with renal failure; heart, mesenteric, retinal, hepatic or brain ischemic injury, ischemic injury during organ storage, head trauma, septic shock, coronary heart disease, cardiomyopathy, myocardial infarction, bone avascular necrosis, sickle cell disease, muscle wasting, gastrointestinal disease, tuberculosis, diabetes, alteration of blood vessels, muscular dystrophy, graft-versus-host disease, viral infection, Crohn's disease, ulcerative colitis, asthma, or any condition in which alteration in cell proliferation, differentiation or intracellular signaling is a causative factor; cancer chemo/radiation therapy-induced necrosis (Giglio et al. *Neurologist* 2003, 9, 180; Ramesh et al. *Am. J. Physiol Renal Physiol.* 2003, 285, F610; and Miyaguchi et al. *J. Laryngol. Otol.* 1997, 111, 763); acute necrotizing pancreatitis (Rosai. In *Rosai and Ackerman's Surgical Pathology, 9$^{th}$ Edition*; Mosby: New York, 2004; Vol. 1, p 1063; Wrobleski et al. *J. AACN Clin. Issues* 1999, 10, 464; and Marenidova et al., *J Biol Chem.* 2006, 281, 3370); atherosclerosis (e.g, Lin et al., *Cell Reports,* 3:200-210, 2013); and inflammatory conditions (e.g., Wallach et al., *Trends in Immunology,* 32(11):505-509, 2011; Kang et al., *Immunity,* 38:27-40, 2013; and Chan, *Cold Spring Harb. Perspect. Biol.*, 1-12, 2012). Compounds of the invention can also be used in screening methods to identify targets of necroptosis and to identify additional inhibitors of necroptosis, as well as in assay development.

The compounds (e.g., a compound according to any of formulas (I)-(XXVI) or any of compounds (1)-(27)) and compositions disclosed herein can be evaluated for their pharmacological properties in animal models of disease. The compounds identified to decrease necrosis or necroptosis may be structurally modified and subsequently used to decrease necrosis or necroptosis, or to treat a subject with a condition in which necrosis or necroptosis occurs. The methods used to generate structural derivatives of the small molecules that decrease necrosis or necroptosis are readily known to those skilled in the fields of organic and medicinal chemistry.

Therapy according to the invention may be performed alone or in conjunction with another therapy, for example in combination with apoptosis inhibitors, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, as well as how the patient responds to the treatment. Additionally, a person having a greater risk of developing a condition may receive prophylactic treatment to inhibit or delay symptoms of the disease.

In some embodiments, the compounds (e.g., compounds having a structure according to any of Formulas (I)-(VIII), or any of compounds (1)-(20)) and compositions described herein can be used to treat any of the following disorders where necroptosis is likely to play a substantial role: a neurodegenerative disease of the central or peripheral nervous system, the result of retinal neuronal cell death, the result of cell death of cardiac muscle, the result of cell death of cells of the immune system; stroke, liver disease, pancreatic disease, the result of cell death associated with renal failure; heart, mesenteric, retinal, hepatic or brain ischemic injury, ischemic injury during organ storage, head trauma, septic shock, coronary heart disease, cardiomyopathy, myocardial infarction, bone avascular necrosis, sickle cell disease, muscle wasting, gastrointestinal disease, tuberculosis, diabetes, alteration of blood vessels, muscular dystrophy, graft-versus-host disease, viral infection, bacterial infection, Crohn's disease, ulcerative colitis, asthma, and any condition in which alteration in cell proliferation, differentiation or intracellular signaling is a causative factor.

Conditions Caused by Alteration in Cell Proliferation, Differentiation, or Intracellular Signaling Conditions in which alteration in cell proliferation, differentiation or intracellular signaling is a causative factor include cancer and infection, e.g., by viruses (e.g., acute, latent and persistent), bacteria, fungi, or other microbes.

Exemplary viruses are human immunodeficiency virus (HIV), Epstein-Barr virus (EBV), cytomegalovirus (CMV)5 human herpesviruses (HHV), herpes simplex viruses (HSV), human T-Cell leukemia viruses (HTLV)5 Varicella-Zoster virus (VZV), measles virus, papovaviruses (JC and BK), hepatitis viruses, adenovirus, parvoviruses, and human papillomaviruses. Exemplary diseases caused by viral infection include, but are not limited to, chicken pox, Cytomegalovirus infections, genital herpes, Hepatitis B and C, influenza, and shingles.

Exemplary bacteria include, but are not limited to *Campylobacter jejuni*, *Enterobacter* species, *Enterococcus faecium, Enterococcus faecalis, Escherichia coli* (e.g., *E. coli* O157:H7), Group A streptococci, *Haemophilus influenzae, Helicobacter pylori, listeria, Mycobacterium tuberculosis, Pseudomonas aeruginosa, S. pneumoniae, Salmonella, Shigella, Staphylococcus aureus,* and *Staphylococcus epidermidis*. Exemplary diseases caused by bacterial infection include, but are not limited to, anthrax, cholera, diphtheria, foodborne illnesses, leprosy, meningitis, peptic ulcer disease, pneumonia, sepsis, tetanus, tuberculosis, typhoid fever, and urinary tract infection.

Neurodegenerative Diseases

Exemplary neurodegenerative diseases are Alzheimer's disease, Huntington's disease, Parkinson's disease, amyotrophic lateral sclerosis, HIV-associated dementia, cerebral ischemia, amyotropic lateral sclerosis, multiple sclerosis, Lewy body disease, Menke's disease, Wilson's disease, Creutzfeldt-Jakob disease, Fahr disease, and progressive supranuclear palsy. Exemplary muscular dystrophies or related diseases are Becker's muscular dystrophy, Duchenne muscular dystrophy, myotonic dystrophy, limb-girdle muscular dystrophy, Landouzy-Dejerine muscular dystrophy, facioscapulohumeral muscular dystrophy (Steinert's disease), myotonia congenita, Thomsen's disease, and Pompe's disease. Muscle wasting can be associated with cancer, AIDS, congestive heart failure, and chronic obstructive pulmonary disease, as well as include necrotizing myopathy of intensive care.

Exemplary neurodegenerative conditions are Alzheimer's disease, Huntington's disease, Parkinson's disease, amyotrophic lateral sclerosis, HIV-associated dementia, cerebral ischemia, amyotropic lateral sclerosis, multiple sclerosis, Lewy body disease, Menke's disease, Wilson's disease, Creutzfeldt-Jakob disease, Fahr disease, and progressive supranuclear palsy.

Exemplary muscular dystrophies or related diseases are Becker's muscular dystrophy, Duchenne muscular dystrophy, myotonic dystrophy, limb-girdle muscular dystrophy, Landouzy-Dejerine muscular dystrophy, facioscapulohumeral muscular dystrophy (Steinert's disease), myotonia congenita, Thomsen's disease, and Pompe's disease.

Muscle wasting can be associated with cancer, AIDS, congestive heart failure, and chronic obstructive pulmonary disease, as well as include necrotizing myopathy of intensive care The compounds and compositions described herein can additionally be used to boost the immune system, whether or not the patient being treated has an immunocompromising condition. For example, the compounds described herein can be used in a method to strengthen the immune system during immunization, e.g., by functioning as an adjuvant, or by being combined with an adjuvant.

The compounds and compositions described herein can also be used to treat inflammatory conditions, which may be, e.g., chronic or acute. Exemplary inflammatory conditions include: alkylosing spondylitis, arthritis (e.g., osteoarthritis, rheumatoid arthritis (RA), and psoriatic arthritis), asthma, atherosclerosis, Crohn's disease, colitis, dermatitis, diverticulitis, fibromyalgia, hepatitis, irritable bowel syndrome (IBS), psoriasis, Stevens-Johnson syndrome, systemic lupus erythematous (SLE), nephritis, and ulcerative colitis. Still other inflammatory conditions include: immunoinflammatory disorders such as acne vulgaris; acute respiratory distress syndrome; Addison's disease; allergic rhinitis; allergic intraocular inflammatory diseases, ANCA-associated small-vessel vasculitis; ankylosing spondylitis; arthritis, asthma; atherosclerosis; atopic dermatitis; autoimmune hemolytic anemia; autoimmune hepatitis; Behcet's disease; Bell's palsy; bullous pemphigoid; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; erythema nodosum; exfoliative dermatitis; fibromyalgia; focal glomerulosclerosis; giant cell arteritis; gout; gouty arthritis; graft-versus-host disease; hand eczema; Henoch-Schonlein purpura; herpes gestationis; hirsutism; idiopathic cerato-scleritis; idiopathic pulmonary fibrosis; idiopathic thrombocytopenic purpura; inflammatory bowel or gastrointestinal disorders, inflammatory dermatoses; lichen planus; lupus nephritis; lymphomatous tracheobronchitis; macular edema;

multiple sclerosis; myasthenia gravis; myositis; osteoarthritis; pancreatitis; pemphigoid gestationis; pemphigus vulgaris; polyarteritis nodosa; polymyalgia rheumatica; pruritus scroti; pruritis/inflammation, psoriasis; psoriatic arthritis; rheumatoid arthritis; relapsing polychondritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; shoulder tendinitis or bursitis; Sjogren's syndrome; Still's disease; stroke-induced brain cell death; Sweet's disease; systemic lupus erythematosus; systemic sclerosis; Takayasu's arteritis; temporal arteritis; toxic epidermal necrolysis; tuberculosis; type-1 diabetes; ulcerative colitis; uveitis; vasculitis; and Wegener's granulomatosis.

Further, the compounds and compositions described herein can also be used in the treatment or prevention of pain, including nociceptive pain, inflammatory pain, functional pain and neuropathic pain, all of which may be acute or chronic. For example, the subject (e.g., a human) being treated may be diagnosed as having peripheral diabetic neuropathy, compression neuropathy, post herpetic neuralgia, trigeminal or glossopharyngeal neuralgia, post traumatic or post surgical nerve damage, lumbar or cervical radiculopathy, AIDS neuropathy, metabolic neuropathy, drug induced neuropathy, complex regional pain syndrome, arachnoiditis, spinal cord injury, bone or joint injury, tissue injury, psoriasis, scleroderma, pruritis, cancer (e.g., prostate, colon, breast, skin, hepatic, or kidney), cardiovascular disease (e.g., myocardial infarction, angina, ischemic or thrombotic cardiovascular disease, peripheral vascular occlusive disease, or peripheral arterial occlusive disease), sickle cell anemia, migraine cluster or tension-type headaches, inflammatory conditions of the skin, muscle, or joints, fibromyalgia, irritable bowel syndrome, non cardiac chest pain, cystitis, pancreatitis, or pelvic pain. Alternatively, the pain may be the result of or associated with trauma (e.g., a traumatic injury), diabetes, surgery, burn of the cutaneous tissue (caused by a thermal, chemical, or radiation stimulus), or a sunburn.

Additional conditions that can be treated using the compounds provided herein include those described in, e.g.: U.S. Pat. Nos. 6,756,394; 7,253,201; 7,491,743; 8,143,300; 8,278,344; and 8,324,262; U.S. Patent Application Publication Nos. 20100087453, 2012/0309795, and 20120122889; and International Publication Nos. WO 2011/133964 and WO/2012/061045; each of which is hereby incorporated by reference in its entirety.

Combination Therapy

If desired, treatment with the compounds and compositions described herein can be combined with therapies for the treatment of any of the conditions described herein. Such treatments include surgery, radiotherapy, chemotherapy, or the administration of one or more additional compounds. Exemplary compounds suitable for combination therapy with Nec compounds are described below.

The compounds and compositions described herein can be administered in combination with compounds that are apoptosis inhibitors, i.e., compounds that inhibit apoptosis, including but not limited to reversible and irreversible caspase inhibitors. An example of an apoptosis inhibitor includes zVAD, IETD, YVAD, DEVD, and LEHD.

In some instances, the compounds of the invention are administered in combination with PARP poly(ADP-ribose) polymerase inhibitors. Non-limiting examples of PARP inhibitors include 6(5H)-phenanthridinone, 4-Amino-1,8-naphthalimide, 1,5-Isoquinolinediol, and 3-Aminobenzamide.

Compounds of the invention can also be administered in combination with Src inhibitors. Src proteins are mammalian cytoplasmic tyrosine kinases that play an extensive role in signal transduction. Examples of Src inhibitors include but are not limited to: PP1 (1-(1,1-dimethylethyl)-1-(4-methylphenyl)-1H-pyrazolo[3,4-d]pyrimidin-4-amine), PP2 (3-(4-chlorophenyl)-1-(1,1-dimethylethyl)-1H-pyr-azolo[3,4-d]pyrimidin-4-amine), damnacanthal (3-hydroxy-1-methoxy-2-anthra-quinonecarboxaldehyde), and SU-5565.

The methods of the invention involve, in some aspects, combinations of compounds that are inhibitors of cellular necrosis (e.g., heterocyclic thiohydantoin, hydantoin, oxazolidinone, thioxo-oxazolidinone, pyrimidinone, or oxazinanone compounds, or combinations thereof) with agents for the treatment of cardiovascular disorders. Such agents include anti-inflammatory agents, anti-thrombotic agents, anti-platelet agents, fibrinolytic agents, lipid reducing agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), calcium channel blockers, beta-adrenergic receptor blockers, cyclooxygenase-2 inhibitors, angiotensin system inhibitors, and any combinations thereof. One preferred agent is aspirin.

Anti-inflammatory agents include alclofenac; alclometasone dipropionate; algestone acetonide; alpha amylase; amcinafal; amcinafide; amfenac sodium; amiprilose hydrochloride; anakinra; anirolac; anitrazafen; apazone; balsalazide disodium; bendazac; benoxaprofen; benzydamine hydrochloride; bromelains; broperamole; budesonide; carprofen; cicloprofen; cintazone; cliprofen; clobetasol propionate; clobetasone butyrate; clopirac; cloticasone propionate; cormethasone acetate; cortodoxone; deflazacort; desonide; desoximetasone; dexamethasone dipropionate; diclofenac potassium; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; flufenamic acid; flumizole; flunisolide acetate; flunixin; flunixin meglumine; fluocortin butyl; fluorometholone acetate; fluquazone; flurbiprofen; fluretofen; fluticasone propionate; furaprofen; furobufen; halcinonide; halobetasol propionate; halopredone acetate; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lornoxicam; loteprednol etabonate; meclofenamate sodium; meclofenamic acid; meclorisone dibutyrate; mefenamic acid; mesalamine; meseclazone; methylprednisolone suleptanate; morniflumate; nabumetone; naproxen; naproxen sodium; naproxol; nimazone; olsalazine sodium; orgotein; orpanoxin; oxaprozin; oxyphenbutazone; paranyline hydrochloride; pentosan polysulfate sodium; phenbutazone sodium glycerate; pirfenidone; piroxicam; piroxicam cinnamate; piroxicam olamine; pirprofen; prednazate; prifelone; prodolic acid; proquazone; proxazole; proxazole citrate; rimexolone; romazarit; salcolex; salnacedin; salsalate; salycilates; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate;

tolmetin; tolmetin sodium; triclonide; triflumidate; zidometacin; glucocorticoids; and zomepirac sodium.

Anti-thrombotic and fibrinolytic agents include plasminogen (to plasmin via interactions of prekallikrein, kininogens, factors XII, XIIIa, plasminogen proactivator, and tissue plasminogen activator (TPA)) streptokinase; urokinase: anisoylated plasminogen-streptokinase activator complex; pro-urokinase (pro-UK); rTPA (alteplase or activase); rPro-UK; abbokinase; eminase; sreptase anagrelide hydrochloride; bivalirudin; dalteparin sodium; danaparoid sodium; dazoxiben hydrochloride; efegatran sulfate; enoxaparin sodium; ifetroban; ifetroban sodium; tinzaparin sodium; retaplase; trifenagrel; warfarin; and dextrans.

Anti-platelet agents include clopridogrel; sulfinpyrazone; aspirin; dipyridamole; clofibrate; pyridinol carbamate; PGE; glucagon; antiserotonin drugs; caffeine; theophyllin; pentoxifyllin; ticlopidine; and anagrelide.

Lipid reducing agents include gemfibrozil, cholystyramine, colestipol, nicotinic acid, probucol, lovastatin, fluvastatin, simvastatin, atorvastatin, pravastatin, and cirivastatin.

Direct thrombin inhibitors include hirudin, hirugen, hirulog, agatroban, PPACK, and thrombin aptamers.

Glycoprotein IIb/IIIa receptor inhibitors include both antibodies and non-antibodies, and include but are not limited to ReoPro (abcixamab), lamifiban, and tirofiban.

Calcium channel blockers are a chemically diverse class of compounds having important therapeutic value in the control of a variety of diseases including several cardiovascular disorders, such as hypertension, angina, and cardiac arrhythmias (Fleckenstein, Cir. Res. 52:13-16 (1983); Fleckenstein, Experimental Facts and Therapeutic Prospects, John Wiley, New York (1983); McCall, D., Curr. Pract. Cardiol. 10:1-11 (1985)). Calcium channel blockers are a heterogenous group of drugs that prevent or slow the entry of calcium into cells by regulating cellular calcium channels. (Remington, The Science and Practice of Pharmacy, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexylene, gallopamil, tiapamil and tiapamil analogues (such as 1993RO-11-2933), phenyloin, barbiturates, and the peptides dynorphin, omega-conotoxin, and omega-agatoxin, and pharmaceutically acceptable salts thereof.

Beta-adrenergic receptor blocking agents are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitril HCl, 1-butylamino-3-(2,5-dichlorophenoxy-)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, -7-(2-hydroxy-3-t-butylaminpropoxy) phthalide. These compounds can be used as isomeric mixtures, or in their respective levorotating or dextrorotating form.

Cyclooxygenase-2 (COX-2) is an enzyme complex present in most tissues that produces various prostaglandins and thromboxanes from arachidonic acid. A number of selective COX-2 inhibitors are known in the art. These include, but are not limited to, those described in U.S. Pat. Nos. 5,474, 995, 5,521,213, 5,536,752, 5,550,142, 5,552,422, 5,604,253, 5,604,260, 5,639,780, 5,677,318, 5,691,374, 5,698,584, 5,710,140, 5,733,909, 5,789,413, 5,817,700, 5,849,943, 5,861,419, 5,922,742, 5,925,631, and 5,643,933. A number of the above-identified COX-2 inhibitors are prodrugs of selective COX-2 inhibitors and exert their action by conversion in vivo to the active and selective COX-2 inhibitors. The active and selective COX-2 inhibitors formed from the above-identified COX-2 inhibitor prodrugs are described in detail in PCT/WO95/00501, PCT/WO95/18799, and U.S. Pat. No. 5,474,995. Given the teachings of U.S. Pat. No. 5,543,297, a person of ordinary skill in the art would be able to determine whether an agent is a selective COX-2 inhibitor or a precursor of a COX-2 inhibitor.

Angiotensin system inhibitors are capable of interfering with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4, 5, 6, 7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenyl and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(–1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF 108566 (E-alpha-2-[2-butyl-1-(carboxy phenyl) methyl]1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D. Searle and Company).

Angiotensin converting enzyme (ACE) is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies. Significantly, as is well-known in the art, only a small portion of an antibody molecule, the paratrope, is involved in the binding of the antibody to its epitope (see, in general, Clark, W. R. (1986) The Experimental Foundations of Modern Immunology, Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (Frs), which maintain the tertiary structure of the paratope (see, in general, Clar, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention involves polypeptides of numerous size and type that bind specifically to cellular adhesion molecules. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using, e.g., m13, fd, or lambda phage), displaying inserts from 4 to about 80 amino acid residues using conventional procedures. The inserts may represent, for example, a completely degenerate or biased array. One then can select phage-bearing inserts which bind to the cellular adhesion molecule. This process can be repeated through several cycles of reselection of phage that bind to the cellular adhesion molecule. Repeated rounds lead to enrichment of phage bearing particular sequences. DNA sequences analysis can be conducted to identify the sequences of the expressed polypeptides. The minimal linear portion of the sequence that binds to the cellular adhesion molecule can be determined. One can repeat the procedure using a biased library containing inserts containing part of all of the minimal linear portion plus one or more additional degenerate residues upstream or downstream thereof. Yeast two-hybrid screening methods also may be used to identify polypeptides that bind to the cellular adhesion molecules. Thus, cellular adhesion molecules, or a fragment thereof, can be used to screen peptide libraries, including phage display libraries, to identify and select peptide binding partners of the cellular adhesion molecules.

Kits

Any of the compounds described herein (e.g., a compound according to any of formulas (I)-(XXVI) or any of compounds (1)-(27)), or pharmaceutical compositions of the invention can be used together with a set of instructions, i.e., to form a kit. The kit may include instructions for use of the compounds of the invention in a screening method or as a therapy as described herein.

The following non-limiting examples are illustrative of the present invention.

Examples

Synthesis of Compounds

The compounds described herein can be prepared by methods well known in the art, including the preparative method shown in Scheme 1.

Scheme 1

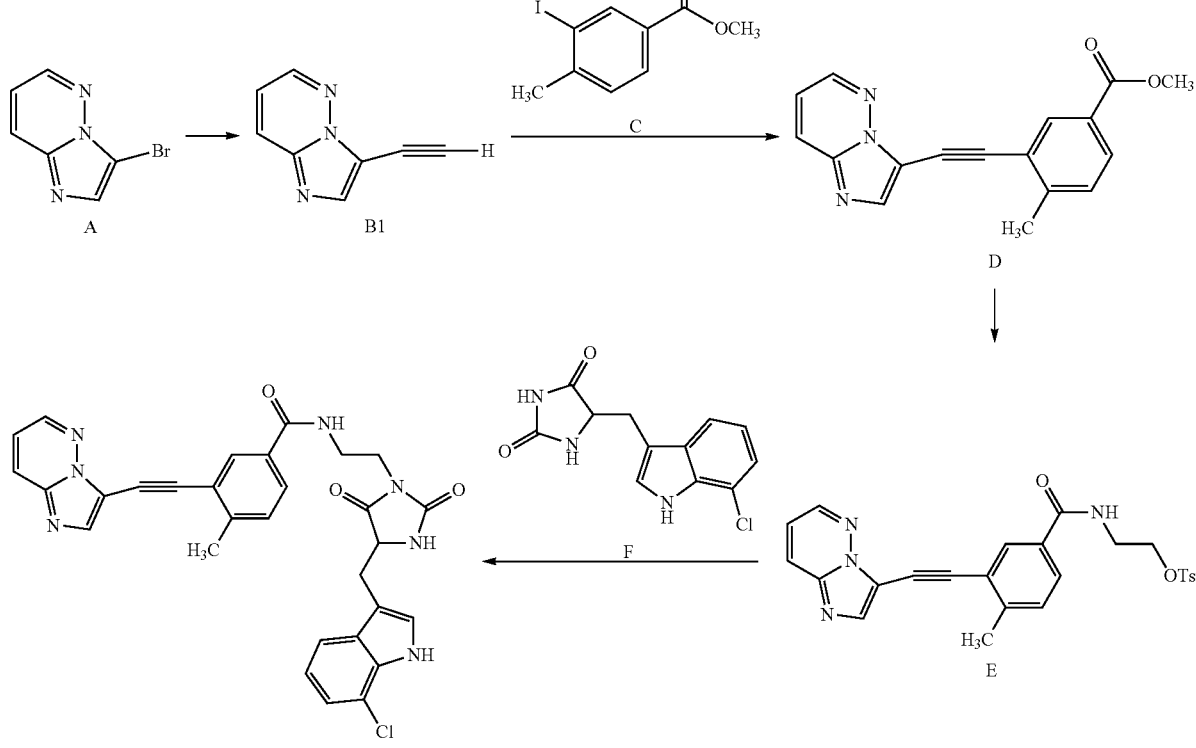

(3)

As shown in Scheme 1, standard cross-coupling techniques can be used to assemble the heteroaryl-aryl intermediate D. For example, a suitable electrophilic compound such as heteroaryl bromide A can be transformed to the corresponding alkyne B1 under, e.g., Sonogashira coupling conditions with alkynes such as TMS-C≡CH. Intermediate B1 can then be treated with an electrophilic compound such as phenyliodide C in order to afford the disubstituted alkyne product D. The methyl ester moiety of compound D can provide a useful handle for further modification of the compounds, such as the installation of an amide moiety as shown in compound E, where the tosyloxy group can be nucleophilically displaced by a fragment $A^1$ precursor such as compound F. In this manner, compounds such as Compound (3) can be prepared.

The above Scheme 1 can be readily modified in order to afford various compounds encompassed by the present claims. For example, other heteroaryl halides or sulfonates can be employed as compound A; similar variation is possible for other intermediates such as compound D, where various phenyl halides or phenyl sulfonates can be employed. Intermediate F can be replaced with other A1 fragment precursors as shown herein. Exemplary modifications to the general synthetic scheme are provided in Schemes 2-6

Scheme 2

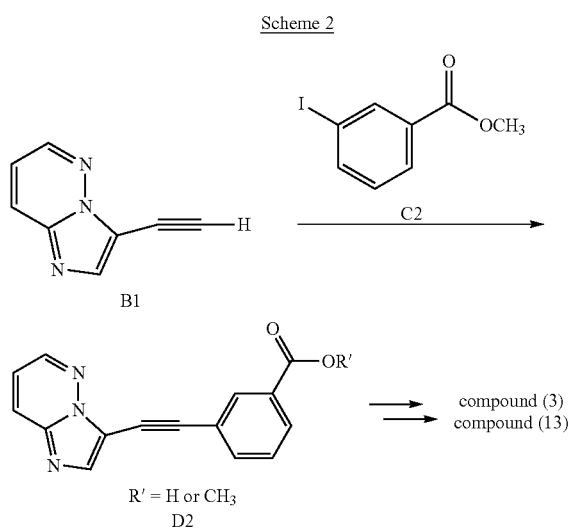

In Scheme 2, Sonogashira-type coupling of alkyne B1 and phenyliodide C2 can afford the carboxylic intermediate D2, which can then be coupled with various substructure A1 precursors such as compound F to afford the desired product.

Scheme 3

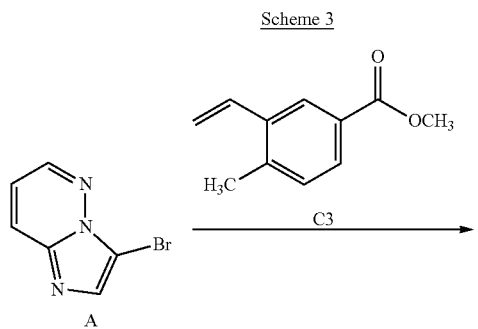

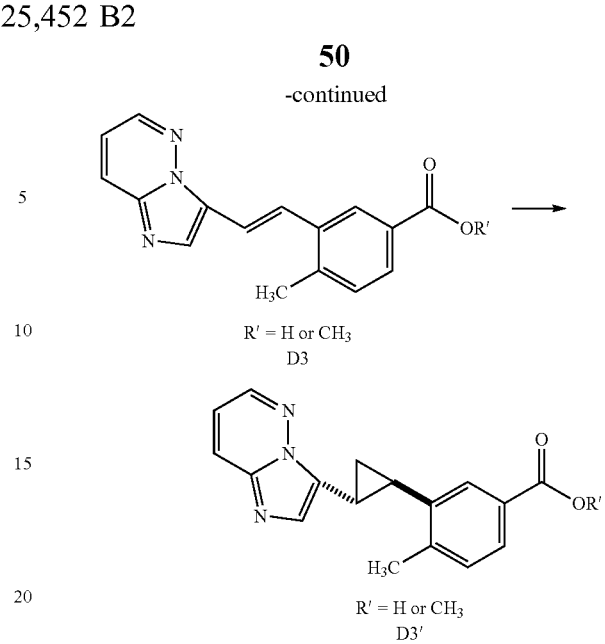

In Scheme 3, an olefin cross-coupling reaction between a heteroaryl halide such as compound A and styrene derivative C3 can be employed to form the disubstituted olefin intermediate D3. Compound D3 can be used directly or it can be cyclopropanated using standard techniques to afford intermediate D3'.

Scheme 4 shows that alkyne intermediate D can be further manipulated in order to afford still other compounds of the invention that, e.g., include different $L^1$ linker groups.

Scheme 4

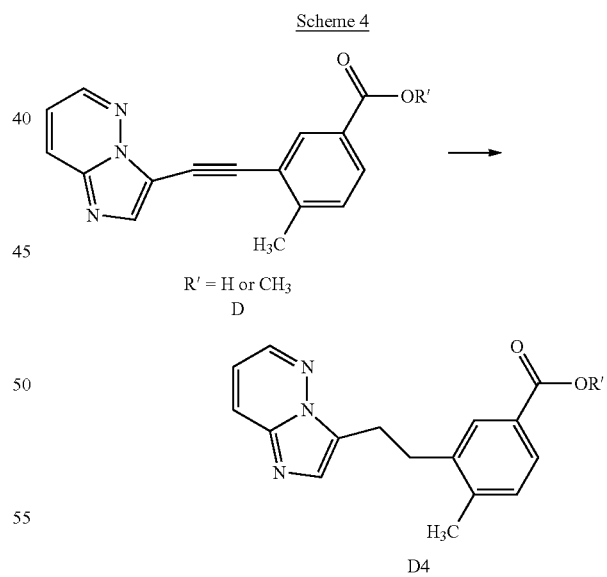

In Scheme 4, complete reduction of the alkyne to the corresponding alkane affords intermediate D4. Partial hydrogenation could similarly afford a compound that included a C2 alkenylene as the $L^1$ group.

Still other compounds of the invention that include, e.g., various $L^2$ linker groups can be prepared by variation of the amine starting material used in the amide synthesis step, as shown in Scheme 5.

Scheme 5

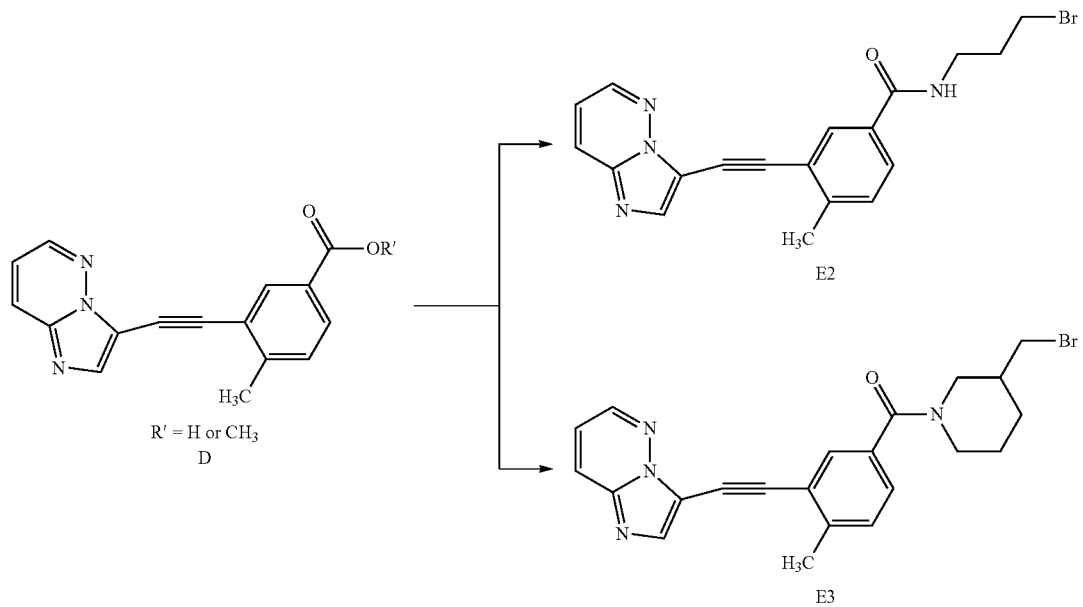

A complementary strategy for the preparation of the instantly claimed compounds that feature a pyrrole-containing moiety as substructure A1 is provided in Scheme 6.

conditions with benzylamine L1 can that afford the desired substructure A1 precursor M1, which can be deprotected and coupled with intermediates such as Compound D.

Scheme 6

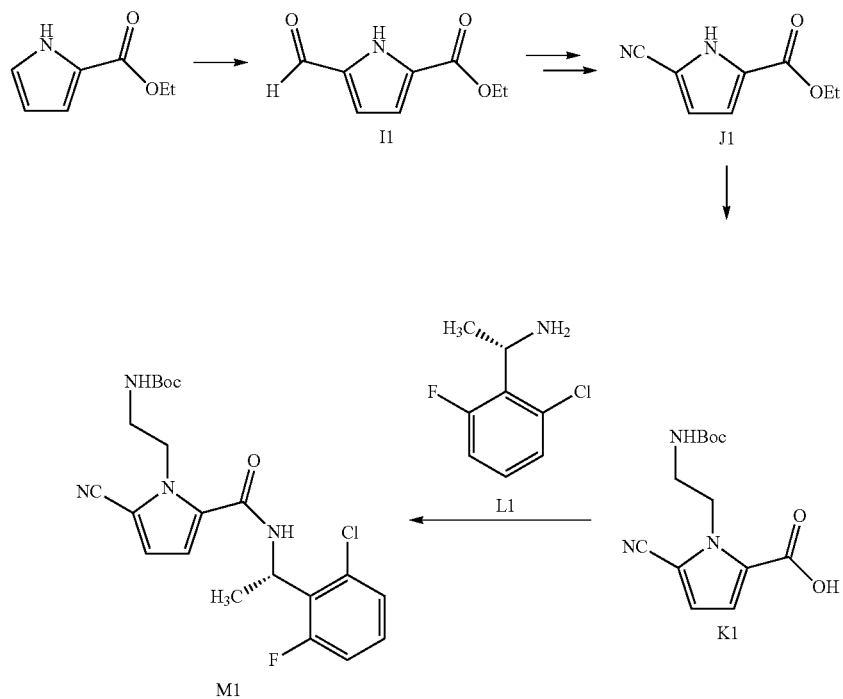

In Scheme 6, the pyrrole carboxylic ester starting material can be formylated to afford intermediate I1, and the formyl group can be transformed to a nitrile under standard conditions to afford product J1. Hydrolysis and N-alkylation can then yield compound K1. Treatment under amide forming Scheme 7 provides still more methods by which to prepare compounds of the invention by treating carboxylic intermediates such as compound K1 with different benzylamine reagents such as compounds L2 and L3 in order to afford, respectively, intermediates M2 and M3.

Scheme 7

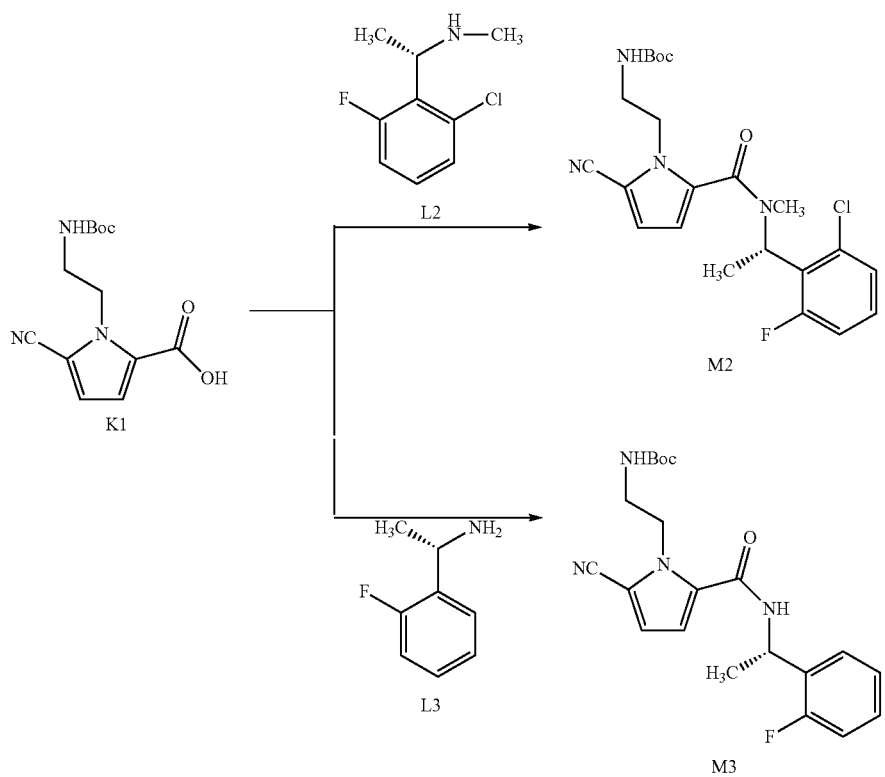

The following two schemes show that different linkers can be introduced by variation of the N-alkylating agent.

upon treatment with a suitable benzylamine under amide bond forming conditions.

Scheme 8

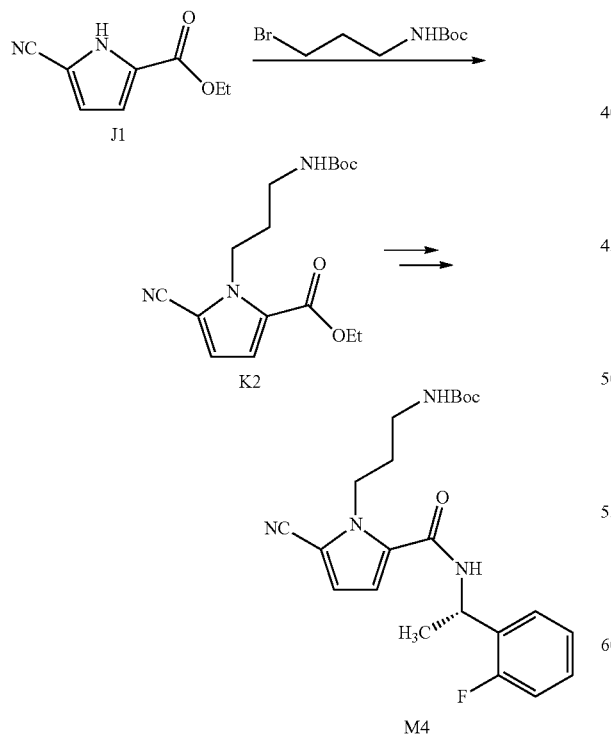

Scheme 9

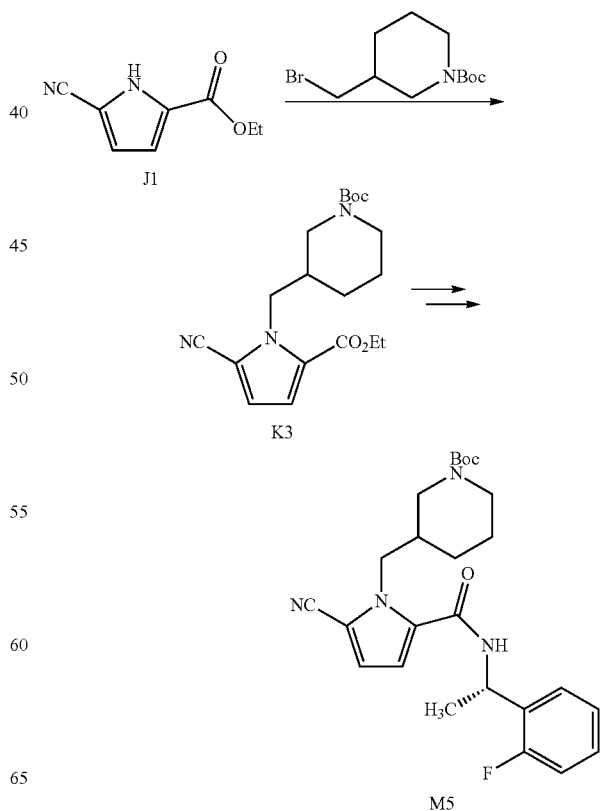

In Scheme 8, the combination of pyrrole compound J1 with Br(CH$_2$)$_3$NHBoc can afford intermediate K2, which can then be converted to the corresponding carboxamide M4

Similarly, Scheme 9 shows that heterocyclic groups can also be introduced into the compounds of the invention by the use of an appropriate alkylating agent.

Still further analogues can be prepared as shown in Scheme 10.

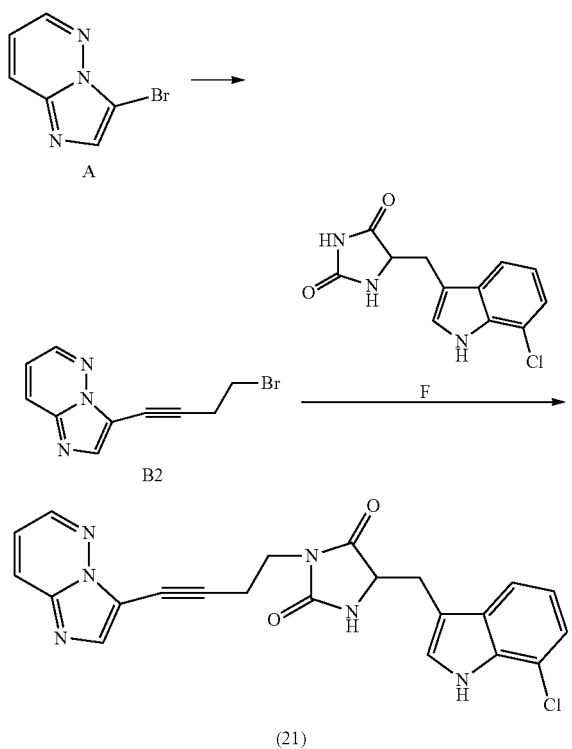

Heteroaryl halides such as compound A can be transformed to homopropargyl halides such as compound B, which, in turn, can be used as an alkylating agent when combined with compound F in order to afford compound (21).

Assays for Identifying Inhibitors of Necrosis and Necroptosis

Evaluation of necroptosis inhibitory activity can be performed using a FADD-deficient variant of human Jurkat T cells treated with TNF-α as previously described (Degterev et al., *Nat. Chem. Biol.* 1:112 (2005) and Jagtap et al., *J. Med. Chem.* 50: 1886 (2007)). For $EC_{50}$ value determinations, cells can be treated with 10 ng/mL of human TNF-α in the presence of increasing concentration of test compounds for 24 hours followed by ATP-based viability assessment.

ATP-based viability assessment: Briefly, necroptosis activity can be performed using a FADD-deficient variant of human Jurkat T cells treated with TNF-α. For $EC_{50}$ value determinations, cells (500,000 cells/mL, 100 μL per well in a 96-well plate) can be treated with 10 ng/mL of human TNF-α in the presence of increasing concentration of test compounds for 24 hours at 37° C. in a humidified incubator with 5% $CO_2$ followed by ATP-based viability assessment. Stock solutions (30 mM) in DMSO can be prepared and then diluted with DMSO to give testing solutions, which were added to each test well. The final DMSO concentration can be 0.5%. Eleven compound test concentrations (0.030-100 μM) can be used, and each concentration can be done in duplicate.

Cell viability assessments can be performed using a commercial luminescent ATP-based assay kit (CellTiter-Glo, Promega, Madison, Wis.) according to the manufacturer's instructions. Briefly, 40 μL of the cell lysis/ATP detection reagent can be added to each well. Plates can be incubated on a rocking platform for 10 minutes at room temperature and luminescence was measured using a Wallac Victor 3 plate-reader (Perkin Elmer, Wellesley, Mass.). Cell viability can be expressed as a ratio of the signal in the well treated with TNF-α and compound to the signal in the well treated with compound alone in order to account for non-specific toxicity. $EC_{50}$ values can be calculated using non-linear regression analysis of sigmoid dose-response (variable slope) curves from plots of log [I] verses viability values.

Activity may be also demonstrated using still other procedures known in the art (see, for example, Teng et al., *Bioorg. Med. Chem. Lett.*, 15: 5039 (2005) and Jagtap et al., *J. Med. Chem.* 50: 1886(2007)).

Liver Microsome Stability Assays

Microsome stability can be determined in pooled mouse liver microsomes. A test compound (3 μM final concentration) along with 0.5 mg/mL microsome protein and 1 mM NADPH can be incubated for 0, 5, 15, 30 and 60 minutes. Incubation of test compound and microsomes in the absence of NADPH can serve as a negative control. The samples can be quenched with methanol and centrifuged for 20 minutes at 2500 rpm to precipitate proteins. Sample supernatants can be analyzed (N=3) by LC/MS. The ln peak area ratio (compound peak area/internal standard peak area) can be plotted against time and the slope of the line determined to give the elimination rate constant [k=(−1)(slope)]. The half life ($t_{1/2}$ in minutes), and the in vitro intrinsic clearance ($CL_{int}$ in μL/min/mg protein) can be calculated according to the following equations, where V=incubation volume in μL/mg protein:

$$t_{1/2} = \frac{0.693}{k}; \; CL_{int} = \frac{V(0.693)}{t_{1/2}}.$$

Homology Modeling and Ligand Docking

The RIP1 kinase domain, between residues 17-285, was modeled using MODELLER (Eswar et al. *Nucleic Acids Res* 2003, 31(13):3375-3380; Piper et al., *Nucleic Acids Res* 2004, 32 (Database issue):D217-222; Sanchez et al., *Proteins* 1997, Suppl 1:50-58). Briefly, the main criteria in homology modeling were template selection and sequence alignment between the target and the template. The structure of Aurora kinase (>30% identity) was used for homology modeling since this enzyme has higher sequence conservation around the active site region to RIP1 than other kinases. The Cα RMSD and the backbone RMSD deviations for the model and the template crystal structure were <1.0 Å and <1.2 Å respectively. The best model was subjected to geometric evaluations using PROCHECK (Laskowski et al., *J Biomol NMR* 1996, 8(4):477-486) with an overall G-value of −0.05. Ramachandran plots indicated that >93% of the residues are in the allowed region of the map (Laskowski et al., *J Biomol NMR* 1996, 8(4):477-486; and Potteron et al., *Acta Crystallogr D Biol Crystallogr* 2003, 59 (Pt 7):1131-1137). Standard bond lengths and bond angles of the model were determined using WHAT IF (Hooft et al., *Nature* 1996, 381(6580):272) with an RMS-Z score of 0.8 and 0.9 suggesting that the model is of high quality (Vaguine et al., *Acta Crystallogr D Biol Crystallogr* 1999, 55 (Pt 1):191-205).

Induced Fit Docking

Glide 4.5 (Sherman et al., *J Med Chem* 2006, 49(2):534-553; Friesner et al., *J Med Chem* 2004, 47(7):1739-1749; and Halgren et al., *J Med Chem* 2004, 47(7):1750-1759) was used for all docking calculations of both DLG-in and DLG-out structures of RIP1. Induced fit docking protocol with a softened-potential docking was performed to generate 20 initial poses. The softened-potential docking consisted of scaling the van der Waals radii by 0.5 except in the event when alanine substitutions were introduced, in which case the receptor scaling was set to 0.7. In this case Lys 24, Val 55 and Leu 136 were mutated to alanine to enhance the hit rate of poses in the initial docking that are close to the correct answer, the Glide hydrogen bond energy cutoff filter was decreased to −0.05 kcal/mol. This ensures that all retained poses contain at the very least a weak hydrogen bond with the receptor with backbone amide of Met 74. Second, the Glide Coulomb-vdW energy cutoff filter was increased to 10 kcal/mol, enabling toleration of more steric clashes than in a normal docking run. Poses with an RMSD of less than 0.5 Å and a maximum atomic displacement of less than 1.2 Å were eliminated as redundant in order to increase diversity in the retained ligand poses. An inner grid box of 10 Å was used to fit the ligand center and an outer box size of 20 Å was used.

For each of the top 20 poses (with respect to GlideScore) from the initial softened-potential docking step, a full cycle of protein refinement was performed. Prime uses the OPLS-AA parameter and a surface Generalized Born implicit solvent model. First, a list was generated consisting of all residues having at least one atom within 5 Å of an atom in any of the 20 ligand poses. All side chains in the list underwent a conformational search and minimization. Three residues that were mutated to alanine in the initial docking stage were returned to their original identity prior to the search. After convergence to a low-energy solution, an additional minimization was performed allowing all residues in the list (backbone and side chain) and the ligand to be relaxed. The complexes were ranked by Prime energy (molecular mechanics plus solvation) and those within 30 kcal/mol of the minimum energy structure were passed through for a final round of Glide docking and scoring.

The minimized ligand used in the first docking step is redocked using Glide with default settings into each of the 10 receptor structures produced in protein refinement step. A composite score that accounts for the protein/ligand interaction energy (GlideScore) (Friesner et al., *J Med Chem* 2004, 47(7):1739-1749; and Halgren et al., *J Med Chem* 2004, 47(7):1750-1759)), and the total energy of the system (Prime energy) is calculated using the following equation: (GlideScore)+(0.05×PrimeEnergy).

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:
1. A compound of formula (I):

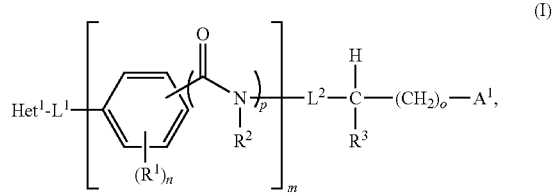

or any pharmaceutically acceptable salt thereof, or stereoisomer thereof, wherein m is 0 or 1;
Het$^1$ is a bicyclic heteroaryl, wherein the bicyclic heteroaryl is unsubstituted or substituted by 1 or 2 substituents selected from halogen, CN, NO$_2$, C1-C6 alkyl, and C1-C6 alkoxy;
L$^1$ is a covalent bond, a C1-C4 alkylene, a C2-C4 alkenylene, a C2-C4 alkynylene, a C3-C6 cycloalkyl, or a 3-6 membered heterocyclyl;
n is 0, 1, 2, 3, or 4;
o is 0 or 1;
p is 0 or 1;
each R$^1$, when present, is independently C1-C6 alkyl, C2-C6 alkenyl, C2-C6 alkynyl, C3-C9 cycloalkyl, C5-C9 cycloalkenyl, 3-9 membered heterocyclyl, C6-C10 aryl, 5-11 membered heteroaryl, halogen, —OH, N$_3$, NO$_2$, —CO$_2$H, —NC, or CN; or is a group selected from —OC(=O)R$^{4A}$, —C(=O)R$^{4A}$, —OR$^{4A}$, —NR$^{4A}$C(=O)R$^{4B}$, —C(=O)NR$^{4A}$R$^{4B}$, —NR$^{4A}$R$^{4B}$, —CO$_2$R$^{4A}$, —OC(=O)NR$^{4A}$R$^{4B}$, —NR$^{4A}$C(=O)OR$^{4B}$, —S(=O)$_2$OR$^{4A}$, —S(=O)$_2$NR$^{4A}$R$^{4B}$, —NR$^{4A}$S(=O)$_2$R$^{4B}$, and —S(=O)$_2$R$^{4A}$, where each R$^{4A}$ and R$^{4B}$ is independently H, C1-C6 alkyl, C2-C6 alkenyl, C2-C6 alkynyl, C3-C9 cycloalkyl, 3-9 membered heterocyclyl, C6-C10 aryl, or 5-11 membered heteroaryl;
R$^2$ is H or C1-C6 alkyl, or R$^2$ combines with R$^3$ to form a C1-C3 alkylene moiety;
L$^2$ is a covalent bond or C1-C4 alkylene;
R$^3$ is H or C1-C6 alkyl, or R$^3$ combines with R$^2$ to form a C1-C3 alkylene moiety;
A$^1$ is

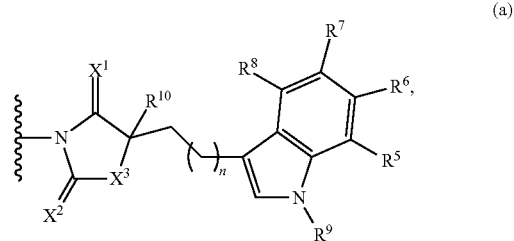

wherein
each X$^1$ and X$^2$ is independently O or S;
X$^3$ is O or NR$^H$;
n is 0 or 1;

each of $R^5$, $R^6$, $R^7$ and $R^8$ is independently H, OH, C1-C6 alkyl, C1-C6 alkoxy, halogen, $N(R^{12})_2$, $CO_2R^{12}$, $NO_2$, $NHC(O)R^{12}$, aryl, heteroaryl, or piperazinyl;

$R^9$ is H or C1-C6 alkyl;

$R^{10}$ is H or C1-C6 alkyl;

$R^{11}$ is H or C1-C6 alkyl; and each $R^{12}$ is independently H, C1-C6 alkyl, aryl, alkaryl, C2-C6 alkenyl, C2-C6 alkynyl, or heteroaryl;

or

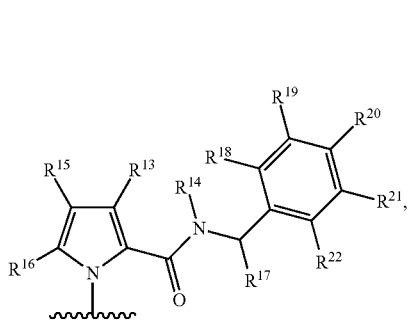

(b)

wherein $R^{13}$ is H, halogen, C1-C6 alkyl, C1-C6 cycloalkyl, or aryl;

$R^{14}$ is H or C1-C6 alkyl;

each of $R^{15}$ and $R^{16}$ is independently H, halogen, carboxamido, nitro or cyano;

$R^{17}$ is H, aryl or C1-C6 alkyl; and each of $R^{18}$, $R^{19}$, $R^{20}$, $R^{21}$ and $R^{22}$ is independently H, C1-C6 alkyl, halogen, amino, carboxamido, C1-C6 alkoxy, nitro or cyano.

2. The compound of claim 1, wherein said compound has a structure according to formula (II), formula (III), formula (IV) or formula (V):

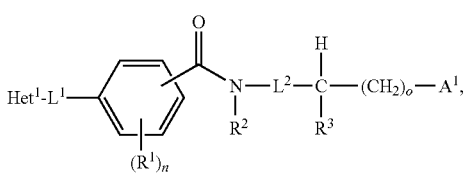

(II)

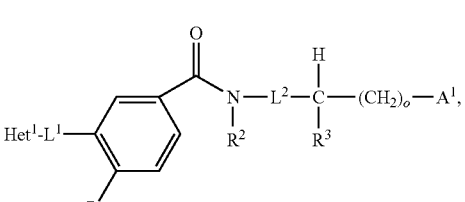

(III)

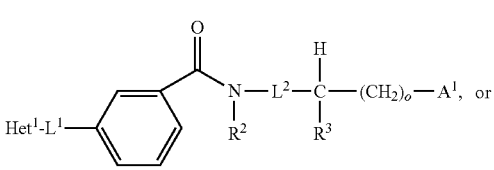

(IV)

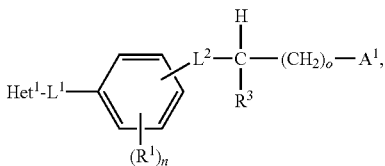

(V)

or any pharmaceutically acceptable salt thereof, or stereoisomer thereof.

3. The compound of claim 1, wherein said compound has a structure according to formula (VI) or formula (VII),

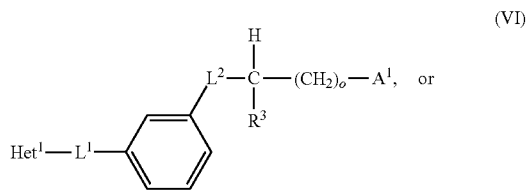

(VI)

(VII)

or any pharmaceutically acceptable salt thereof, or stereoisomer thereof.

4. The compound of claim 1, wherein o is 0, or any pharmaceutically acceptable salt thereof, or stereoisomer thereof.

5. The compound of claim 4, wherein said compound has a structure according to formula (VIII) or formula (IX),

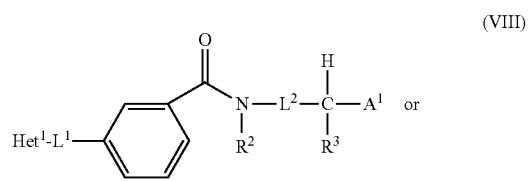

(VIII)

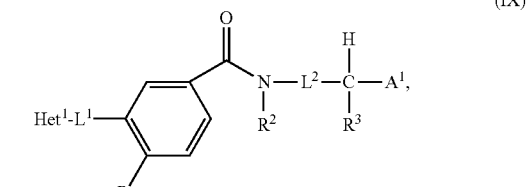

(IX)

or any pharmaceutically acceptable salt thereof, or stereoisomer thereof.

6. The compound of claim 1, wherein said compound has a structure according to formula (X), formula (XI), formula (XII), formula (XIII), formula (XIV), formula (XV), formula (XVI), formula (XVII), formula (XVIII), formula (XIX), formula (XX) or formula (XXI), (a) 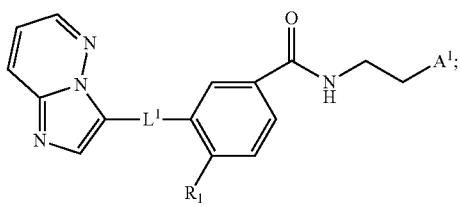 (X)
(b) 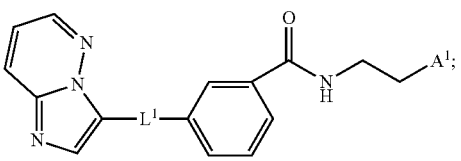 (XI)
(c) 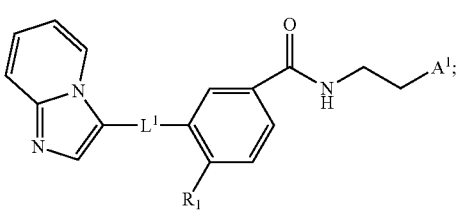 (XII)
(d) 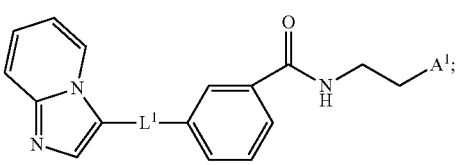 (XIII)
(e) 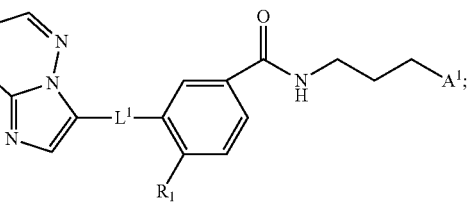 (XIV)
(f) 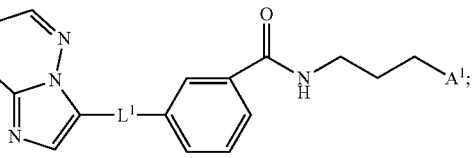 (XV)
(g) 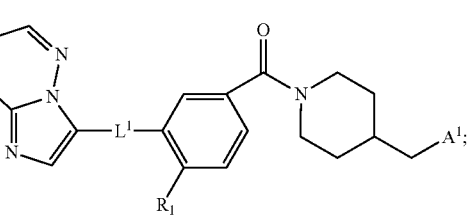 (XVI)
-continued
(h) 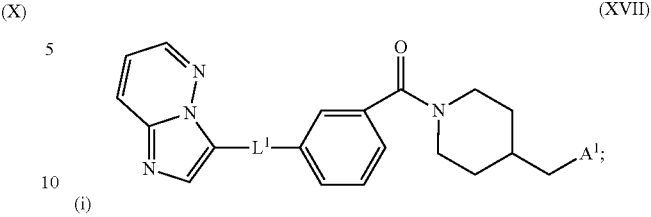 (XVII)
(i) 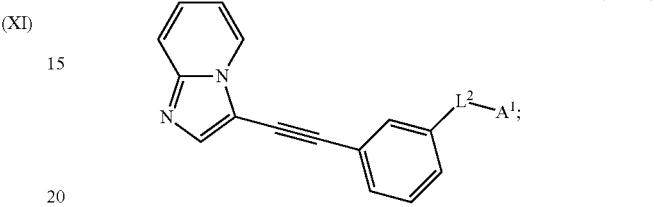 (XVIII)
(j) 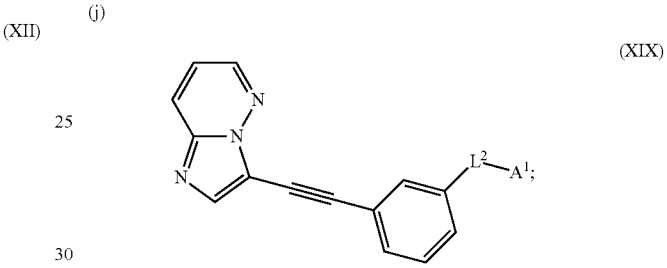 (XIX)
(k) 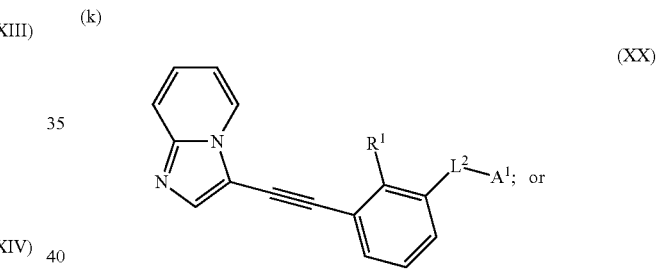 (XX)
(l) 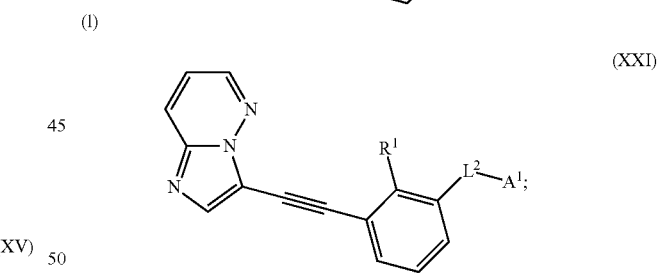 (XXI)
or any pharmaceutically acceptable salt thereof, or stereoisomer thereof.
7. The compound of claim 1, wherein m is 0 and said compound has a structure according to formula (XXII),
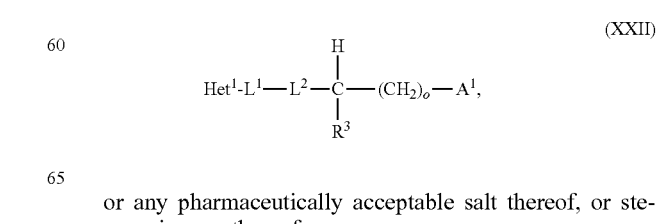 (XXII)
or any pharmaceutically acceptable salt thereof, or stereoisomer thereof.

8. The compound of claim 7, wherein

L¹ is C2 alkynylene; and/or o is 0; and/or

L² is C1 alkylene; and/or

R³ is H, or any pharmaceutically acceptable salt thereof, or stereoisomer thereof.

9. The compound of claim 1, wherein said compound has a structure according to a structure according to formula (XXIII), formula (XXIV), or formula (XXV), or formula (XXVI), (a)

(XXIII)

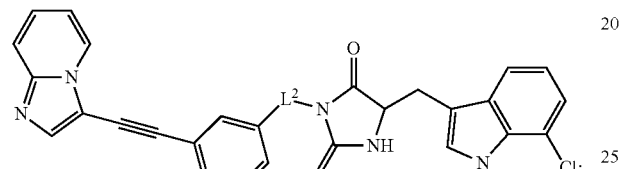

(b)

(XXIV)

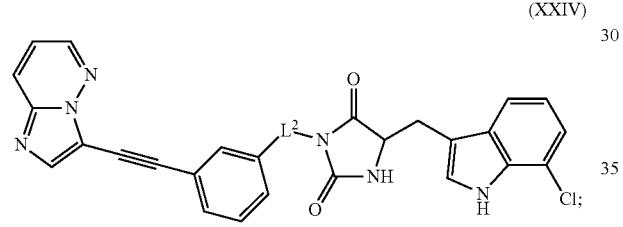

(c)

(XXV)

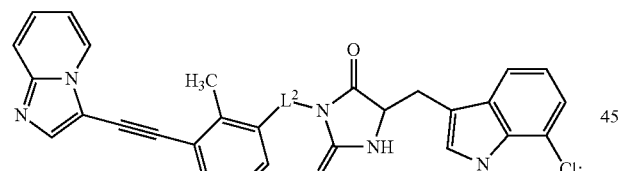

(d)

(XXVI)

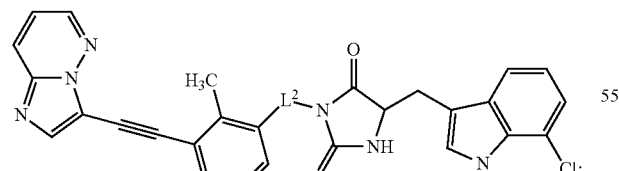

or any pharmaceutically acceptable salt thereof, or stereoisomer thereof.

10. The compound of claim 9, wherein L² is C1-C4 alkylene, or any pharmaceutically acceptable salt thereof, or stereoisomer thereof.

11. The compound of claim 1, wherein A¹ is

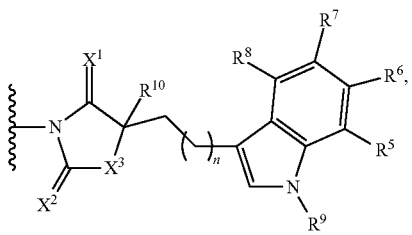

or any pharmaceutically acceptable salt thereof, or stereoisomer thereof.

12. The compound of claim 11, wherein A¹ is

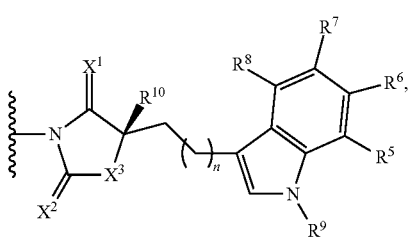

or any pharmaceutically acceptable salt thereof, or stereoisomer thereof.

13. The compound of claim 11, wherein A¹ is

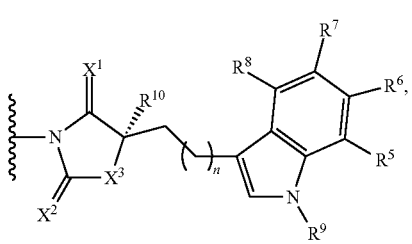

or any pharmaceutically acceptable salt thereof, or stereoisomer thereof.

14. The compound of claim 1, wherein A¹ is

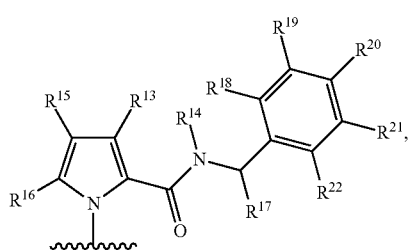

or any pharmaceutically acceptable salt thereof, or stereoisomer thereof.

15. The compound of claim 14, wherein $A^1$ is

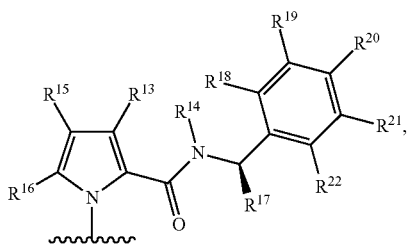

or any pharmaceutically acceptable salt thereof, or stereoisomer thereof.

16. The compound of claim 14, wherein $A^1$ is

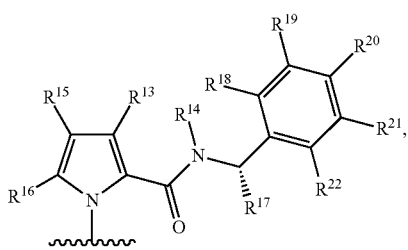

or any pharmaceutically acceptable salt thereof, or stereoisomer thereof.

17. The compound of claim 1, wherein $A^1$ is

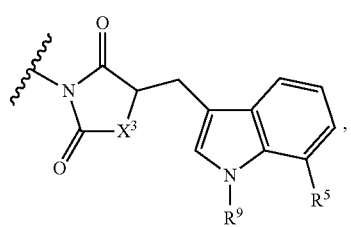

wherein
$X^3$ is O or NH;
$R^9$ is H or C1 alkyl; and
$R^5$ is H, halogen, OH, C1-C3 alkyl, or C1-C3 alkoxy; or

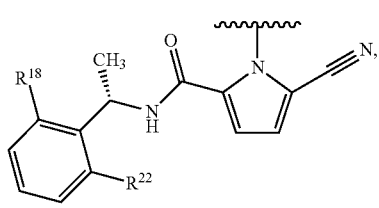

wherein each of $R^{18}$ and $R^{22}$ is independently H, F or Cl.

18. The compound of claim 17, wherein
$A^1$ has a structure according to (a), and $R^5$ is H, Cl, OH, CH$_3$, or OCH$_3$; or wherein
$A^1$ has a structure according to (b), and $R^{18}$ is F and $R^{22}$ is Cl, or $R^{18}$ is F and $R^{22}$ is H.

19. The compound of claim 1, wherein Het$^1$ is indolyl, indazolyl, imidazopyridinyl, imidazopyrimidinyl, pyrrolopyrimidinyl, pyrrolopyridinyl, pyrazolopyridinyl, pyrazolopyrimidinyl, quinolinyl or isoquinolinyl, each of which is unsubstituted or substituted by 1 or 2 substituents selected from halogen, CN, NO$_2$, C1-C6 alkyl, and C1-C6 alkoxy,
or any pharmaceutically acceptable salt thereof, or stereoisomer thereof.

20. The compound of claim 19, wherein Het$^1$ is 1 or 2 substituents selected from halogen, CN, NO$_2$, C1-C6 alkyl, and C1-C6 alkoxy,
or any pharmaceutically acceptable salt thereof, or stereoisomer thereof.

21. The compound of claim 1, wherein Het$^1$ is selected from the group consisting of

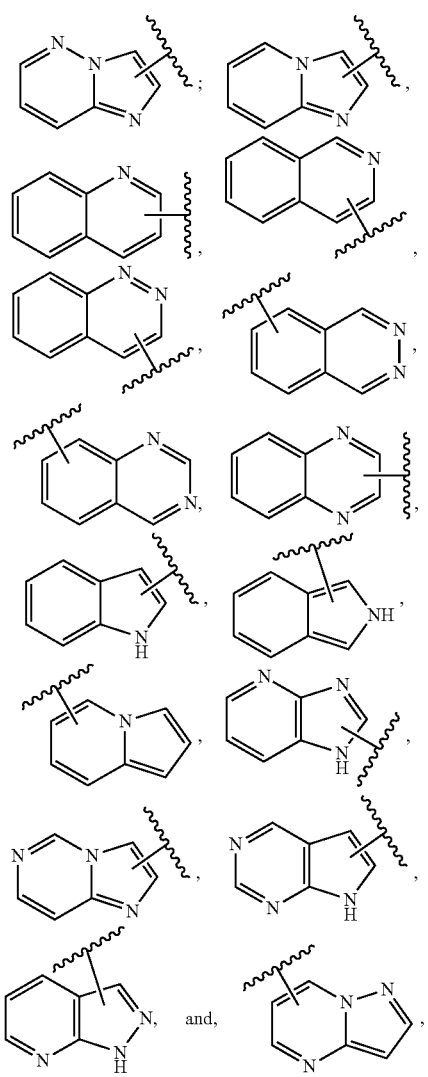

or any pharmaceutically acceptable salt thereof, or stereoisomer thereof.

22. The compound of claim 1, wherein $L^1$ is C1-C2 alkylene, C2 alkenylene, C2 alkynylene, or C3-C6 cycloalkyl,
or any pharmaceutically acceptable salt thereof, or stereoisomer thereof.

23. The compound of claim 1, wherein $L^2$ is C1-C2 alkylene,
or any pharmaceutically acceptable salt thereof, or stereoisomer thereof.

24. The compound of claim 1, wherein each $R^1$, when present, is independently halogen, C1-C6 alkyl, C1-C6 alkoxy or CN,
  or any pharmaceutically acceptable salt thereof, or stereoisomer thereof.

25. The compound of claim 1, wherein $R^2$ is H or $R^3$ is H,
  or any pharmaceutically acceptable salt thereof, or stereoisomer thereof.

26. The compound of claim 1, wherein $R^2$ combines with $R^3$ to form a C1-C3 alkylene moiety,
  or any pharmaceutically acceptable salt thereof, or stereoisomer thereof.

27. The compound of claim 1, wherein n is 0 or 1,
  or any pharmaceutically acceptable salt thereof, or stereoisomer thereof.

28. The compound of claim 1, wherein o is 1,
  or any pharmaceutically acceptable salt thereof, or stereoisomer thereof.

29. The compound of claim 1, wherein said compound is selected from the group consisting of:

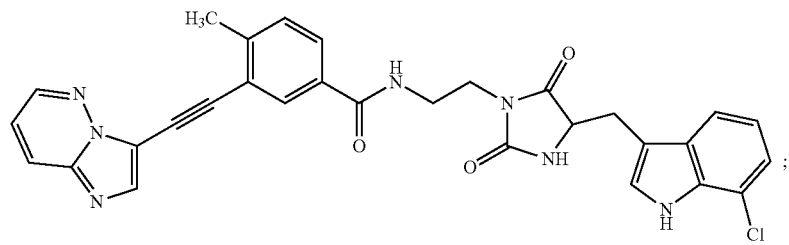

(1)

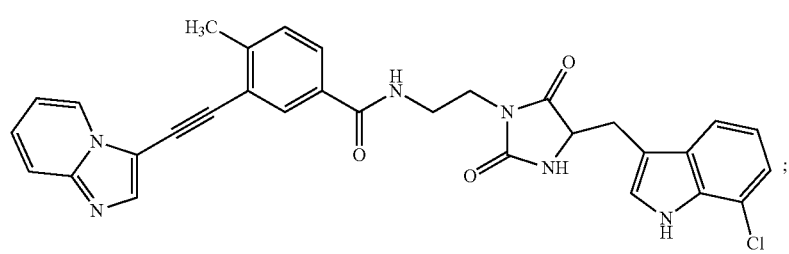

(2)

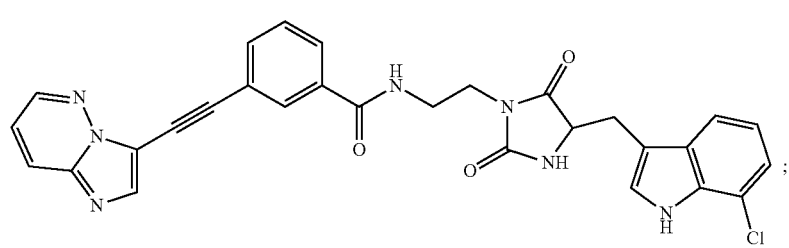

(3)

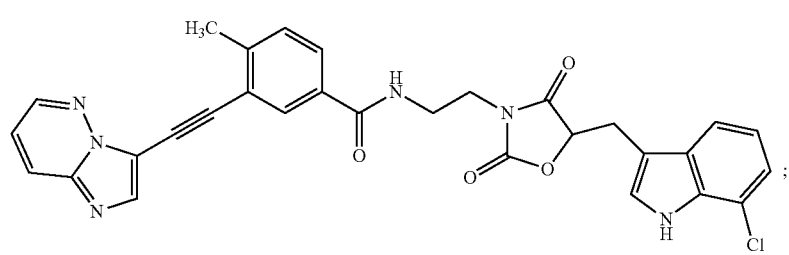

(4)

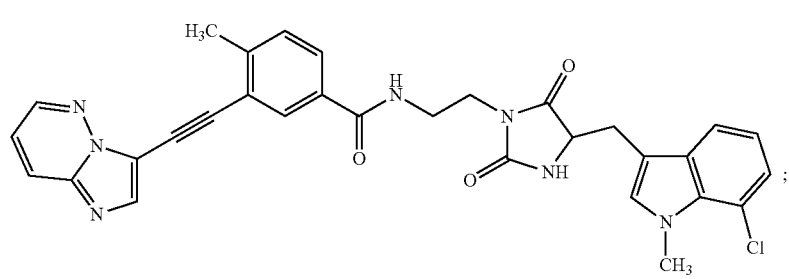

(5)

-continued
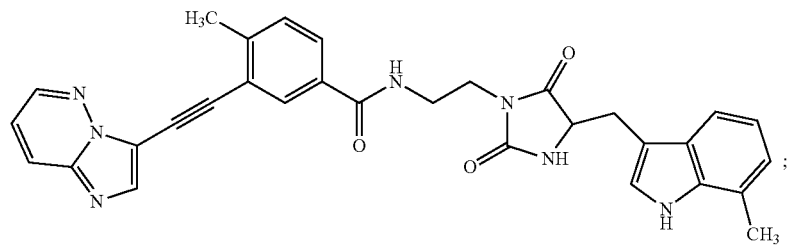
(6)
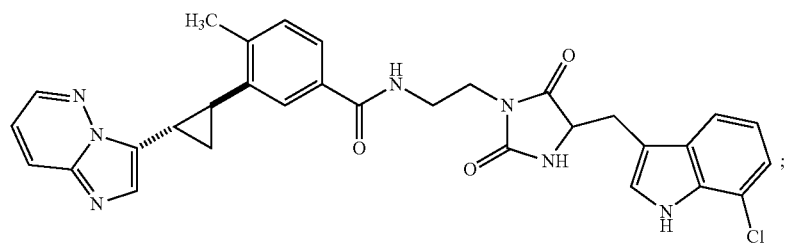
(7)
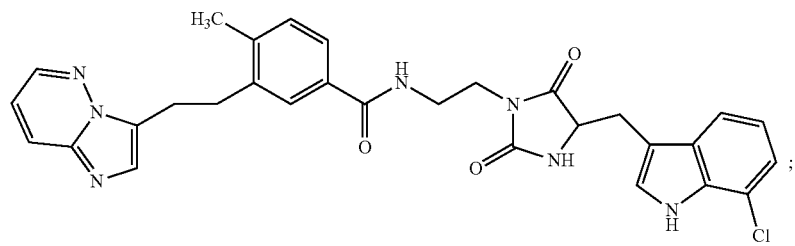
(8)
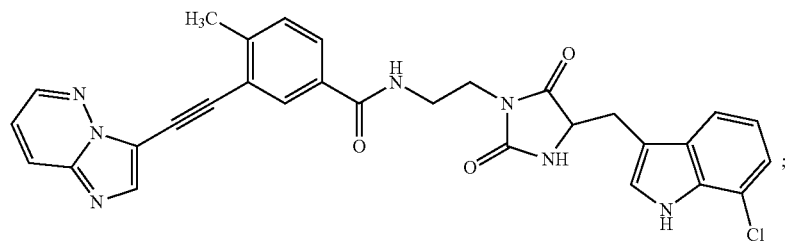
(9)
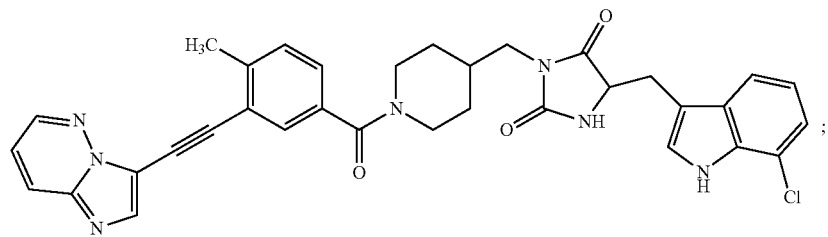
(10)
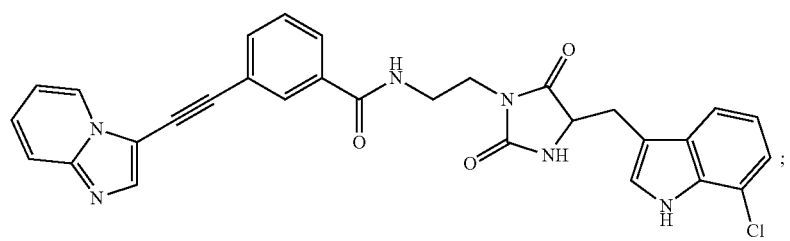
(11)

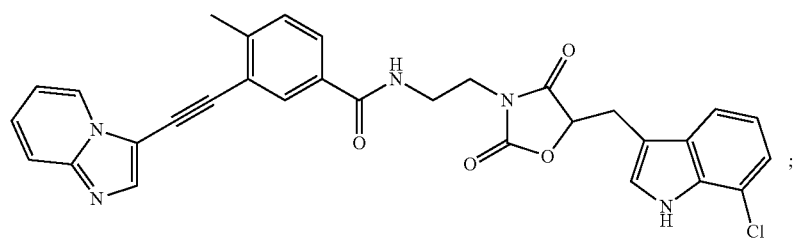
(12)
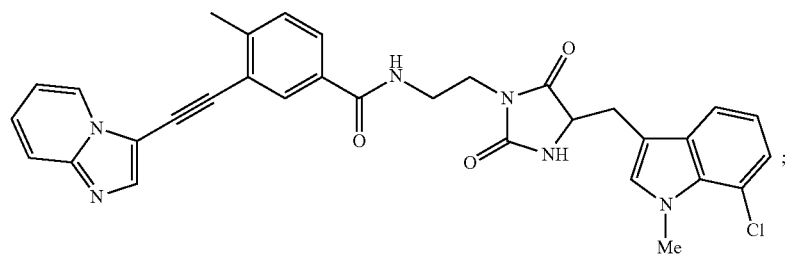
(13)
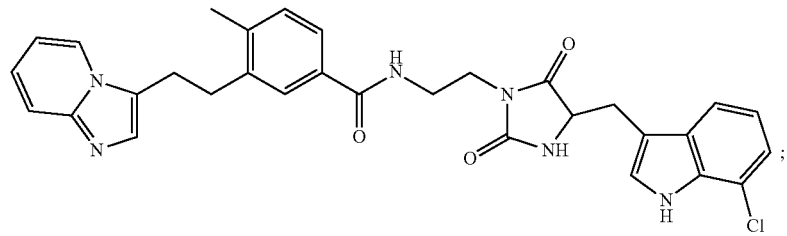
(14)
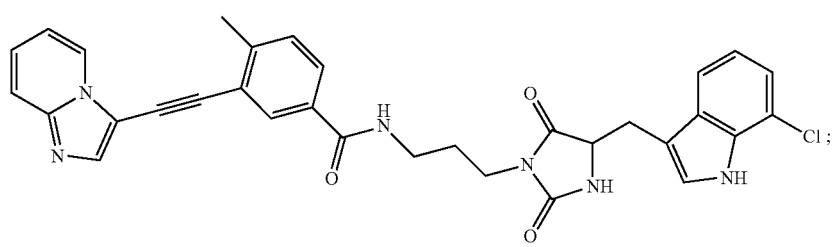
(15)
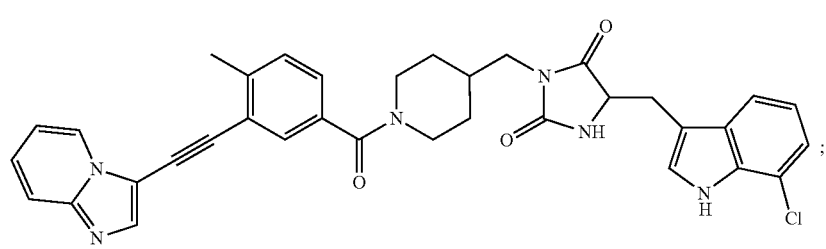
(16)

-continued
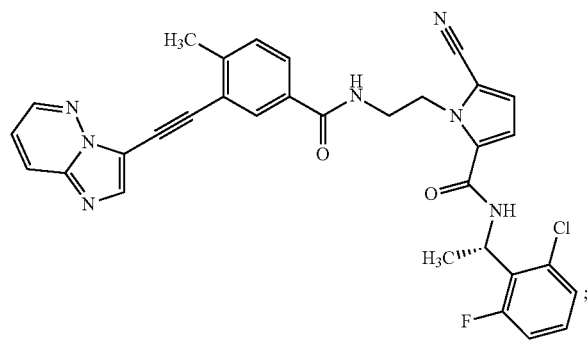
(17)
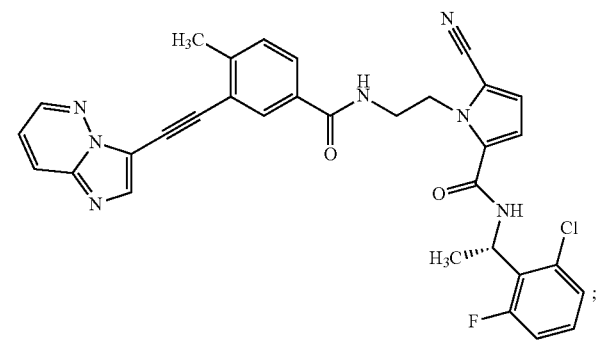
(18)
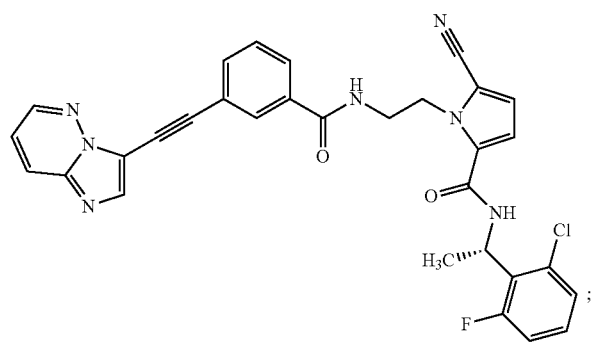
(19)
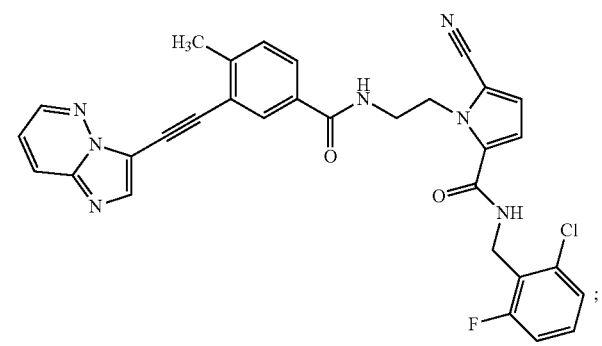
(20)
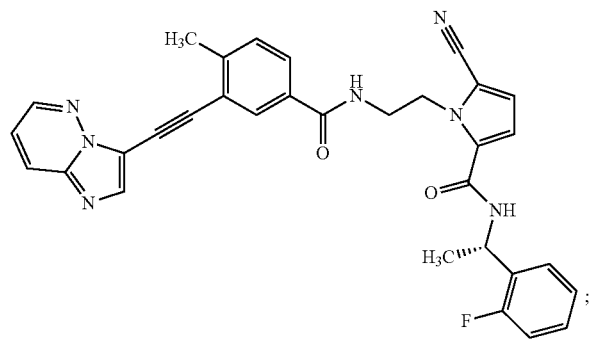
(21)
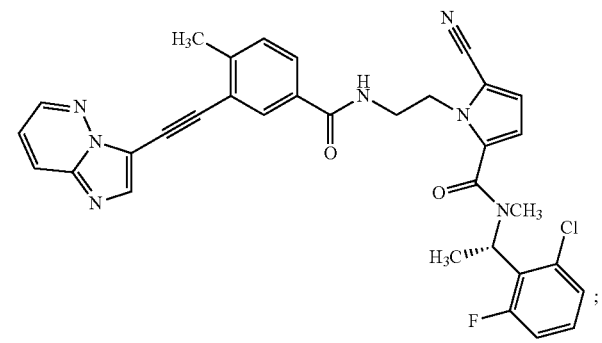
(22)
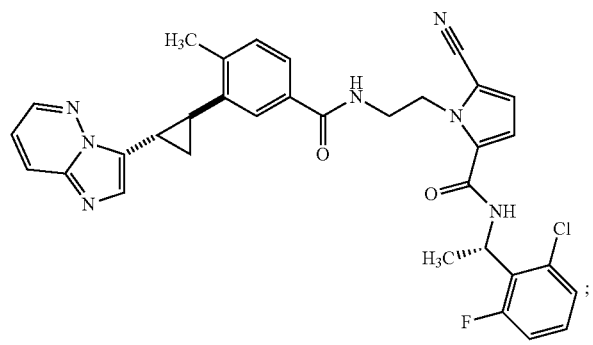
(23)
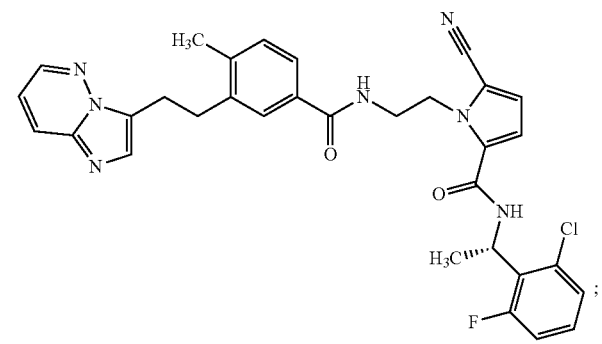
(24)

(25)
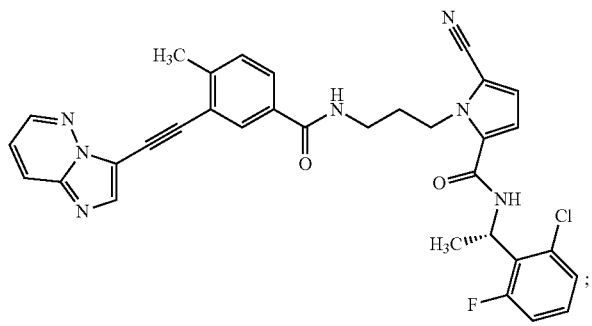

(26)
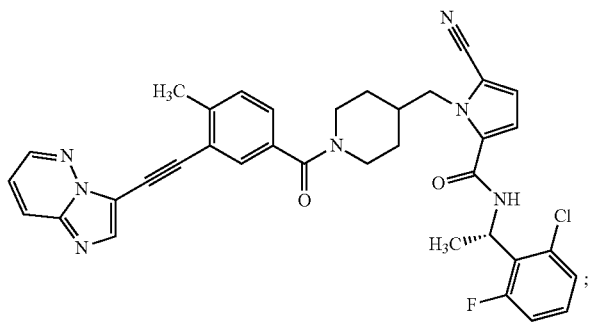

and

(27)
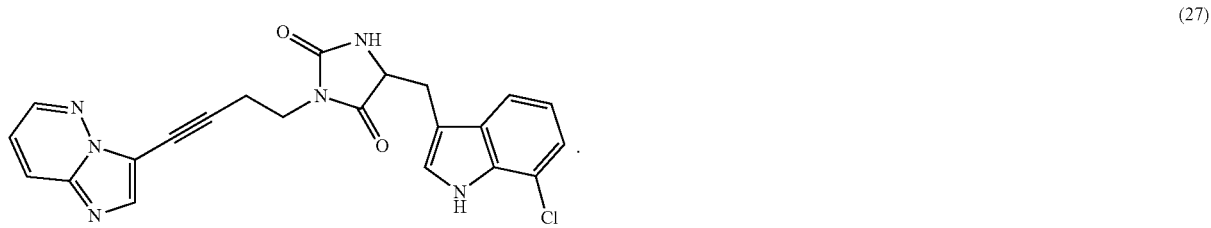

30. A pharmaceutical composition comprising a pharmaceutically acceptable excipient and the compound of claim 1, or any pharmaceutically acceptable salt thereof, or stereoisomer thereof.

31. A kit comprising
(a) a pharmaceutical composition comprising the compound of claim 1, or any pharmaceutically acceptable salt thereof, or stereoisomer thereof, and a pharmaceutically acceptable excipient; and
(b) instructions for the use of the pharmaceutical composition of (a).

32. A method for modulating receptor-interacting protein kinase activity in a subject, comprising the step of contacting the compound of claim 1, or any pharmaceutically acceptable salt thereof, or stereoisomer thereof, with said subject.

33. The method of claim 32, wherein said subject has a disease or condition selected from the group consisting of a neurodegenerative disease of the central or peripheral nervous system, a disease resulting from death of retinal neuronal cells, a disease resulting from death of cardiac muscle cells, a disease resulting from death of immune system cells, a disease resulting from cell death associated with renal failure, pancreatic disease, liver disease, coronary heart disease, sickle cell disease, gastrointestinal disease, graft-versus-host disease, Crohn's disease, heart ischemic injury, mesenteric ischemic injury, retinal ischemic injury, hepatic ischemic injury, brain ischemic injury, ischemic injury during organ storage, stroke, head trauma, septic shock, cardiomyopathy, myocardial infarction, bone avascular necrosis, muscle wasting, tuberculosis, diabetes, alteration of blood vessels, muscular dystrophy, viral infection, ulcerative colitis, asthma, atherosclerosis, pain, a chronic inflammatory condition and an acute inflammatory condition.

34. A method of decreasing necroptosis in a cell, comprising contacting said cell with the compound of claim 1, or any pharmaceutically acceptable salt thereof, or stereoisomer thereof.

* * * * *